United States Patent
Arnold et al.

(10) Patent No.: US 11,938,166 B2
(45) Date of Patent: *Mar. 26, 2024

(54) METHODS AND COMPOSITIONS FOR TREATING MUCOSAL TISSUE DISORDERS

(71) Applicant: The University of North Carolina at Chapel Hill, Chapel Hill, NC (US)

(72) Inventors: Roland R. Arnold, Chapel Hill, NC (US); David C. Henke, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/348,096

(22) Filed: Jun. 15, 2021

(65) Prior Publication Data
US 2022/0143129 A1 May 12, 2022

Related U.S. Application Data

(63) Continuation of application No. 16/529,204, filed on Aug. 1, 2019, now Pat. No. 11,058,743, which is a continuation of application No. 15/040,731, filed on Feb. 10, 2016, now Pat. No. 10,406,200, which is a continuation of application No. 14/446,192, filed on Jul. 29, 2014, now Pat. No. 9,308,234, which is a continuation of application No. PCT/US2013/067307, filed on Oct. 29, 2013.

(60) Provisional application No. 61/719,804, filed on Oct. 29, 2012.

(51) Int. Cl.
| | |
|---|---|
| *A61K 38/06* | (2006.01) |
| *A01N 1/02* | (2006.01) |
| *A61K 9/00* | (2006.01) |
| *A61K 31/198* | (2006.01) |
| *A61K 31/375* | (2006.01) |
| *A61K 33/00* | (2006.01) |
| *A61K 33/04* | (2006.01) |
| *A61K 33/10* | (2006.01) |
| *A61K 38/40* | (2006.01) |
| *A61K 38/44* | (2006.01) |
| *A61K 45/06* | (2006.01) |

(52) U.S. Cl.
CPC .......... *A61K 38/063* (2013.01); *A01N 1/0226* (2013.01); *A61K 9/0031* (2013.01); *A61K 9/0034* (2013.01); *A61K 9/006* (2013.01); *A61K 9/0073* (2013.01); *A61K 9/0075* (2013.01); *A61K 9/008* (2013.01); *A61K 31/198* (2013.01); *A61K 31/375* (2013.01); *A61K 33/00* (2013.01); *A61K 33/04* (2013.01); *A61K 33/10* (2013.01); *A61K 38/40* (2013.01); *A61K 38/443* (2013.01); *A61K 45/06* (2013.01); *C12Y 101/03004* (2013.01); *C12Y 111/01007* (2013.01); *C12Y 302/01011* (2013.01); *C12Y 302/01017* (2013.01); *C12Y 302/01059* (2013.01)

(58) Field of Classification Search
None
See application file for complete search history.

(56) References Cited

U.S. PATENT DOCUMENTS

| | | | |
|---|---|---|---|
| 2,606,903 | A | 8/1952 | Ruskin |
| 2,822,317 | A | 2/1958 | Gulesich et al. |
| 4,324,778 | A | 4/1982 | Davis |
| 4,578,390 | A | 3/1986 | Jensen et al. |
| 4,617,187 | A | 10/1986 | Okuyama et al. |
| 4,670,471 | A | 6/1987 | Clark |
| 4,686,235 | A | 8/1987 | Chang et al. |
| 4,707,354 | A | 11/1987 | Garlen et al. |
| 4,822,816 | A | 4/1989 | Markham |
| 4,861,783 | A | 8/1989 | Ackerman et al. |
| 4,968,716 | A | 11/1990 | Markham |
| 4,975,272 | A | 12/1990 | Voyt |
| 5,021,452 | A | 6/1991 | Labbe et al. |
| 5,070,085 | A | 12/1991 | Markham |
| 5,078,129 | A | 1/1992 | Kleinberg et al. |
| 5,238,683 | A | 8/1993 | Crystal |
| 5,281,196 | A | 1/1994 | Sultenfuss |
| 5,304,724 | A | 4/1994 | Newton |
| 5,612,208 | A | 3/1997 | Nakanishi et al. |
| 5,626,883 | A | 5/1997 | Paul |
| 5,824,693 | A | 10/1998 | Goldberg |
| 5,869,116 | A | 2/1999 | Yoo |
| 5,876,700 | A | 3/1999 | Boucher et al. |
| 5,989,521 | A | 11/1999 | Crystal |
| 6,011,067 | A | 1/2000 | Hersh |
| 6,228,347 | B1 | 5/2001 | Hersh |

(Continued)

FOREIGN PATENT DOCUMENTS

| | | |
|---|---|---|
| AU | 2002310351 A1 | 12/2002 |
| AU | 2002345757 A1 | 12/2002 |

(Continued)

OTHER PUBLICATIONS

Atkuri et al. "N-Acetylcysteine—a safe antidote for cysteine/glutathione deficiency" Current Opinion in Pharmacology 7(4):355-359 (2007).

Bergamini et al. "Azithromycin Decreases Glutathione-Stransferase T1 (GSTT1) and M1 (GSTM1) Expression and Activity in Cystic Fibrosis Airway Epithelial Cells" Pediatric Pulmonology 42(Suppl. 30):297 Abstract 269 (1 page) (2007).

Bergamini et al. "Effects of Azithromycin on Glutathione S-Transferases in Cystic Fibrosis Airway Cells" American Journal of Respiratory Cell and Molecular Biology 41(2):199-206 (2009).

Bishop et al. "A Pilot Study of the Effect of Inhaled Buffered Reduced Glutathione on the Clinical Status of Patients With Cystic Fibrosis" Chest 127(1):308-317 (2005).

(Continued)

*Primary Examiner* — Sergio Coffa
(74) *Attorney, Agent, or Firm* — Myers Bigel, P.A.

(57) ABSTRACT

The present invention provides compositions and formulations comprising glutathione with or without thiocyanate and methods of use thereof to treat diseases and disorders in mucosal/epithelial tissue.

36 Claims, 11 Drawing Sheets

(56) References Cited

U.S. PATENT DOCUMENTS

| | | |
|---|---|---|
| 6,312,734 B1 | 11/2001 | Kozhemyakin et al. |
| 6,492,328 B2 | 12/2002 | Lehrer et al. |
| 6,495,170 B1 | 12/2002 | Smit et al. |
| 6,603,012 B2 | 8/2003 | Belloni et al. |
| 6,655,385 B1 | 12/2003 | Curti et al. |
| 6,705,316 B2 | 3/2004 | Blythe et al. |
| 6,723,703 B2 | 4/2004 | Gaston et al. |
| 6,835,811 B1 | 12/2004 | Harbin et al. |
| 7,129,035 B2 | 10/2006 | Goldstein et al. |
| 7,179,791 B2 | 2/2007 | Stamler et al. |
| 7,572,251 B1 | 8/2009 | Davison et al. |
| 7,591,999 B2 | 9/2009 | Matsuyama et al. |
| 7,790,762 B2 | 9/2010 | Day et al. |
| 8,022,082 B2 | 9/2011 | Zierenberg |
| 8,067,441 B2 | 11/2011 | Gil et al. |
| 8,202,525 B2 | 6/2012 | Crain et al. |
| 8,211,628 B2 | 7/2012 | Thatte et al. |
| 8,217,006 B2 | 7/2012 | Stamler et al. |
| 8,217,033 B2 | 7/2012 | Gizurarson |
| 8,221,329 B2 | 7/2012 | Hartings et al. |
| 8,267,084 B2 | 9/2012 | Kwok |
| 8,327,843 B2 | 12/2012 | Warden et al. |
| 9,308,234 B2 * | 4/2016 | Arnold .................. A61P 11/00 |
| 10,406,200 B2 * | 9/2019 | Arnold .................. A61K 38/40 |
| 11,058,743 B2 * | 7/2021 | Arnold ................ A61K 9/0073 |
| 2003/0082101 A1 | 5/2003 | Taylor et al. |
| 2003/0099694 A1 | 5/2003 | Cevc et al. |
| 2003/0135201 A1 | 7/2003 | Gonnelli |
| 2003/0183226 A1 | 10/2003 | Brand et al. |
| 2004/0209235 A1 | 10/2004 | Goldstein et al. |
| 2004/0220262 A1 | 11/2004 | Hsu et al. |
| 2004/0229815 A1 | 11/2004 | Nagasawa et al. |
| 2005/0022806 A1 | 2/2005 | Beaumont et al. |
| 2006/0204557 A1 | 9/2006 | Gupta et al. |
| 2006/0228693 A1 | 10/2006 | Soll |
| 2006/0258599 A1 | 11/2006 | Childers |
| 2007/0027375 A1 | 2/2007 | Melker et al. |
| 2007/0049641 A1 | 3/2007 | Tirouvanziam et al. |
| 2007/0181444 A1 | 8/2007 | Bernstein et al. |
| 2008/0187901 A1 | 8/2008 | Doorschodt et al. |
| 2009/0010912 A1 | 1/2009 | Brands et al. |
| 2009/0068253 A1 | 3/2009 | Guilford |
| 2009/0092559 A1 | 4/2009 | Hoelz et al. |
| 2009/0145441 A1 | 6/2009 | Doshi et al. |
| 2009/0270310 A1 | 10/2009 | Whyte |
| 2009/0326861 A1 | 12/2009 | Langford et al. |
| 2010/0065048 A1 | 3/2010 | Mueller-Walz et al. |
| 2010/0074872 A1 | 3/2010 | Blaser et al. |
| 2010/0233295 A1 | 9/2010 | Gupta et al. |
| 2011/0011889 A1 | 1/2011 | Bonney et al. |
| 2011/0159048 A1 | 6/2011 | Crain et al. |
| 2011/0178152 A1 | 7/2011 | Savion et al. |
| 2011/0290256 A1 | 12/2011 | Sather et al. |
| 2012/0021071 A1 | 1/2012 | Bordeau et al. |
| 2012/0048271 A1 | 3/2012 | ODonnell et al. |
| 2012/0093947 A1 | 4/2012 | Britigan et al. |
| 2012/0165596 A1 | 6/2012 | Schmidt |
| 2012/0171239 A1 | 7/2012 | Mizel |
| 2012/0215278 A1 | 8/2012 | Penner |
| 2012/0264103 A1 | 10/2012 | Thatte et al. |
| 2012/0282591 A1 | 11/2012 | Thatte et al. |
| 2012/0291780 A1 | 11/2012 | Donovan et al. |
| 2012/0294822 A1 | 11/2012 | Russo et al. |
| 2013/0209578 A1 | 8/2013 | Borden et al. |
| 2015/0183747 A1 | 7/2015 | Chen et al. |

FOREIGN PATENT DOCUMENTS

| | | |
|---|---|---|
| AU | 2003302898 A1 | 6/2004 |
| AU | 2004315267 A1 | 8/2005 |
| AU | 2005302851 A1 | 5/2006 |
| AU | 2007224123 A1 | 9/2007 |
| AU | 2004315267 B2 | 1/2009 |
| AU | 2009205945 A1 | 7/2009 |
| AU | 2005305456 B2 | 5/2011 |
| AU | 2011224102 A1 | 10/2011 |
| AU | 2005302851 B2 | 2/2012 |
| AU | 2012201954 A1 | 4/2012 |
| CA | 2058793 A1 | 7/1992 |
| CA | 2339473 A1 | 2/2000 |
| CA | 2288540 | 5/2000 |
| CA | 2620123 A1 | 3/2007 |
| CA | 2644096 A1 | 9/2007 |
| CA | 2673478 A1 | 7/2008 |
| CA | 2678486 A1 | 8/2008 |
| CA | 2715638 A1 | 8/2009 |
| CA | 2785056 A1 | 7/2011 |
| CA | 2790337 A1 | 8/2011 |
| CA | 2620123 C | 11/2011 |
| CN | 1443081 A | 9/2003 |
| CN | 1921876 A | 2/2007 |
| CN | 101098622 A | 1/2008 |
| CN | 101313293 A | 11/2008 |
| CN | 101491495 A | 7/2009 |
| CN | 101098622 B | 8/2010 |
| CN | 101175499 B | 12/2010 |
| CN | 101987195 A | 3/2011 |
| CN | 102058593 A | 5/2011 |
| CN | 101313293 B | 6/2011 |
| CN | 101676023 B | 10/2011 |
| CN | 101491495 B | 6/2012 |
| CN | 101384288 B | 9/2012 |
| CN | 102100904 B | 4/2013 |
| DE | 2845484 A1 | 4/1980 |
| DE | 19935763 A1 | 2/2001 |
| DE | 102004035113 A1 | 2/2006 |
| DE | 60212837 T2 | 6/2007 |
| DE | 212011100034 U1 | 7/2012 |
| EP | 0326826 A1 | 8/1989 |
| EP | 0494405 A2 | 7/1992 |
| EP | 0494405 B1 | 10/1996 |
| EP | 0494405 B2 | 4/2000 |
| EP | 1250143 A2 | 10/2002 |
| EP | 0938331 B1 | 12/2002 |
| EP | 1282416 A2 | 2/2003 |
| EP | 1569511 A1 | 9/2005 |
| EP | 1701732 A2 | 9/2006 |
| EP | 1706025 A1 | 10/2006 |
| EP | 1711273 A1 | 10/2006 |
| EP | 1809101 A2 | 7/2007 |
| EP | 1996159 A2 | 12/2008 |
| EP | 1474158 B1 | 10/2009 |
| EP | 2139465 A1 | 1/2010 |
| EP | 1333823 B1 | 3/2010 |
| EP | 2189153 A2 | 5/2010 |
| EP | 2274619 A2 | 1/2011 |
| EP | 2349428 A1 | 8/2011 |
| EP | 2444121 A1 | 4/2012 |
| EP | 1909912 B1 | 6/2012 |
| EP | 1817006 B1 | 9/2012 |
| EP | 2139465 B1 | 9/2012 |
| EP | 2525777 A2 | 11/2012 |
| GB | 2080684 A | 2/1982 |
| JP | 2004514650 A | 5/2004 |
| JP | 2008519830 A | 6/2008 |
| JP | 2009528372 A | 8/2009 |
| JP | 4652664 B2 | 12/2010 |
| MX | 2008011187 A | 12/2008 |
| MX | 2009001855 A | 3/2009 |
| SG | 170063 A1 | 4/2011 |
| WO | 9731620 A2 | 9/1997 |
| WO | 9819694 A1 | 5/1998 |
| WO | 9952560 A1 | 10/1999 |
| WO | 0115692 A1 | 3/2001 |
| WO | 0137830 A1 | 5/2001 |
| WO | 0189520 A2 | 11/2001 |
| WO | 0232418 A1 | 4/2002 |
| WO | 02055018 A2 | 7/2002 |
| WO | 0189520 A3 | 9/2002 |
| WO | 02055018 A3 | 9/2002 |
| WO | 02100478 A2 | 12/2002 |
| WO | 02100478 A3 | 11/2003 |
| WO | 2004052098 A1 | 6/2004 |
| WO | 2004078211 A1 | 9/2004 |

(56) References Cited

FOREIGN PATENT DOCUMENTS

| | | |
|---|---|---|
| WO | 2005074903 A2 | 8/2005 |
| WO | 2005120457 A1 | 12/2005 |
| WO | 2005074903 A3 | 2/2006 |
| WO | 2006052133 A2 | 5/2006 |
| WO | 2006054304 A2 | 5/2006 |
| WO | 2006060120 A2 | 6/2006 |
| WO | 2006064271 A1 | 6/2006 |
| WO | 2006060120 A3 | 9/2006 |
| WO | 2006052133 A3 | 10/2006 |
| WO | 2007017146 A2 | 2/2007 |
| WO | 2007024876 A2 | 3/2007 |
| WO | 2006129304 A3 | 6/2007 |
| WO | 2007024876 A3 | 9/2007 |
| WO | 2007103194 A2 | 9/2007 |
| WO | 2007103194 A3 | 11/2007 |
| WO | 2007134180 A2 | 11/2007 |
| WO | 2008003688 A1 | 1/2008 |
| WO | 2008028092 A2 | 3/2008 |
| WO | 2008079350 A2 | 7/2008 |
| WO | 2008135984 A1 | 11/2008 |
| WO | 2009001884 A1 | 12/2008 |
| WO | 2009111681 A2 | 9/2009 |
| WO | 2010027387 A1 | 3/2010 |
| WO | 2010033292 A2 | 3/2010 |
| WO | 2010039201 A3 | 7/2010 |
| WO | 2010039202 A3 | 7/2010 |
| WO | 2010086530 A1 | 8/2010 |
| WO | 2011028875 A1 | 3/2011 |
| WO | 2011087755 A2 | 7/2011 |
| WO | 2011089604 A2 | 7/2011 |
| WO | 2011087755 A3 | 11/2011 |
| WO | 2012017367 A1 | 2/2012 |
| WO | 2011089604 A3 | 3/2012 |
| WO | 2012027603 A2 | 3/2012 |
| WO | 2012051426 A2 | 4/2012 |
| WO | 2012055886 A1 | 5/2012 |
| WO | 2012085582 A1 | 6/2012 |
| WO | 2012093192 A1 | 7/2012 |
| ZA | 200304678 B | 9/2004 |
| ZA | 200704147 B | 10/2008 |

OTHER PUBLICATIONS

Boyanova et al. "Coadministration of Probiotics With Antibiotics" Expert Reviews Anti-Infective Therapy 10(4):407-409 (2012).
Brechbuhl et al. "Glutathione transport is a unique function of the ATP-binding cassette protein ABCG2" Journal of Biological Chemistry 285(22):16582-16587 (2010).
Cantin, AM "Potential for antioxidant therapy of cystic fibrosis" Current Opinion in Pulmonary Medicine 10(6):531-536 (2004).
Cheluvappa et al. "Reactions of Pseudomonas aeruginosa pyocyanin with reduced glutathione" Acta Biochimica Polonica 55(3):571-580 (2008).
Cheng et al. "The PDZ domain protein CAL interacts with mGluR5a and modulates receptor expression" Journal of Neurochemistry 112(3):588-598 (2010).
Childers et al. "A new model of cystic fibrosis pathology: Lack of transport of glutathione and its thiocyanate conjugates" Medical Hypotheses 68(1):101-112 (2007).
Cidrap News "NIH launches first human trial of Ebola vaccine" www.cidrap.umn.edu/news-perspective/2003/11/nih-launches-first-human-trial-ebola-vaccine (2 pages) (2003).
Ciofu et al. "Respiratory bacterial infections in cystic fibrosis" Current Opinion in Pulmonary Medicine 19:251-258 (2013).
Clunes et al. "Cystic fibrosis: the mechanisms of pathogenesis of an inherited lung disorder" Drug Discovery Today 4(2):63-72 (2007).
Colombo et al. "Long-acting bronchodilators in cystic fibrosis" Current Opinion in Pulmonary Medicine 9:504-508 (2003).
Conner et al. "The lactoperoxidase system links anion transport to host defense in cystic fibrosis" Federation of European Biochemical Societies Letters 581:271-278 (2007).
Cursino et al. "Syngeric Interaction between Ascorbic Acid and Antibiotics against Pseudomonas aeruginosa" Brazilian Archives of Biology and Technology 48(3):379-384 (2005).

D'Orazio et al. "Extracellular Glutathione Decreases the Ability of Burkholderia cenocepacia to Penetrate into Epithelial Cells and to Induce an Inflammatory Response" PLOS One 7(10):e47550 (2012).
Dauletbaev et al. "A Phase II Study on Safety and Efficacy of High-Dose N-Acetylcysteine in Patients with Cystic Fibrosis" European Journal of Medical Research 14(8):352-358 (2009).
Day et al. "Role for Cystic Fibrosis Transmembrane Conductance Regulator Protein in a Glutathione Response to Bronchopulmonary Pseudomonas Infection" Infection and Immunity 72(4):2045-2051 (2004).
Day, Brian J. "Glutathione—A Radical Treatment for Cystic Fibrosis Lung Disease?" Chest 127(1):12-14 (2005).
De Villiers et al. "Optimizing MCPA (S-salt) activity with adjuvants" South African Journal of Plant and Soil 17(2):63-65 (2000).
Dewan "Advanced Drug Delivery Systems: Technologies and Global Markets" BCC Research Market Forecasting:1-278 (2011).
Dewan"Global Markets for Orphan Drugs" BCC Research Market Forecasting: 1-212 (2013).
Donnelly et al. "Defective Phagocytosis in Airways Disease" Chest 141(4):1055-1062 (2012).
Elsheikh et al. "Enhanced antigenicity leads to altered immunogenicity in sulfamethoxazole-hypersensitive patients with cystic fibrosis" Journal of Allergy and Clinical Immunology 127(6):1543-U348 (2011).
England et al. "Nasal pH measurement: a reliable and repeatable parameter" Clinical Otorhinolaryngology & Allied Sciences 24(1):67-68 (1999) (Abstract only).
Feuillet-Fieux et al. "Glutathione S-transferases Related to P. aeruginosa Lung Infection in Cystic Fibrosis Children: Preliminary Study" Clinical Biochemistry 42(1-2):57-63 (2009).
Fischer "Mechanisms and Function of DUOX in Epithella of the Lung" Antioxidants & Redox Signaling 11(10):2453-2465 (2009).
Fischer et al. "Clinical Evaluation of Ascoxal: A New Mucolytic Agent" Anesthesia & Analgesia 45(5):531-534 (1966).
Fitzpatrick et al. "Glutathione Oxidation Is Associated With Airway Macrophage Functional Impairment in Children With Severe Asthma" Pediatric Research 69(2):154-159 (2011).
Flamant et al. "Glutathione-S-transferase M1 M3, P1 and T1 polymorphisms and severity of lung disease in children with cystic fibrosis" Pharmacogenetics 14(5):295-301 (2004).
Gao et al. "Abnormal glutathione transport in cystic fibrosis airway epithella" American Journal of Physiology—Lung Cellular and Molecular Physiology 21:L113-L118 (1999).
Gao et al. "Synthetic chloride channel restores glutathione secretion in cystic fibrosis airway epithelia" American Journal of Physiology—Lung Cellular and Molecular Physiology 281(1):124-L30 (2001).
Geller "Aerosol Antibiotics in Cystic Fibrosis" Respiratory Care 54(5):658-670 (2009).
Gerson et al. "The Lactoperoxidase System Functions in Bacterial Clearance of Airways" Am J. Respir. Cell Mol. Biol. 22:665-671 (2000).
Gould et al. "Targeting maladaptive glutathione responses in lung disease" Biochemical Pharmacology 81(2):187-193 (2011).
Govindaraju et al. "Analysis of Glutathione in Rat Airway Surface Liquid by Capillary Zone Electrophoresis with Conductivity Detection" Journal of Chromatography B—Analytical Technologies in the Biomedical and Life Sciences 788(2):369-376 (2003).
Griese et al. "Improvement of alveolar glutathione and lung function but not oxidative state in cystic fibrosis" American Journal of Respiratory and Critical Care Medicine 169(7):822-828 (2004).
Griese et al. "Inhalation Treatment with Glutathione in Patients with Cystic Fibrosis" American Journal of Respiratory and Critical Care Medicine 188:83-89 (2013).
Grigoras et al. "Functional Characterization of the Saccharomyces cerevisiae ABC-transporter Yor1p Overexpressed in Plasma Membranes" Biochimica Biophysica Acta—Biomembranes 1778(1):68-78 (2008).
Gukasyan et al. "Glutathione and its transporters in ocular surface defense" The Ocular Surface 5(4):269-279 (2007).
Hartl et al. "Inhaled glutathione decreases PGE(2) and increases lymphocytes in cystic fibrosis lungs" Free Radical Biology and Medicine 39(4):463-472 (2005).

(56) References Cited

OTHER PUBLICATIONS

Havranova et al. "Release of glutathione from an oral dosage for the treatment of cystic fibrosis lung disease" Abstracts of Papers of the American Chemical Society 226:U249 (2003).
Hector et al. "Glutathione in Airway Neutrophils in Cystic Fibrosis" Pediatric Pulmonology 44(Suppl. 32) Abstract 420:359-360 (2009).
Hector et al. "Novel Method to Process Cystic Fibrosis Sputum for Determination of Oxidative State" Respiration 80(5):393-400 (2010).
Henrion-Caude et al. "Liver disease in pediatric patients with cystic fibrosis is associated with glutathione S-transferase P1 polymorphism" Hepatology 36(4):913-917 (2002).
Highsmith, Jackson "Biologic Therapeutic Drugs: Technologies and Global Markets" BCC Research Market Forecasting: 1-168 (2013).
Howell et al. "ATP hydrolysis by a CFTR domain: Pharmacology and effects of G551D mutation" Biochemical and Biophysical Research Communications 271(2):518-525 (2000).
Huang et al. "Airway Microbiota and Bronchial Hyperresponsiveness in Patients with Sub-optimally Controlled Asthma" Journal of Allergy and Clinical Immunology 127(2):372-381 (2011).
Hudson, Valerie "Differing Compartments of Intracellular Glutathione Have Differing Levels of Glutathione in Cystic Fibrosis" Medical Hypotheses 68(4):919-920 (2007).
Hudson, Valerie "Rethinking cystic fibrosis pathology: The critical role of abnormal reduced glutathione (GSH) transport caused by CFTR mutation" Free Radical Biology and Medicine 30(12):1440-1461 (2001).
Inci et al. "Prevention of primary graft dysfunction in lung transplantation by N-acetylcysteine after prolonged cold ischemia" Journal of Heart and Lung Transplantation 29(11):1293-1301 (2010).
Innis et al. "Choline-related supplements improve altered abnormal plasma methionine-homocysteine and glutathione status in children with cystic fibrosis" American Journal of Clinical Nutrition 85(3):702-708 (2007).
International Preliminary Report on Patentability corresponding to International Patent Application No. PCT/US2013/067307 (11 pages) (dated May 5, 2015).
International Search Report and the Written Opinion of the International Searching Authority corresponding to International Patent Application No. PCT/US2013/067307 (15 pages) (dated Feb. 12, 2014).
Jungas et al. "Glutathione levels and BAX activation during apoptosis due to oxidative stress in cells expressing wild-type and mutant cystic fibrosis transmembrane conductance regulator" Journal of Biological Chemistry 277(31):27912-27918 (2002).
Kariya et al. "A role for CFTR in the elevation of glutathione levels in the lung by oral glutathione administration" American Journal of Physiology—Lung Cellular and Molecular Physiology 292(6):L1590-L1597 (2007).
Kogan et al. "CFTR directly mediates nucleotide-regulated glutathione flux" The EMBO Journal 22(9):1981-1989 (2003).
Korytina, GF "Polymorphism of glutathione S-transferase M1 and P1 in patients with cystic fibrosis and chronic respiratory diseases" Russian Journal of Genetics 40(3):314-320 (2004).
Lands et al. "Lymphocyte Glutathione Levels in Children with Cystic Fibrosis" Chest 116:201-205 (1999).
Lands et al. "Total Plasma Antioxidant Capacity in Cystic Fibrosis" Pediatric Pulmonology 29(2):81-87 (2000).
Lands, Larry C. "Nutrition in pediatric lung disease" Paediatric Respiratory Reviews 8(4):305-312 (2007).
Laskowska-Klita et al. "Antioxidant status in erythrocytes of cystic fibrosis children" Acta Biochimica Polonica 48(1):283-285 (2001).
Lasry et al. "Inflammatory networks underlying colorectal cancer" Nature Immunology 17(3):230-240 (2016).
Lehr, Peggy "Global Markets for Asthma and COPD Drugs" BCC Research Market Forecasting: 1-159 (2012).
Li et al. "Spatiotemporal Coupling of cAMP Transporter to CFTR Chloride Channel Function in the Gut Epithelia" Cell 131(5):940-951 (2007).

Lima et al. "Cystic fibrosis transmembrane conductance regulator gene mutations and glutathione S-transferase null genotypes in cystic fibrosis patients in Brazil" Journal Brasileiro De Pneumologia 38(1):50-56 (2012).
Lothian et al. "Effect of whey protein to modulate immune response in children with atopic asthma" International Journal of Food Sciences and Nutrition 57(3-4):204-211 (2006).
Madarasi et al. "Antioxidant Status in Patients with Cystic Fibrosis" Annals of Nutrition and Metabolism 44(5-6):207-211 (2000).
Martin et al. "Host-microbe interactions in distal airways: relevance to chronic airway diseases" European Respiratory Review 24:78-91 (2015).
McKone et al. "Variants in the Glutamate-Cysteine-Ligase Gene Are Associated with Cystic Fibrosis Lung Disease" American Journal of Respiratory and Critical Care Medicine 174(4):415-419 (2006).
Moskwa et al. "A Novel Host Defense System of Airways Is Defective in Cystic Fibrosis" American Journal Respir. Crit. Care Med. 175:174-183 (2007).
Mullin et al. "Ebola outbreak rages on as drug development remains slow" FierceBiotech (3 pages) (2014).
Murphy, Timothy F. "The role of bacteria in airway inflammation in exacerbations of chronic obstructive pulmonary disease" Current Opinion in Infectious Diseases 19(3):225-230 (2006).
Nagavarapu "Pulmonary Drug Delivery Systems: Technologies and Global Markets" BCC Research Market Forecasting:1-222 (2012).
None et al. "Residual Gravimetric Method to Measure Nebulizer Output" Journal of Aerosol Medicine 17(1):63-72 (2004).
O'Brien, Peter J. "Peroxidases" Chemico-Biological Interactions 129:113-139 (2000).
Pedemonte et al. "Thiocyanate Transport in Resting and IL-4 Stimulated Human Bronchial Epithelial Cells: Role of Pendrin and Anion Channels" J Immunol 178:5144-5153 (2007).
Perez-Vilar et al. "Reevaluating Gel-Forming Mucins' Roles in Cystic Fibrosis Lung Disease" Free Radical Biology and Medicine 37(10):1564-1577 (2004).
Pitt, Bruce R. "CFTR trafficking and signaling in respiratory epithelium" American Journal of Physiology—Lung Cellular and Molecular Physiology 281(1):L13-L15 (2001).
Prousky, Jonathan "The Treatment of Pulmonary Diseases and Respiratory-Related Conditions with Inhaled (Nebulized or Aerosolized) Glutathione" eCAM 5(1):27-35 (2008).
Rada et al. "The Pseudomonas Toxin Pyocyanin Inhibits the Dual Oxidase-Based Antimicrobial System as It Imposes Oxidative Stress on Airway Epithelial Cells" J Immunol 181:4883-4893 (2008).
Remund et al. "Infections Relevant to Lung Transplantation" Proceedings of the American Thoracic Society 6:94-100 (2009).
Rogan et al. "Loss of Microbicidal Activity and Increased Formation of Biofilm Due to Decreased Lactoferrin Activity in Patients with Cystic Fibrosis" JID 190:1245-1253 (2004).
Roux et al. "*Mycobacterium abscessus*, pathogène émergent dans la mucoviscidose" Immuno-analyse et biologie specialisee 25(1):26-33 (2010) (English Abstract Only).
Schwarzer et al. "Organelle redox of CF and CFTR-corrected airway epithelia" Free Radical Biology and Medicine 43(2):300-316 (2007).
Schwarzer et al. "Oxidative Stress Caused by Pyocyanin Impairs CFFR Cl—Transport in Human Bronchial Epithelial Cells" Free Radical Biology and Medicine 45(12):1653-1662 (2008).
Sidlova et al. "Serum alpha-glutathione S-transferase as a sensitive marker of hepatocellular damage in patients with cystic fibrosis" Physiological Research 52(3):361-365 (2003).
Snyder et al. "Acute effects of aerosolized S-nitrosoglutathione in cystic fibrosis" American Journal of Respiratory and Critical Care Medicine 165(7):922-926 (2002).
Speich et al. "Epidemiology and Management of Infections after Lung Transplantation" Clinical Infectious Diseases 33(Suppl 1):S58-S65 (2001).
Szentpetery et al. "Functional Studies on the MRP1 Multidrug Transporter: Characterization of ABC-Signature Mutant Variants" Anticancer Research 24(2A):449-455 (2004).

(56) References Cited

OTHER PUBLICATIONS

Thomas et al. "Lactoperoxidase, peroxide, thiocyanate antimicrobial system: correlation of sulfhydryl oxidation with antimicrobial action" Infect. Immun. 20(2):456-463 (1978).

Thome et al. "Novel SIN-1 Reactive Intermediates Modulate Chloride Secretion Across Murine Airway Cells" Free Radical Biology and Medicine 35(6):662-675 (2003).

Tirouvanziam et al. "High-dose oral N-acetylcysteine, a glutathione prodrug, modulates inflammation in cystic fibrosis" Proceedings of the National Academy of Sciences of the United States of America 103(12):4628-4633 (2006).

Tournoud et al. "Structural equations to model relationships between pulmonary function, fatty acids and oxidation in cystic fibrosis" Scandinavian Journal of Clinical & Laboratory Investigation 69(1):36-44 (2009).

Vasu et al. "Evaluation of thiol-based antioxidant therapeutics in cystic fibrosis sputum: Focus on myeloperoxidase" Free Radical Research 45(2):165-176 (2011).

Velsor et al. "Antioxidant imbalance in the lungs of cystic fibrosis transmembrane conductance regulator protein mutant mice" American Journal of Physiology—Lung Cellular and Molecular Physiology 281(1):L31-L38 (2001).

Venglarik et al. "Hypochlorous acid alters bronchial epithelial cell membrane properties and prevention by extracellular glutathione" Journal of Applied Physiology 95(6):2444-2452 (2003).

Vilela et al. "High hydrostatic pressure enhances whey protein digestibility to generate whey peptides that improve glutathione status in CFTR-deficient lung epithelial cells" Molecular Nutrition & Food Research 50(11):1013-1029 (2006).

Vilela et al. "Inhibition of IL-8 release from CFTR-deficient lung epithelial cells following pre-treatment with fenretinide" International Immunopharmacology 6(11):1651-1664 (2006).

Virology Blog "Can Ebola virus infect via the skin?" www.virology.ws/2014/10/19/can-ebola-virus-infect-via-the-skin/ (6 pages) (downloaded on May 30, 2017).

Visca et al. "Improvement in clinical markers in CF patients using a reduced glutathione regimen: An uncontrolled, observational study" Journal of Cystic Fibrosis 7(5):433-436 (2008).

Wang et al. "Reversible silencing of CFTR chloride channels by glutathionylation" Journal of General Physiology 125(2):127-141 (2005).

Ward et al. "Lactoferrin and host defense" Biochem. Cell Biol. 80:95-102 (2002).

WebAssign "Lab 10—Electrochemical Cells" General Chemistry II Labs www.webassign.net/question_assets/ncsugenchem202labv1/lab_10/manual.html (8 pages) (downloaded on Jun. 8, 2017).

Willing et al. "Shifting the balance: antibiotic effects on host-microbiota mutualism" Nature Reviews Microbiology 9(4):233-243 (2011) (Abstract Only).

Wood et al. "Biomarkers of lipid peroxidation, airway inflammation and asthma" European Respiratory Journal 21(1):177-186 (2003).

Zhang et al. "Glutathione exhibits antibacterial activity and increases tetracycline efficacy against Pseudomonas aeruginosa" Science in China Series C-Life Sciences 52(6):501-505 (2009).

Zhao et al. "Decade-long bacterial community dynamics in cystic fibrosis airways" Proceedings of the National Academy of Sciences 109(15):5809-5814 (2012).

Caraher, et al., "The effect of recombinant human lactoferrin on growth and the antibiotic susceptibility of the cystic fibrosis pathogen Burkholderia cepacia complex when cultured planktonically or as biofilms", Journal of Antimicrobial Chemotherapy 60:546-554 (2007).

Carter, Chris J, "Pathogen and autoantigen homologous regions within the cystic fibrosis conductance regulator (CFTR) protein suggest an autoimmune treatable component of cystic fibrosis", Immunology and Medical Microbiology 62(2):197-214 (2011).

* cited by examiner

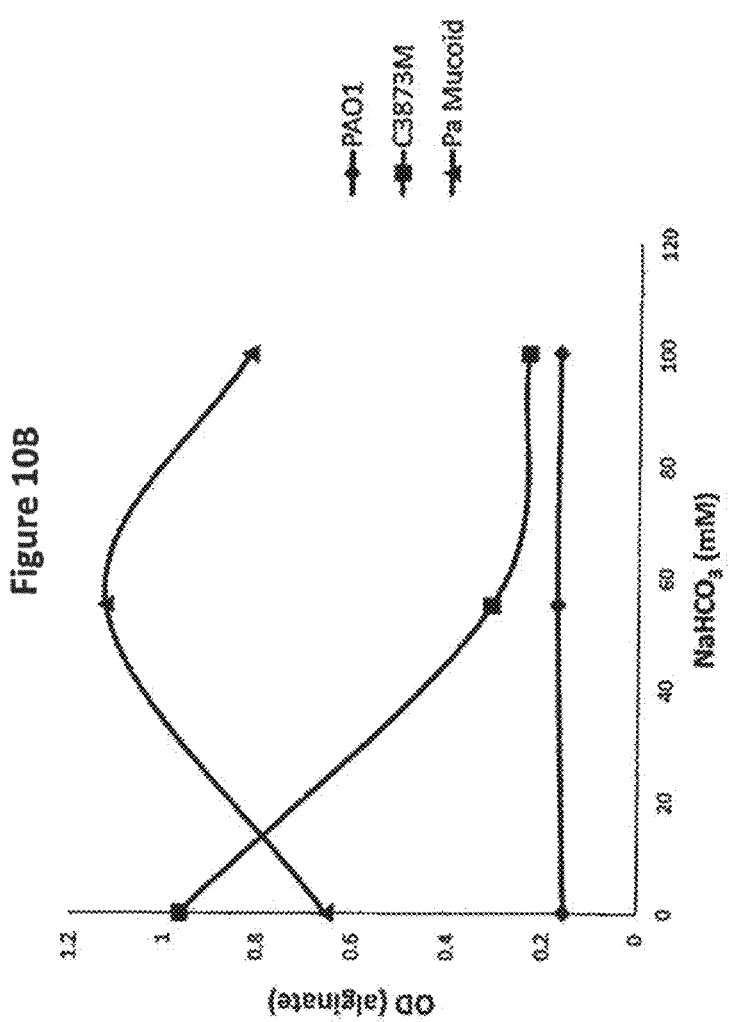

METHODS AND COMPOSITIONS FOR TREATING MUCOSAL TISSUE DISORDERS

STATEMENT OF PRIORITY

This application is a continuation application of, and claims priority to, U.S. application Ser. No. 16/529,204, filed Aug. 1, 2019 (allowed), which is a continuation of U.S. application Ser. No. 15/040,731, filed Feb. 10, 2016, now U.S. Pat. No. 10,406,200, issued Sep. 10, 2019, which is a continuation application of U.S. application Ser. No. 14/446,192, filed Jul. 29, 2014, now U.S. Pat. No. 9,308,234, issued Apr. 12, 2016, which is a continuation application under 35 U.S.C. § 111(a) of, and claims priority to, PCT Application No. PCT/US2013/067307, filed Oct. 29, 2013, which claims the benefit, under 35 U.S.C. § 119(e), of U.S. Provisional Application Ser. No. 61/719,804, filed Oct. 29, 2012, the entire contents of each of which are incorporated by reference herein.

FIELD OF THE INVENTION

The present invention generally relates to pharmaceutical compositions comprising glutathione, ascorbate and bicarbonate with or without thiocyanate and methods of use thereof to treat diseases and disorders in mucosal tissue.

BACKGROUND OF THE INVENTION

Mucosal surfaces (such as the oral cavity, eye, gastrointestinal, urogenital, and respiratory tracts) by design interface with potentially noxious environments. Protection against pathologic consequences of this direct environmental encounter is highly dependent on the exocrine secretions that bathe these exposed surfaces. These secretions provide the first line of defense against a variety of insults by providing physical barriers, mechanical clearance, and targeted pathogen neutralization without bystander damage of host tissues and consequent loss of function. To this end, these secretions deliver a variety of soluble factors including macromolecules, low molecular weight molecules and ions that work synergistically to maintain a healthy homeostasis by limiting host tissue exposure to pathogens and minimizing the host destructive consequences of inappropriate inflammatory responses and associated oxidative and nitrosative stresses.

For example, chronic lung and airway diseases are often characterized by a loss of homeostatic balance resulting in refractory infections and an organ-destructive host inflammatory response to exogenous stimuli. Pharmacologic doses of hormones such as glucocorticoids, other immunosuppressant therapies and antibiotics can provide some clinical relief, but are often inadequate. Alternatively, genetic information identifying specific protein dysfunction in disease suggests other therapeutic approaches for heritable diseases such as gene therapy for cystic fibrosis (CF). However, a need still exists for more adequate and effective treatment of such disorders.

The present invention overcomes previous shortcomings in the art by providing pharmaceutical compositions comprising glutathione, ascorbate and bicarbonate with or without thiocyanate and methods of use thereof to treat diseases and disorders in mucosal/epithelial tissue.

SUMMARY OF THE INVENTION

In one aspect, the present invention provides a composition comprising a) glutathione, a pharmaceutically-acceptable salt of glutathione, or a derivative or a prodrug thereof, b) an organic acid, a pharmaceutically-acceptable salt thereof (e.g., ascorbic acid), or a derivative or prodrug thereof, and c) a bicarbonate salt, such as sodium or potassium bicarbonate.

It is to be understood that in referring to a composition of this invention, wherein the terms glutathione, organic acid, or ascorbic acid are used without also referring to a pharmaceutically acceptable salt, derivative or prodrug thereof, such pharmaceutically acceptable salt, derivative or prodrug thereof is intended.

A pH adjusting agent can also be present in the compositions of this invention, if necessary or desired, to adjust the pH of the composition in some embodiments to be within a range from about 5 to about 9, in some embodiments to be within a range from about 6 to about 8, and in some embodiments to be within a range from about 6.5 to about 7.5. In one embodiment, the pH adjusting agent can be a bicarbonate salt.

It is to be understood that, as the relative amounts of glutathione and organic acid, such as ascorbic acid, can vary, the amount of bicarbonate salt can also vary. If glutathione and the organic acid are mixed with a bicarbonate salt, the acid functional groups will react with the bicarbonate to form the salts of the glutathione and the organic acid, and the bicarbonate will be acidified to form carbonic acid, with concomitant formation of water and evolution of carbon dioxide. Accordingly, if the formulation is prepared by mixing the acids with a bicarbonate salt, what is intended is that sufficient bicarbonate is added wherein the bicarbonate salt is present in a molar amount equal to the combined molar amount of the glutathione and the organic acid or in a molar excess of the combined molar amount of the glutathione and the organic acid. For example, the molar excess of the bicarbonate salt can be greater than 1.0 and less than about 1.5.

The weight ratios of the components of the compositions of this invention can vary over a wide range. Typically, the amount of each component is selected such that there is sufficient bicarbonate salt in the composition to bring the pH of the composition to the desired range, while also allowing for the bicarbonate salt to be present along with the glutathione and organic acid.

For example, the amount of (a) the glutathione, a pharmaceutically-acceptable salt of glutathione, or a derivative or a prodrug thereof can be from about 0.1 to about 95 percent by weight, the amount of (b) the organic acid, a pharmaceutically-acceptable salt thereof or a derivative or prodrug thereof can be from about 0.5 to about 60 percent by weight, and the weight of (c) the bicarbonate salt can be from about 1 to about 55 percent by weight. Within these ranges, the amount of (a) can be, for example, from about 52 to about 80 weight percent, (b) can be from about 3 to about 18 weight percent, and (c) can be from about 17 to about 30 weight percent.

In some embodiments, the compositions can further comprise from about 0.01% to about 5% by weight of a pharmaceutically-acceptable thiocyanate salt, such as from about 1% and about 2% by weight of a thiocyanate salt, while maintaining the weight ratios of the other components.

In some embodiments, the compositions can further include precursors to glutathione, such as methionine, cysteine and/or N-acetyl cysteine, in amounts from about 0.1% to about 10% by weight, while maintaining the weight ratios of the other components. In one aspect of this embodiment, glutathione precursors such as, methionine, cysteine and/or N-acetyl cysteine can be used in place of glutathione, rather than in addition to glutathione. In this aspect, the amount of the glutathione precursor in the composition can be that of glutathione.

In some embodiments, the present invention provides a pharmaceutical composition comprising about 0.1 to about 95 weight percent glutathione, a pharmaceutically acceptable salt thereof, a derivative thereof, an analogue thereof and/or a prodrug thereof, about 0.5 to about 60 weight percent organic acid, a pharmaceutically acceptable salt thereof, a derivative thereof, an analogue thereof and/or a prodrug thereof, and about 1 to about 55 weight percent bicarbonate. In some embodiments, this pharmaceutical composition can further comprise about 0.01 to about 20 weight percent thiocyanate, a pharmaceutically acceptable salt thereof, a derivative thereof, an analogue thereof and/or a prodrug thereof.

Also provided herein is a pharmaceutical composition comprising about 1 to about 14 weight percent glutathione, a pharmaceutically acceptable salt thereof, a derivative thereof, an analogue thereof and/or a prodrug thereof, about 0.1 to about 5 weight percent organic acid, a pharmaceutically acceptable salt thereof, a derivative thereof, an analogue thereof and/or a prodrug thereof, about 0.1 to about 10 weight percent bicarbonate and about 70 to about 85 weight percent water.

Further provided herein is a pharmaceutical composition comprising about 1 to about 14 weight percent glutathione, a pharmaceutically acceptable salt thereof, a derivative thereof, an analogue thereof and/or a prodrug thereof, about 0.1 to about 5 weight percent organic acid, a pharmaceutically acceptable salt thereof, a derivative thereof, an analogue thereof and/or a prodrug thereof, about 0.1 to about 10 weight percent bicarbonate, about 0.01 to about 2 weight percent thiocyanate, a pharmaceutically acceptable salt thereof, a derivative thereof, an analogue thereof and/or a prodrug thereof and about 15 to about 85 weight percent water.

The present invention additionally provides a pharmaceutical composition comprising glutathione, a pharmaceutically acceptable salt thereof, a derivative thereof, an analogue thereof and/or a prodrug thereof, ascorbic acid, a pharmaceutically acceptable salt thereof, a derivative thereof, an analogue thereof and/or a prodrug thereof, and sodium bicarbonate in a weight to weight to weight ratio of about 1.5:1:0.8 to 95:1:4.

Further provided herein is a pharmaceutical composition comprising glutathione, a pharmaceutically acceptable salt thereof, a derivative thereof, an analogue thereof and/or a prodrug thereof, ascorbic acid, a pharmaceutically acceptable salt thereof, a derivative thereof, an analogue thereof and/or a prodrug thereof, sodium bicarbonate, and thiocyanate, a pharmaceutically acceptable salt thereof, a derivative thereof, an analogue thereof and/or a prodrug thereof in a weight to weight to weight to weight ratio of about 1:90:100:1 to 1000:10:40:1.

Additionally provided herein is a pharmaceutical composition comprising glutathione, a pharmaceutically acceptable salt thereof, a derivative thereof, an analogue thereof and/or a prodrug thereof, an organic acid, a pharmaceutically acceptable salt thereof, a derivative thereof, an analogue thereof and/or a prodrug thereof, a bicarbonate and water in a weight to weight to weight to weight ratio of about 1:60:60:600 to about 100:1:1:20.

The present invention also provides a pharmaceutical composition comprising glutathione, a pharmaceutically acceptable salt thereof, a derivative thereof, an analogue thereof and/or a prodrug thereof, an organic acid, a pharmaceutically acceptable salt thereof, a derivative thereof, an analogue thereof and/or a prodrug thereof, a bicarbonate, thiocyanate, a pharmaceutically acceptable salt thereof, a derivative thereof, an analogue thereof and/or a prodrug thereof and water in a weight to weight to weight to weight to weight ratio of about 1:100:100:1:1,000 to about 1,000:10:40:1:250.

In further embodiments of the pharmaceutical compositions recited above, the compositions can include a pH adjusting agent, which can be, but is not limited to, citric acid, sodium citrate, sodium bicarbonate, dibasic sodium phosphate, magnesium oxide, calcium carbonate and magnesium hydroxide, an acetate buffer, a citrate buffer, a phosphate buffer, a lactic acid buffer, a borate buffer and any combination thereof.

In further embodiments, the present invention provides a pharmaceutical composition comprising glutathione, ascorbic acid and sodium bicarbonate in a weight to weight to weight ratio of about 4.13:1:1.74 to 20:1:4.57.

Also provided herein is a pharmaceutical composition comprising glutathione, ascorbic acid, sodium bicarbonate and water in a weight to weight to weight to weight ratio of about 4.13:1:1.73:16.39 to 19.96:1:4.55:88.18.

The present invention additionally provides a pharmaceutical composition comprising about 52 to about 78 weight percent glutathione, about 3.5 to about 18 weight percent ascorbic acid, about 17 to about 30 weight percent sodium bicarbonate, and about 0.2 to about 1.0 weight percent thiocyanate.

Additional embodiments of this invention include a pharmaceutical composition comprising about 52 to about 80 weight percent glutathione, about 3 to about 18 weight percent ascorbic acid or about 17 to about 30 weight percent sodium bicarbonate.

Furthermore, the present invention provides a pharmaceutical composition comprising glutathione, ascorbic acid, sodium bicarbonate and thiocyanate in a weight to weight to weight to weight ratio of about 220:11.11:50.78:1 to 220:53.78:93.33:1.

Also provided herein is a pharmaceutical composition comprising about 17 to about 19 weight percent glutathione, about 0.5 to about 4.5 weight percent ascorbic acid, about 4 to about 8 weight percent sodium bicarbonate, about 0.05 to about 0.5 weight percent thiocyanate and about 70 to about 81 weight percent water.

Also provided herein is a pharmaceutical composition comprising about 17 to about 20 weight percent glutathione, about 0.5 to about 5 weight percent ascorbic acid, about 4 to about 8 weight percent sodium bicarbonate and about 65 to about 81 weight percent water. In addition, the present provides a pharmaceutical composition comprising glutathione, ascorbic acid, sodium bicarbonate, thiocyanate and water in a weight to weight to weight to weight to weight ratio of about 220:11:50:1:975 to 220:53:93:1:900.

A further aspect of the invention is a pharmaceutical composition comprising 72.92% by weight glutathione, 4.86% by weight ascorbic acid, and 22.22% sodium bicarbonate.

Also provided herein is a pharmaceutical composition comprising 53.12% by weight glutathione, 17.14% by weight ascorbic acid, and 29.74% by weight sodium bicarbonate.

The present invention further provides a pharmaceutical composition comprising 13.96% by weight glutathione, 0.93% by weight ascorbic acid, 4.25% by weight sodium bicarbonate, and 80.86% water.

A pharmaceutical composition is also provided herein, comprising 13.51% by weight glutathione, 4.36% by weight ascorbic acid, 7.57% by weight sodium bicarbonate, and 74.56% by weight water.

The present invention additionally provides a pharmaceutical composition comprising 78.22% by weight glutathione, 3.91% by weight ascorbic acid, and 17.87% by weight sodium bicarbonate.

Further provided herein is a pharmaceutical composition comprising 60.17% by weight glutathione, 14.56% by weight ascorbic acid, and 25.27% sodium bicarbonate.

An additional embodiment of this invention provides a pharmaceutical composition comprising 18.36% by weight glutathione, 0.92% by weight ascorbic acid, 4.19% by weight sodium bicarbonate, and 76.53% water.

Furthermore, the present invention provides a pharmaceutical composition comprising 17.77% by weight glutathione, 4.3% by weight ascorbic acid, 7.46% by weight sodium bicarbonate, and 70.47% by weight water.

Additionally provided herein is a pharmaceutical composition comprising 0.78% by weight glutathione, 46.56% by weight ascorbic acid, 52.65% by weight sodium bicarbonate.

In yet further embodiments, the present invention provides a pharmaceutical composition comprising 0.13% by weight glutathione, 8.12% by weight ascorbic acid, 9.18% by weight sodium bicarbonate, and 82.57% by weight water.

A further aspect of the invention is a pharmaceutical composition comprising 72.92% by weight glutathione, 4.86% by weight ascorbic acid, and 22.22% sodium bicarbonate.

Also provided herein is a pharmaceutical composition comprising 53.12% by weight glutathione, 17.14% by weight ascorbic acid, and 29.74% sodium bicarbonate.

The present invention further provides a pharmaceutical composition comprising 13.96% by weight glutathione, 0.93% by weight ascorbic acid, 4.25% by weight sodium bicarbonate, and 80.86% water.

A pharmaceutical composition is also provided herein, comprising 13.51% by weight glutathione, 4.36% by weight ascorbic acid, 7.57% by weight sodium bicarbonate, and 74.56% by weight water.

The present invention additionally provides a pharmaceutical composition comprising 78.22% by weight glutathione, 3.91% by weight ascorbic acid, and 17.87% by weight sodium bicarbonate.

Further provided herein is a pharmaceutical composition comprising 60.17% by weight glutathione, 14.56% by weight ascorbic acid, and 25.27% sodium bicarbonate.

An additional embodiment of this invention provides a pharmaceutical composition comprising 18.36% by weight glutathione, 0.92% by weight ascorbic acid, 4.19% by weight sodium bicarbonate, and 76.53% water.

Furthermore, the present invention provides a pharmaceutical composition comprising 17.77% by weight glutathione, 4.3% by weight ascorbic acid, 7.46% by weight sodium bicarbonate, and 70.47% by weight water.

Additionally provided herein is a pharmaceutical composition comprising 0.78% by weight glutathione, 46.56% by weight ascorbic acid, 52.65% by weight sodium bicarbonate.

In yet further embodiments, the present invention provides a pharmaceutical composition comprising 0.13% by weight glutathione, 8.12% by weight ascorbic acid, 9.18% by weight sodium bicarbonate, and 82.57% by weight water.

A composition of this invention can be present, for example, as a solid formulation, such as a particle formulation, or as a solution. When in a particle formulation, the particles can be mixed with gases, or liquid propellants, for use in inhalation therapy. Other solid formulations include formulations for oral administration, buccal administration or colonic administration, and suppositories for rectal or vaginal administration. Exemplary formulations include, but are not limited to, the following: eye drops, nebulizers, topical gels and ointments, dry powders, particles, sprays, liquids, anesthetic machines or vaporizers, autoinjectors, intrauterine devices, respimats, liniments, liposomes, lotions, formulations for intramuscular, intrathecal, or subcutaneous injection, douches, infusions, and face masks.

In solution form, the formulations can be in the form of sprays for intranasal administration, formulations for use in nebulizers, and formulations for rectal administration, such as enemas and colonics. Solutions that include water-miscible organic solvents, such as propylene glycol and/or glycerol, and other components normally found in vaginal and rectal lubricants, can also be used. Regardless of the solvents used, the solvent is typically present in a weight ratio of from about 15 to about 85 percent by weight, relative to the weight of the solids, and, more typically, is from about 50 to about 85% by weight.

The compositions and/or formulations of this invention can be used to treat disorders associated with a mucosal membrane, by delivering the compositions and/or formulations to the mucosal membrane(s) to be treated. In some embodiments, the mucosal membrane can be in or near the lungs, such as the deep lung (alveolar region), and in other embodiments, the mucosal membrane(s) can be in or near one or more of the eyes, mouth, nose, rectum, and/or vagina.

In still further embodiments, the composition of this invention can further comprise, and/or the composition can be administered in combination or in alternation with, one or more therapeutic agents. In some embodiments, the composition of this invention and therapeutic agent(s) are directed to the same locus in the same formulation, and in other embodiments, the composition can be administered via one pathway, and the therapeutic agent(s) can be administered via a different pathway.

In some embodiments, the therapeutic agent(s) treat the disorder for which they are administered, but cause certain side effects, such as a drying of a mucosal membrane that results in discomfort and/or injury, which side effects can be addressed by administering a composition of this invention to a subject in need thereof.

In other embodiments, the therapeutic agent and composition of this invention both treat the underlying disorder, though via different means, such that an additive or synergistic effect can be achieved. As a result, in some aspects of this embodiment, a lower dose of the therapeutic agent can be effective, which lower dose can result in fewer side effects, or provide other benefits to the subject. By lower dose is meant a dose that is less than a dose that would typically be administered in the absence of administration of a composition of this invention.

In embodiments of this invention that comprise a therapeutic agent, the resulting new formulation can provide a new application for the therapeutic agent, enhance the efficacy of the therapeutic agent, reduce unwanted side effects associated with the therapeutic agent, and/or reduce the dose of the therapeutic agent.

Exemplary therapeutic agents of this invention include, but are not limited to, monoclonal antibodies; immunomodulatory agents, including agents that cause T and B cell activation, proliferation, and/or maturation; agents that bring about innate immune system activation, proliferation and/or maturation (e.g., JNK, MAPK, ERK, NK kappa B pathway agonists or antagonists, and monocyte, neutrophil, or macrophage agonists or antagonists); matrix metalloproteinase inhibitors; heat shock protein agonists or antagonists; alpha synuclein inhibitors; chelating agents; diuretics; alpha 1 antitrypsin modulators; purinoceptor agonists or antagonists; cyclooxygenase 2 inhibitors; DNA gyrase inhibitors; natural killer cell and natural killer T cell agonists or antagonists; cathepsin class agonists or antagonists; antioxidant therapy agents; rho-associated kinase inhibitors; myosin inhibitors; phosphatidylinositol 3 kinase inhibitors and related molecules; nitric oxide synthase agonists or antagonists; nitric oxide agonists or antagonists; ion channel function or trafficking modulators; surfactants, in particular, lung surfactants; cannabinoid receptor modulators; complement system inhibitors; IgE receptor antagonists; G protein-coupled receptor agonists or antagonists; chemokines; chemokine receptor agonists or antagonists; cytokines; cytokine receptor agonists or antagonists; arachidonic acid agonists or antagonists; inflammation mediators; STAT6 inhibitors; histamine or leukotriene agonists or antagonists; calcineurin agonists or antagonists; and ant combination thereof.

In some embodiments wherein the composition of this invention includes one or more therapeutic agent, the composition can be used to treat a mucosal disease or disorder a pulmonary disease or disorder, an autoimmune disease or disorder (e.g., multiple sclerosis, Crohn's disease, ulcerative colitis, lupus, inflammatory bowel syndrome, irritable bowel syndrome, etc.), an infectious disease (e.g., HIV infection), a neurodegenerative disease or disorder (e.g., Alzheimer's disease), and the like, singly or in any combination.

In some embodiments of this invention, the one or more therapeutic agents can be present with the glutathione, organic acid and bicarbonate in a single formulation, and in other embodiments, the one or more therapeutic agents can be present in a first formulation and the glutathione, organic acid and bicarbonate can be present in a second formulation that is separate from the first formulation. As such, the compositions and formulations can be used in combination or 'kit' therapies. As one non-limiting example, the formulation with the therapeutic agent can be present in oral, injectable, and/or inhaled forms, and the glutathione, organic acid and bicarbonate can be present in an inhaled (e.g., pulmonary or intranasal) formulation.

While not wishing to be bound by any particular theory, in some embodiments of this invention, the formulations disclosed herein can be effective in achieving and/or maintaining a normal lung mucosa, or at least a more normal lung mucosa, which is an important factor in maintaining lung health. Drugs administered to the lungs are often associated with certain side effects, in some cases because of dosage, and in other cases because they damage the lung tissue. In some embodiments, therapeutic agents combined with the formulations disclosed herein are effective at lower doses, and at such lower doses, the incidence of side effects can be reduced. For example, one can decrease inhaled corticosteroid (ICS) dosing and accordingly, reduce the risk of pneumonia in a subject with chronic obstructive pulmonary disease (COPD), and one can reduce the dose of β-agonists and other bronchodilators to reduce the risk of death in asthma patients.

In some embodiments, wherein the therapeutic agent interacts unfavorably with lung tissue, the formulation of this invention can be administered to restore homeostasis to the lung tissue, and thus minimize or eliminate side effects and/or damage caused by the therapeutic agent.

The present invention also provides a method of treating an airway disorder or disease in a subject in need thereof, comprising delivering to the subject an effective amount of a composition of this invention, optionally in combination with a steroid and/or bronchodilator, such as a beta$_2$-agonist.

Furthermore, the present invention provides a method of treating an infection in the airway of a subject in need thereof, comprising delivering to the subject an effective amount of a composition of this invention, optionally in combination with one or more antibiotics. The antibiotics can be administered locally to the lungs and/or systemically.

Inflammation in the airway of a subject in need thereof can be treated by delivering to the subject an effective amount of a composition of this invention.

In addition to providing methods of treatment, the compositions described herein can be used to provide prevention and/or amelioration of various diseases and disorders. For example, there are a number of smoking related disorders, such as COPD, cardiac disorders, urinary tract disorders including cancer, gastrointestinal disorders such as peptic ulcer disease, and the like, which can be prevented, at least to some extent, by administering a composition of this invention prophylactically. Prophylactic administration of a composition of this invention to mucosal tissue can establish and/or maintain homeostasis in the mucosal tissue, to prevent and/or ameliorate damage or other pathological harm to the tissue.

A composition of this invention can also be administered prophylactically during cold and flu season, to prevent, ameliorate or reduce the severity of a viral infection in the lungs and other mucosal membranes. This is particularly true of medical workers, who are exposed to a variety of infectious agents, including viruses, bacteria, fungi, and the like. Maintenance of homeostasis in mucosal tissue helps to protect against infectious diseases, so prophylactic administration is particularly useful for such workers.

A subject in a polluted or contaminated air environment can be protected against the effects of air pollution or contamination on the lungs and other mucosal membranes by prophylactically administering a composition of this invention to the mucosal membrane(s) to be protected. For example, medical professionals, soldiers, fire fighters, factory workers, and the like that work in an air-polluted and/or contaminated environment (e.g., radon contamination) can benefit from prophylactic administration of the compositions of this invention.

Prophylactic administration of a composition of this invention can also be useful when a subject is exposed to dry air and/or other airway-irritating environments, such as those experienced when flying.

Yet further embodiments of this invention include the use of a composition of this invention in the manufacture of a medicament for treating a mucosal tissue disease or disorder, treating an infection an/or a disease or disorder caused by infection by a pathogen in mucosal tissue and/or treating inflammation in mucosal tissue in a subject.

Also provided herein is the use of a composition of this invention in the manufacture or preparation of a medicament for treating a disorder of the mouth, treating a pulmonary or airway disorder or disease, treating a pulmonary or airway disorder or disease, wherein the pulmonary or airway disorder is an inflammatory disorder, treating a disorder of the eye, treating a disorder of the central nervous system, treating a nasal disorder, treating a gastrointestinal disorder, treating a urinary tract disorder, renal disorder, and/or disorder in the urogenital tract, treating a disorder of the circulatory system, restoring homeostasis to and/or maintaining homeostasis in a mucosal membrane of a subject with cystic fibrosis or a lung transplant, reducing dryness in a mucosal membrane of a subject treated with an anticancer agent that causes dryness in the mucosal membrane, preserving an organ for organ transplantation, preventing a lung disease or disorder caused by infection by a pathogen, preventing and/or reducing the symptoms of a gastrointestinal disorder with an inflammatory component, and restoring homeostasis to or maintaining homeostasis in a vaginal and/or rectal mucosal membrane, singly or in any combination.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

FIGS. 10A-B. Influences of bicarbonate on alginate production by different strains of *P. aeruginosa* under a 5% $CO_2$ atmosphere. Alginate production of selected strains of *P. aeruginosa* surface grown in a $CO_2$ incubator was quantitatively determined by a colorimetric assay. Previous studies suggested that clinical isolates of mucoidy *P. aeruginosa* had exaggerated mucoidy production when grown in 5% $CO_2$ atmosphere (FIG. 10A, left plate) vs. ambient atmosphere (FIG. 10A, right plate). In contrast, strain PAO1 does not produce mucoidy colonies, but Pa Mucoid laboratory derived from PAO1 does. Colonies from Pa Mucoid however were not affected by 5% $CO_2$ compared to ambient atmosphere. These three strains were then tested for their ability to make alginate under an atmosphere of 5% $CO_2$ with increasing concentrations of $NaHCO_3$ (FIG. 10B). As can be seen, PAO1 failed to make alginate under any of the test conditions. The clinical isolate (C3873M) made significant quantities of alginate and this alginate production was inhibited by bicarbonate. In contrast alginate production by the laboratory strain not only was not suppressed, but was significantly enhanced by bicarbonate. These data suggest that alginate production provides an important barrier to reactive oxygen species that would be associated with the exaggerated inflammatory response in the CF airway. These data also suggest that mucoidy properties are important to bacterial tolerance of the RNI associated with nitrate respiration. This would indicate that raising the levels of bicarbonate in the bicarbonate-deficient airway surface liquid of the CF lung could shut down an important defense mechanism of CF pathogens.

DETAILED DESCRIPTION OF THE INVENTION

Figure 1:
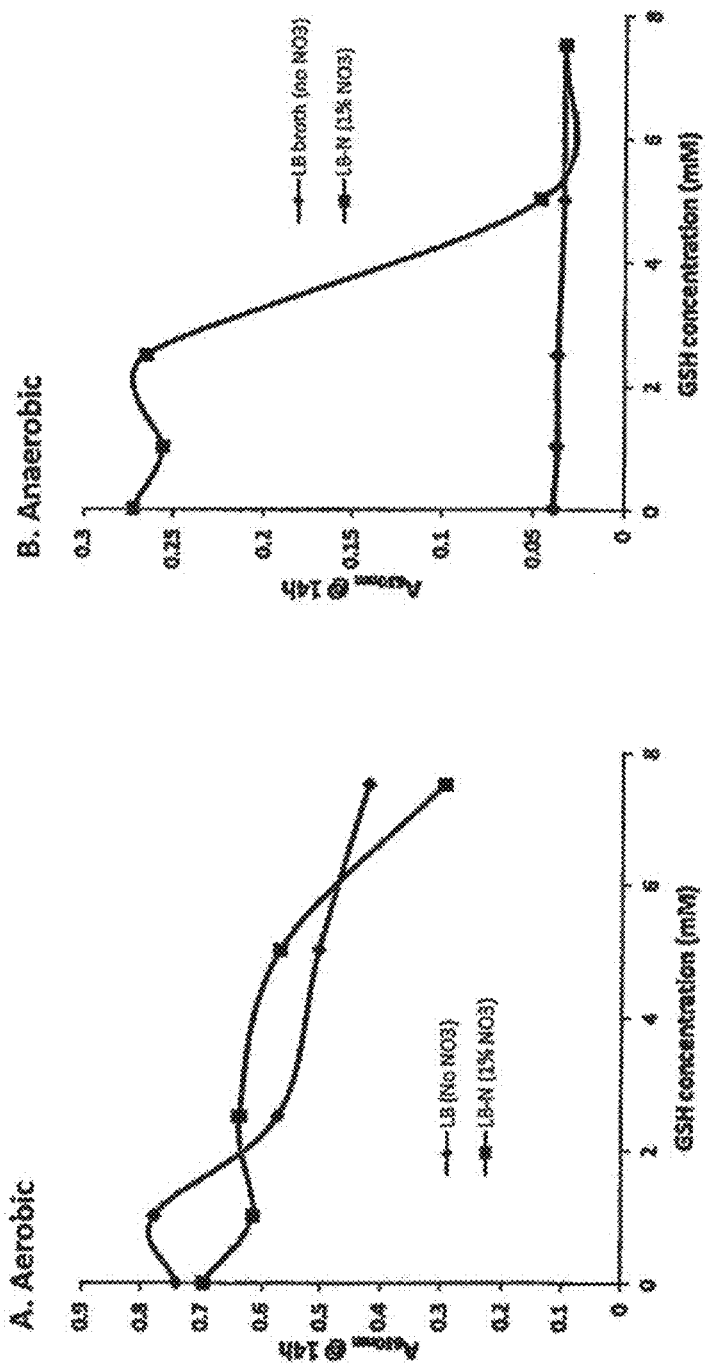
FIG. 1. Glutathione inhibits nitrate dependent growth. *Pseudomonas aeruginosa* strain PAO1 is capable of growing in the absence of oxygen using nitrate for respiration. The presence of nitrate to 1% in Lauria Bertani (LB) broth had no discernible effect on growth in ambient atmosphere and this strain was incapable of growth in LB broth in an anaerobic atmosphere of 5% $CO_2$-10% $H_2$-85% $N_2$ without supplementation. The studies presented in FIG. 1 examine whether glutathione influences the growth of PAO1 either in the presence or absence of nitrate under either ambient (aerobic) or anaerobic atmospheres. There were no discernible differences between the influences of glutathione on the aerobic growth of PAO1 either in the presence or absence of 1% nitrate in LB broth (Panel A). There was a trend toward reduced growth yield at 14 h with increasing concentrations of glutathione that reached significance with 7.5 mM glutathione consistent with the reducing potential of the glutathione limiting oxygen dependent growth. In contrast, there was total inhibition of nitrate dependent growth (Panel B) with the 5 and 7.5 mM concentrations of glutathione and no discernible effects with 2.5 mM or less.
Figure 2:
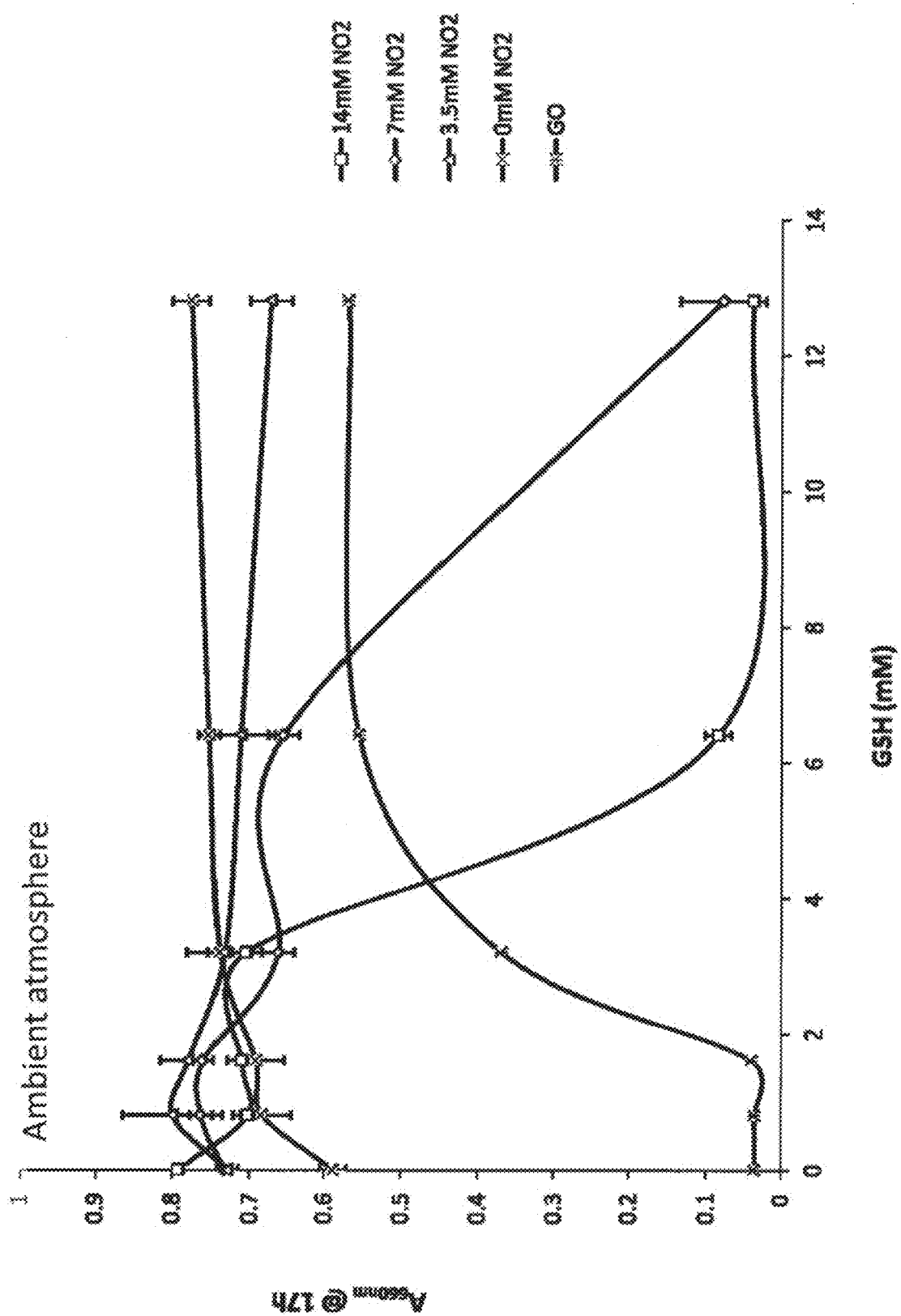
FIG. 2. Glutathione potentiation of nitrite mediated inhibition of PAO1 while blocking $H_2O_2$ mediated inhibition. Previous studies indicated that with nitrate ($NO_3$) dependent respiration that the resulting products of nitrite ($NO_2$) and nitric oxide (NO) were responsible for inhibition of bacterial growth. It was further suggested that oxygen dependent growth can proceed in the presence of nitrate, but was inhibited by millimolar concentrations of either nitrite or nitric oxide. The fact that glutathione was inhibitory for oxygen depleted, nitrate-dependent growth, but not for aerobic growth in the presence of nitrate (FIG. 1), suggested the inhibitory effects of glutathione were dependent on nitrate reduction, suggesting that the inhibitory effects of nitrite and nitric oxide previously observed might be potentiated by glutathione. To test this possibility, reduced glutathione was titrated vs. increasing concentrations of $KNO_2$ in either trypticase soy broth (TSB) in ambient atmosphere or in trypticase soy broth with nitrate (TSBN) (1% $KNO_3$) under anaerobic atmosphere. Reduced glutathione resulted in a slight, but significant, concentration-dependent increase in growth yield in the absence of nitrite. In these experiments, nitrite to 14 mM had no discernible inhibition on aerobic growth in the absence of glutathione. There was synergistic, concentration-dependent inhibition between glutathione and nitrite, resulting in significant inhibition with 6.4 mM GSH and 14 mM $KNO_2$ and with 12.8 mM GSH and 7 mM $KNO_2$. In contrast, increasing the concentration of GSH protected PAO1 from the growth inhibiting effects of glucose oxidase, consistent with reduced glutathione dependent bacterial peroxidase activity. Nitrate was required for PAO1 growth in TSB under anaerobic atmosphere and the addition of $KNO_2$ at the concentrations tested in these experiments resulted in significant inhibition even in the absence of glutathione (not shown). There was, however, further inhibition evident with increasing concentrations of GSH in the presence of nitrite concentrations that did not result in total inhibition by themselves.
Figure 3:
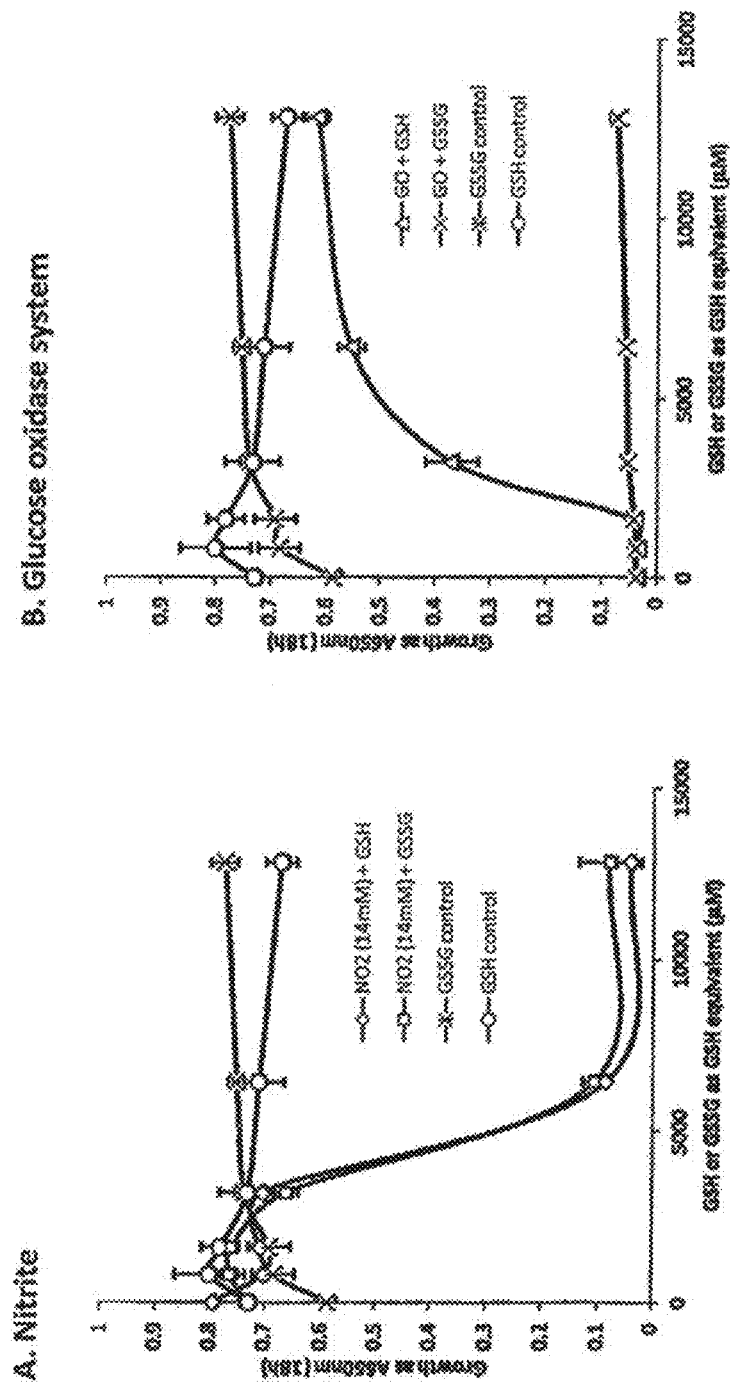
FIG. 3. Glutathione potentiation of nitrite inhibition is independent of the redox state of the glutathione. These studies examined the question of the importance of the redox state of glutathione to its contributions to the inhibition by RNI and to the blocking of the glucose oxidase antimicrobial effects. Glutathione in either its reduced (GSH) or oxidized (GSSG) form was titrated in the presence or absence of 14 mM nitrite in TSB and PAO1 was grown in ambient atmosphere. Both GSH and GSSG at molar equivalency resulted in inhibition of PAO1 growth in the presence of nitrite (Panel A). In contrast, GSH but not GSSG protected PAO1 from inhibition with the glucose oxidase system (Panel B). Additional studies indicated that growth inhibition of PAO1 by exogenous $H_2O_2$ was also blocked by 14 mM GSH, suggesting a direct effect on $H_2O_2$ activity and not the indirect blocking of the enzymatic activity of glucose oxidase. These data suggest that the oxidized form of glutathione would be efficacious in inhibiting nitrate dependent growth without the possible adverse consequence of protecting the bacteria from host innate defenses dependent upon $H_2O_2$ antibacterial activity.
Figure 4:
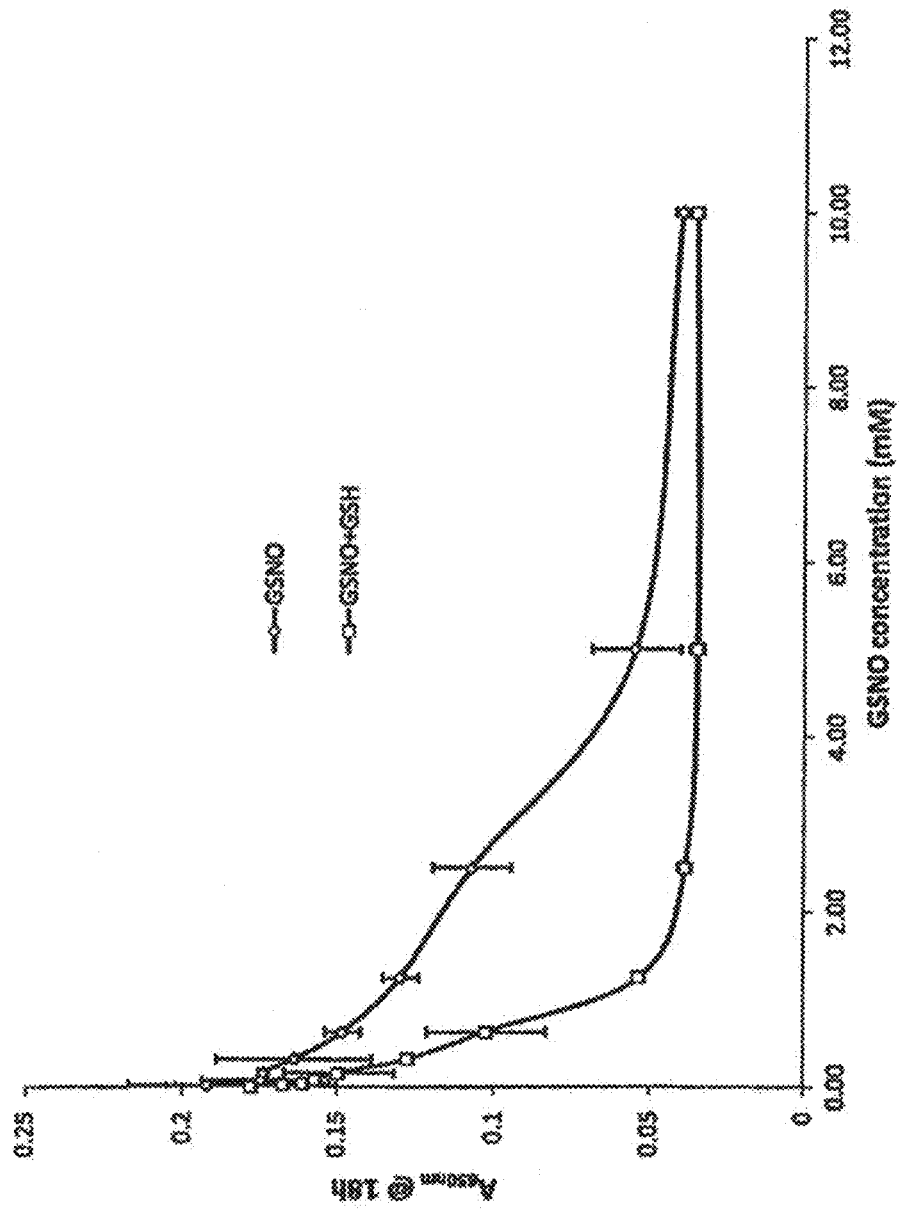
FIG. 4. Glutathione enhances S-nitrosoglutathione inhibition of nitrate dependent growth of PAO1. Previous studies suggested that the nitric oxide donor S-nitrosoglutathione (GSNO) was capable of inhibiting nitrate-dependent growth of *P. aeruginosa*. This raised the possibility that the potentiating effects of glutathione on the antimicrobial activity of nitrate metabolites were the result of generation of the more active nitrosoglutathione specie. This would suggest the possibility that glutathione would have little additional effect on the activity of authentic nitrosoglutathione. To examine this possibility, S-nitrosoglutathione (Sigma) was tested for influence on growth of PAO1 in TSBN (1% $KNO_3$) with and without 6.4 mM glutathione. There was a concentration dependent inhibition of PAO1 growth as determined by bacterial density ($A_{\square 650\ nm}$) at 18 h. This inhibition was significantly enhanced in the presence of glutathione with an exponential decrease in the concentration of GSNO necessary for total inhibition of growth achieved at 18 h.
Figure 5:
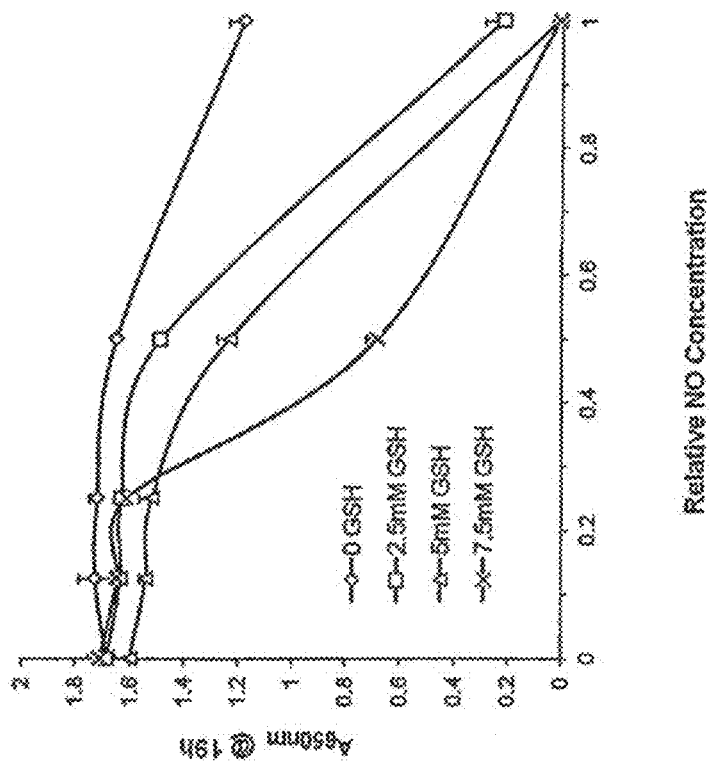
FIG. 5. Glutathione enhances the inhibitory activity of NO gas of PAO1 aerobic growth. Previous studies demonstrated that NO gas was capable of inhibiting PAO1 aerobic growth and suggested that NO was the ultimate product of nitrate metabolism responsible for the shutdown in bacterial growth. This would suggest the potentiating effects of glutathione should be evident with NO gas. Discrete volumes of TSB were surface gassed with 2.31% NO in $N_2$ gas mixture for a fixed time (45 min) that resulted in a two-fold titration from a concentration that resulted in minimal inhibition of aerobic growth. There was dose dependent enhancement of inhibition at the 0.5 relative concentration of NO by GSH, but not at lower NO concentrations. The same experiment designed to examine the influence of NO on anaerobic growth in TSBN did not work, presumably because the process of degassing and reducing $O_2$ for entry into the anaerobic chamber reduced the NO in the media. This was true even if GSH was available in the media before degassing, suggesting that the NO was not stabilized by interaction with GSH.
Figure 6:
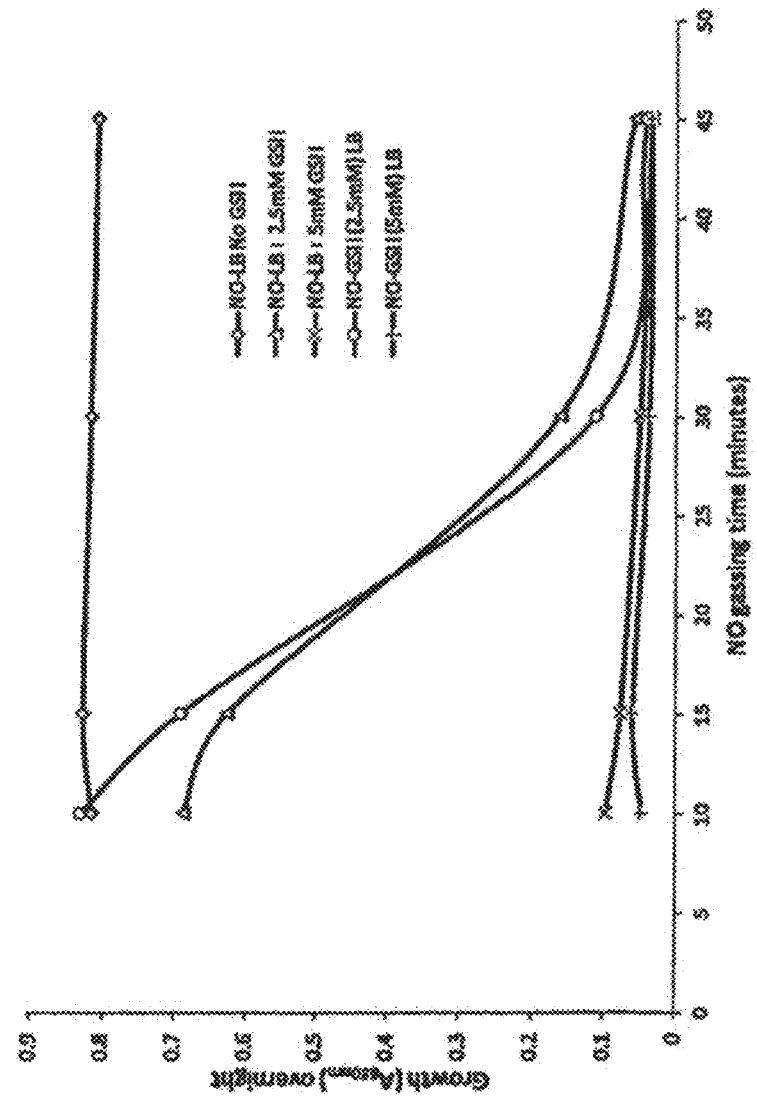
FIG. 6. Glutathione potentiation of NO mediated inhibition of Pa PAO1 aerobic growth in Luria Bertani broth is independent of order of addition of GSH. If NO reacts with glutathione to generate nitrosoglutathione then gassing with NO in the presence of glutathione may be expected to yield greater activity than gassing first and then adding glutathione. To test this effect, LB broth was either pre-gassed with NO followed by titration of GSH or the LB broth aliquots containing various concentrations of GSH were gassed. Titration of NO was accomplished by varying the gassing times of the LB broth. There was no discernible inhibition with any of the concentrations of NO in the absence of glutathione. In the presence of 5 mM glutathione, the lowest concentration of NO (10 minutes gassing time) resulted in total inhibition. The 2.5 mM revealed a dose dependent NO inhibition of growth. The growth inhibiting synergistic activity between glutathione and NO was independent of whether glutathione was present during gassing (NO-GSH) or added after (NO-LB+GSH).
Figure 7:
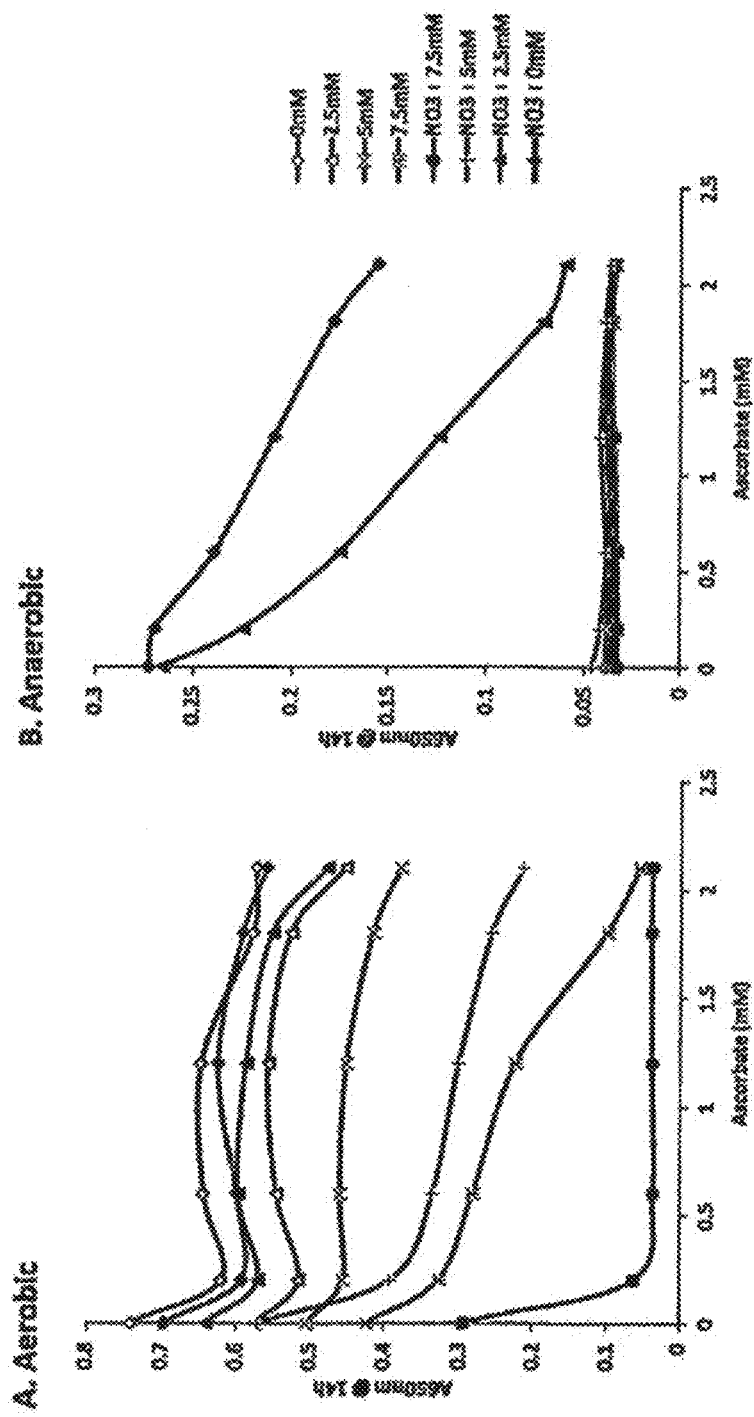
FIG. 7. Complementary effects of ascorbate on glutathione inhibition of nitrate independent and dependent growth of PAO1. The next series of experiments was designed to determine if there were any influences of ascorbate on glutathione potentiation of the growth inhibition of the RNI (FIGS. 7, 8 and 9). Again aerobic growth was minimally influenced by the presence of nitrate in the absence of both glutathione and ascorbate and there were no discernible differences on the effects of ascorbate titration on growth in the presence or absence of nitrate (Panel A). In contrast, there was a dose dependent reduction in the aerobic growth attained by PAO1 that could be attributed to glutathione in LB broth that was further enhanced by adding increasing concentrations of ascorbic acid (Panel A). The most pronounced inhibition in the absence of nitrate of aerobic growth occurred with 7.5 mM glutathione that was enhanced by titration of ascorbate reaching total inhibition with 2.1 mM ascorbate (Panel A). This was likely due to the combined reducing potential of the glutathione and ascorbate limiting oxygen dependent growth. In contrast, ascorbate concentrations of 0.2 mM with 7.5 mM glutathione resulted in profound inhibition of growth in ambient atmosphere in the presence of nitrate. Likewise, the presence of nitrate resulted in greater inhibition of aerobic growth with 5 mM glutathione and ascorbate. In the absence of glutathione, the influence of ascorbate on growth in ambient atmosphere appeared to be independent of the presence of nitrate (Panel A). In contrast, growth in an anaerobic atmosphere was only evident with nitrate. Only the 2.5 mM (Panel B) and lower concentrations of glutathione permitted growth in the absence of ascorbate. There was a dose dependent decrease in nitrate-dependent growth with increasing concentrations of ascorbate in the absence of glutathione that was more pronounced in the presence of 2.5 mM glutathione (Panel B).
Figure 8:
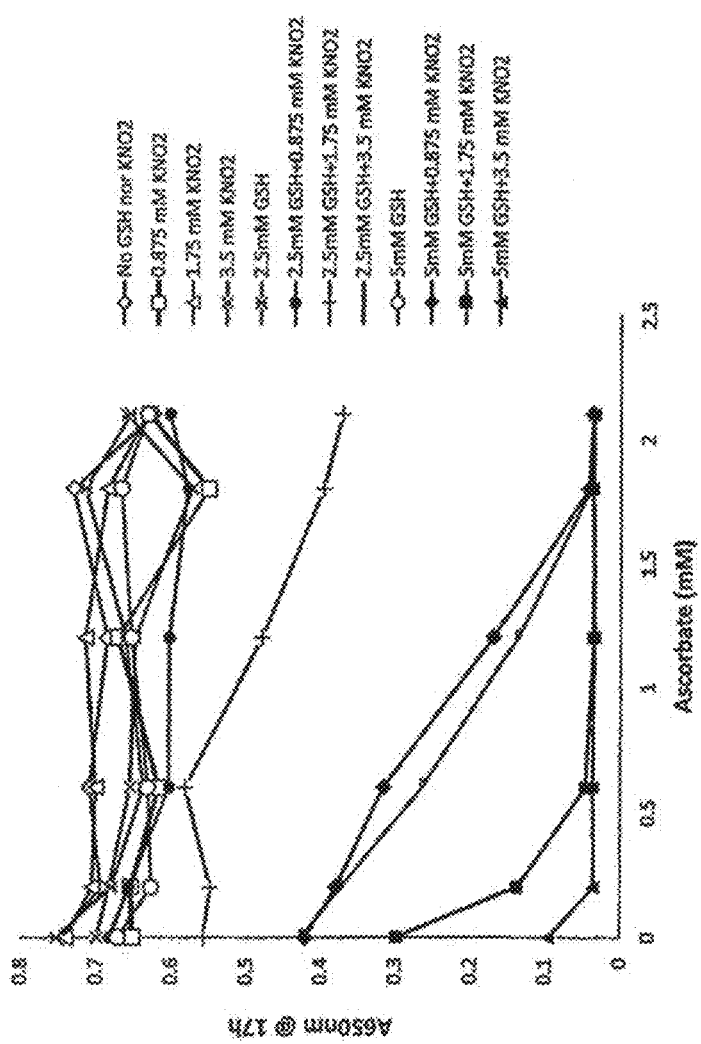
FIG. 8. Ascorbate effects on the inhibitory activities of nitrite and glutathione on aerobic growth of PAO1. Ascorbate was titrated over a checkerboard titration of glutathione and $KNO_2$ in LB broth. The data presented are representative of three different experiments with a wider range of concentrations of individual components. In these experiments, neither $KNO_2$ to 3.5 mM, glutathione to 5 mM nor ascorbate to 2.1 mM had discernible effects on the aerobic growth of PAO1 attained by 17 h. There also was no discernible effect of ascorbate addition to either glutathione or $KNO_2$ at the concentrations tested. Again there were concentration dependent inhibitory effects for $KNO_2$ in the presence of glutathione that were enhanced by the addition of ascorbate. This synergistic inhibition was evident with as little as 0.875 mM $KNO_2$ in the presence of 5 mM glutathione and as little as 2.5 mM glutathione in the presence of 1.75 mM $KNO_2$.
Figure 9:
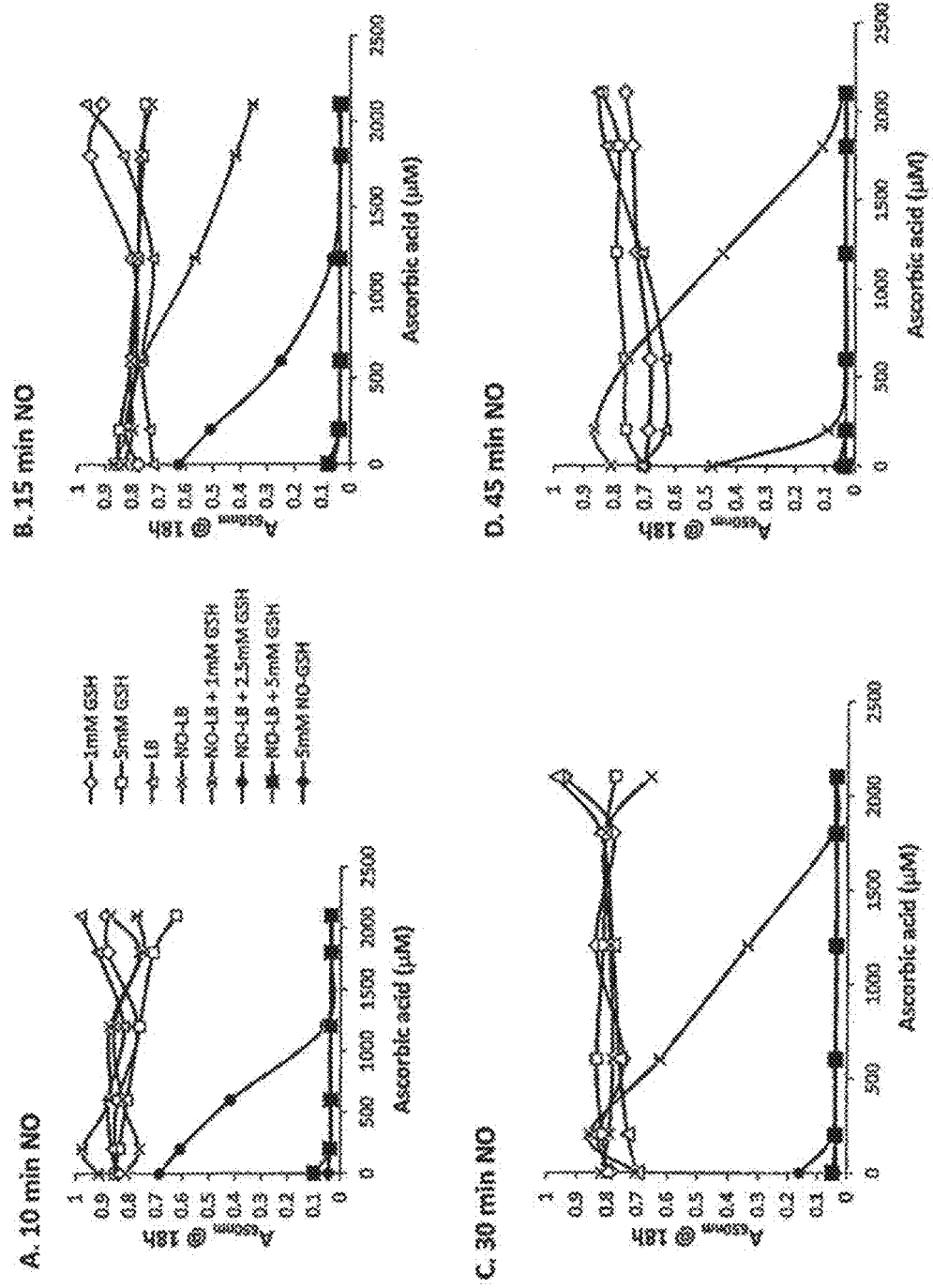
FIG. 9. Ascorbate effects on the inhibitory activities of nitric oxide and glutathione on aerobic growth of PAO1. In these experiments, varying concentrations of NO were achieved again by varying the gassing time (10, 15, 30 or 45 min) with 2.3% NO in $N_2$ either in the presence (NO-GSH) or absence (NO-LB) of varying concentrations of glutathione. Glutathione was added to NO-LB in varying concentrations (NO-LB+GSH). Again in the absence of NO there were no inhibitory effects of either the glutathione or the ascorbate concentrations and combinations employed in this study. Bubbling of the media with $N_2$ gas for 45 min did not have any of the inhibitory effects of the NO—$N_2$ gas mixture. At the highest concentration (5 mM) of glutathione presented there was total inhibition of growth in the presence of the lowest concentration of NO regardless of the order of NO/glutathione addition (Panel B). With the 2.5 mM concentration of glutathione there may have been some advantage to bubbling in the presence of glutathione (2.5 mM NO-GSH) as opposed to adding glutathione after bubbling (NO-LB+2.5 mM GSH); however, any differences due to order of addition appeared to be lost with longer NO delivery (Panels B, C and D). With the 15 min delivery of NO, there is identical concentration dependent ascorbate enhancement of inhibition with the 2.5 mM NO-GSH and NO-LB+2.5 mM GSH.
Figure 10A:

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

A subject "in need thereof" as used herein refers to a subject that can benefit from the therapeutic and/or prophylactic effects of the pharmaceutical compositions of the present invention. Such a subject can be a subject diagnosed with a disease or disorder of this invention, a subject suspected of having or developing a disorder or disease of this invention, and/or a subject determined to be at increased risk of having or developing a disease or disorder of this invention.

By the term "treat," "treating," or "treatment of" (and grammatical variations thereof) it is meant that the severity of the subject's condition is reduced, at least partially improved or ameliorated, and/or that some alleviation, mitigation or decrease in at least one clinical symptom is achieved and/or there is a delay in the progression of the disease or disorder.

The terms "prevent," "preventing," and "prevention of" (and grammatical variations thereof) refer to reduction and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of a composition of the present invention.

As used herein, the terms "therapeutically effective amount" or "effective amount" refer to an amount of a composition or formulation of this invention that elicits a therapeutically useful response in a subject. Those skilled in the art will appreciate that the therapeutic effects need not be complete or curative, as long as some benefit is provided to the subject.

As used in the description of the invention and the appended claims, the singular forms "a," "an" and "the" are intended to include the plural forms as well, unless the context clearly indicates otherwise. For example, "a cell" can mean a single cell or a multiplicity of cells.

Also as used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration (e.g., the amount of the benzodiazepine in the pharmaceutical composition) and the like, is meant to encompass variations of 20%, 10%, 5%, 1%, 0.5%, or even 0.1% of the specified amount.

Unless the context indicates otherwise, it is specifically intended that the various features of the invention described herein can be used in any combination. For example, features described in relation to one embodiment may also be applicable to and combinable with other embodiments and aspects of the invention.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

Pharmaceutical Compositions

The present invention is based on the discovery that pharmaceutical compositions of this invention, comprising for example in some embodiments, glutathione, an organic acid (e.g., ascorbic acid), bicarbonate and, optionally, thiocyanate can be used as an antimicrobial and/or anti-inflammatory agent to treat diseases and disorders in mucosal tissue, as well as to establish, reestablish, and/or maintain the homeostatic environment in mucosal surface fluid to restore or enhance the subject's natural healing and defense mechanisms. The reason glutathione hasn't worked in the past is that it must also have the activities of bicarbonate and ascorbate as well to bring in to play other complementary innate defenses and anti-inflammatory molecules. Likewise, the addition of thiocyanate arms another component of exocrine secretions with both antimicrobial and anti-inflammatory activities. It is not simply the buffering capacity of bicarbonate that is important, the function of lactoferrin has specificity in its coordinate binding of iron for carbonate/bicarbonate and their ratio is central to determining both the antimicrobial and anti-inflammatory functions of this critical exocrine protein. Likewise, ascorbate was chosen not simply because it is an organic acid, but because of its iron reducing potential and its specific and unique relationship to the functions of lactoferrin. Carbonate provokes exaggerated expression of the mucoidy trait (associated with virulence) of *Pseudomonas aeruginosa* and this is suppressed specifically by bicarbonate, presumably facilitating host defense against this critical airway pathogen. The unique importance/functions of ascorbate and bicarbonate, both of which are deficient in the cystic fibrosis (CF) airway and in other secretions that bathe mucosal surfaces, in addition to glutathione with or without thiocyanate addresses previous shortcomings in the art.

Thus, the present invention provides various compositions and formulations as set forth herein.

A composition of this invention can comprise, consist essentially of or consist of a) glutathione, a pharmaceutically-acceptable salt of glutathione, or a derivative or a prodrug thereof, b) an organic acid, a pharmaceutically-acceptable salt of an organic acid, such as ascorbic acid, or a derivative or prodrug thereof, and c) a bicarbonate salt, such as sodium or potassium bicarbonate. A pH adjusting agent can also be present in the composition to adjust the pH of the composition to fall within a range from about 5 to about 9, from about 6 and about 8, or from about 6.5 to about 7.5.

The weight ratios of these components (i.e., active agents) can vary over wide ranges. Typically, the amount of each component is selected such that there is sufficient bicarbonate salt to bring the pH to the desired range, while also allowing for the bicarbonate salt to be present along with the glutathione and organic acid.

It is to be understood that, as the relative amounts of glutathione and organic acid, such as ascorbic acid, can vary, the amounts of bicarbonate salt can also vary. If glutathione and the organic acid are mixed with a bicarbonate salt, the acid functional groups will react with the bicarbonate to form the salts of the glutathione and the organic acid, and the bicarbonate will be acidified to form carbonic acid, with concomitant formation of water and evolution of carbon dioxide. Accordingly, if the formulation is prepared by mixing the acids with a bicarbonate salt, what is intended is that sufficient bicarbonate is added wherein the bicarbonate salt is present in a molar amount equal to the combined molar amount of the glutathione and the organic acid or in a molar excess of the combined molar amount of the glutathione and the organic acid. For example, the molar excess of the bicarbonate salt can be in a range from greater than 1.0 to less than about 1.5.

The weight ratios of these components can vary over wide ranges. For example, the weight of a) can be from about 0.1 to about 95 percent by weight, b) can be from about 0.5 to about 60 percent by weight, and c) can be from about 1 to about 55 percent by weight. Within these ranges, the amount of a) can be, for example, from about 52 to about 80 weight percent, b) can be from about 3 to about 18 weight percent, and c) can be from about 17 to about 30 weight percent.

In some embodiments, glutathione precursors such as methionine, cysteine or N-acetyl cysteine (NAC) can be included in the compositions of this invention in addition to, or in place of, glutathione. These precursors enable glutathione to be produced intracellularly. This can be important in certain embodiments, as glutathione is not taken up by cells, and will not work if supplied on the outside of the cell. So, for example, for perfusion solutions to preserve transplant organs between harvest and transplantation, it can be advantageous to use a glutathione precursor in a composition of this invention. In some embodiments, a composition of this invention comprising a glutathione precursor in place of glutathione can be used to perfuse the vasculature of an organ and a composition of this invention comprising glutathione can be used to perfuse the airway of an organ, to preserve endothelial function. Thus, the compositions and formulations of this invention can be used to preserve both mucosal and endothelial tissue.

In some embodiments, a composition of this invention can further comprise, consist essentially of or consist of (e.g., as an additional active agent) from about 0.01% to about 5% by weight of a pharmaceutically-acceptable thiocyanate salt, such as from about 1% to about 2% by weight of a thiocyanate salt, while maintaining the weight ratios of the other components.

In some embodiments, the compositions can further include precursors to glutathione, such as methionine, cysteine and/or N-acetyl cysteine, in amounts of from about 0.1 to about 10% by weight, while maintaining the weight ratios of the other components. In one aspect of this embodiment, a glutathione precursor such as methionine, cysteine and/or N-acetyl cysteine can be used in place of glutathione, rather than in addition to glutathione. In this aspect, the dosage of the glutathione precursor can be that of glutathione.

The pharmaceutical compositions described herein can be present in the form of solid formulations, such as particulate formulations, or in solution form. When in particulate form, the particles can be mixed with gases, or liquid propellants, for use in inhalation therapy. Other solid formulations include formulations for oral administration, but buccal administration or colonic administration, and suppositories for rectal or vaginal administration. Representative formulations include, but are not limited to, the following: eye drops, nebulizers, topical gels and ointments, dry powders, particles, sprays, liquids, anesthetic machines or vaporizers, autoinjectors, intrauterine devices, respimats, liniments, liposomes, lotions, formulations for intramuscular, intrathecal, or subcutaneous injection, douches, infusions, and face masks.

In solution form, the formulations can be in the form of sprays for intranasal administration, formulations for use in nebulizers, and formulations for rectal administration, such as enemas and colonics. Solutions that include water-miscible organic solvents, such as propylene glycol and/or glycerol, and other components normally found in vaginal and rectal lubricants, can also be used. Regardless of the solvents used, the solvent is typically present in a weight ratio of from about 15 to about 85 percent by weight, relative to the weight of the solids, and, more typically, is from about 50 to about 85% by weight.

In some embodiments, the present invention provides a pharmaceutical composition comprising glutathione, a pharmaceutically acceptable salt thereof, a derivative thereof, an analogue thereof and/or a prodrug thereof, an organic acid, a pharmaceutically acceptable salt thereof, a derivative thereof, an analogue thereof and/or a prodrug thereof, and a bicarbonate. In some embodiments, this pharmaceutical composition can further comprise thiocyanate, a pharmaceutically acceptable salt thereof, a derivative thereof, an analogue thereof and/or a prodrug thereof.

In some embodiments, the pharmaceutical composition of this invention can comprise glutathione that is oxidized glutathione.

In some embodiments, the pharmaceutical composition of this invention can comprise glutathione that is reduced glutathione.

In various embodiments of this invention, the liquid pharmaceutical compositions of this invention can have a pH in a range from about 2.0 to about 10 (e.g., 2.0, 2.5, 3.0, 3.5, 4.0, 4.5, 5.0, 5.5, 6.0, 6.5, 7.0, 7.5, 8.0, 8.5, 9.0, 9.5, 10.0). In some embodiments, the pH can be in a range from about 5.5 to about 9.0).

A pharmaceutical composition of this invention can further comprise a chelating agent and/or a preservative.

The pharmaceutical composition of this invention can be formulated for controlled release (i.e., in a controlled release formulation).

In some embodiments, the pharmaceutical composition of this invention can be in a form for administration by inhalation, as described herein and as is well known in the art.

In some embodiments, the pharmaceutical composition of this invention can be in a form for intranasal administration, as described herein and as is well known in the art.

In some embodiments, the pharmaceutical composition of this invention can be in a form for administration to an eye, as described herein and as is well known in the art.

In some embodiments, the pharmaceutical composition of this invention can be in a form for administration to an ear, as described herein and as is well known in the art.

In further embodiments, the pharmaceutical composition of this invention can be in a form for administration to a mucosal surface, as described herein and as is well known in the art. Nonlimiting examples of tissues with mucosal surface/lining include the mouth, nose, eye, ear, upper respiratory tract, lower respiratory tract, gastrointestinal tract, vagina, rectum and urethra.

Glutathione and Derivatives Thereof

The term "glutathione" encompasses the tripeptide N—(N-L-γ-glutamyl-L-cysteinyl)glycine, often called L-glutathione, glutathione-SH, or γ-Glu-Cys-Gly, and sold under a variety of tradenames such as Agifutol S™, Copren™, Deltathione™, Isethion™, Neuthion™, Tathiclon™, Tathion™ and Triptide™. As used herein, where the properties and advantages of "glutathione" (or GSH) are discussed as an active ingredient in the practice of the invention, biologically active glutathione derivatives are encompassed. "Glutathione derivatives" include, but are not limited to, reduced glutathione (or GSSG), glutathione salts, particularly reduced glutathione potassium or sodium salts.

In some embodiments, glutathione derivatives of this invention can include, but are not limited to, glutathione prodrugs, including but not limited to glutathione alkyl esters, particularly $C_1$ to $C_{10}$ alkyl esters, especially monoesters such as monomethyl and monoethyl esters, which have the glycine carboxylic acid group acylated, as these have been shown to increase cellular levels of glutathione (U.S. Pat. No. 4,710,489 to Meister), and corresponding amides and imides (such as those set out in U.S. Pat. No. 5,541,162 to Ohmori, et al).

In other embodiments, glutathione derivatives can include, but are not limited to, glutathione prodrugs, including but not limited to sulfhydryl-modified prodrugs of glutathione (Berkeley et al. "Hepatoprotection by L-cysteine-glutathione mixed disulfide, a sulfhydryl-modified prodrug of glutathione" *J Biochem. Mol. Toxicol.* 17:95-97 (2003)) diesters based on N-benzyloxycarbonyl-S-2,4-dinitrophenylglutathione (Daunes et al. "Glutathione Derivatives Active against *Trypanosoma brucei* rhodesiense and *T. brucei brucei* In Vitro" Antimicrobial Agents and Chemother. 46(2):434-437 (2002)) and glutathione prodrugs (Cacciatore et al. "Prodrug Approach for Increasing Cellular Glutathione Levels" *Molecules* 15:1242-1264 (2010)).

In other embodiments, glutathione derivatives of this invention can include, but are not limited to, analogues (Cacciatore et al. "Synthesis and activity of novel glutathione analogues containing an urethane backbone linkage" *Farmaco* 58(9):787-793 (2003)), isosteres (Cacciatore et al. "Transition State Isosteres of the γ-Glutamyl Peptide Bond Hydrolysis: Synthesis and Characterization of the ψ(CH2NH) Pseudopeptide Analogue of Glutathione" *J Peptide Sci.* 10:109-114 (2004)) and conformationally restricted glutathione analogues (Paglialunga et al. "Proline-glutamate chimeras in isopeptides, Synthesis and biological evaluation of conformationally restricted glutathione analogues" *Bioorg. Med. Chem.* 11:1677-1683 (2003)).

In other embodiments, configurational isomers, optically pure enantiomers, mixtures of enantiomers such as racemates, diastereomers, mixtures of diastereomers, diastereomeric racemates, mixtures of diastereomeric racemates and the meso-form as well as pharmaceutically acceptable salts of glutathione and glutathione derivatives are included. The present invention encompasses all these forms.

In some embodiments, glutathione precursors, such as methionine, cysteine or NAC are used, in addition to, or in place of glutathione. The dosage can mirror that of the glutathione.

The present invention furthermore encompasses glutathione and derivatives of glutathione, for example solvates, such as hydrates and adducts with alcohols, esters, prodrugs and other physiologically tolerated derivatives and also active metabolites of glutathione. Furthermore, the invention contains all crystal modifications of glutathione and glutathione derivatives.

In still other embodiments, some of the crystalline forms of glutathione and the glutathione derivatives may exist as polymorphs, which are included in the present invention.

Organic Acids

In the pharmaceutical compositions recited above, the organic acid can be, but is not limited to, ascorbic, acetic, adipic, aspartic, benzenesulfonic, benzoic, butyric, camphorsulfonic, camsylic, carbonic, chlorobenzoic, cholic, citric, edetic, edisylic, estolic, ethanesulfonic, formic, fumaric, gluceptic, gluconic, glucuronic, glutamic, glycolic, glycolylarsanilic, hippuric, 1-hydroxy-2-naphthoic, isethionic, isobutyric, isonicotinic, lactic, lactobionic, maleic, malic, malonic, mandelic, methanesulfonic, mucic, muconic, napthalenesulfonic, nicotinic, oxalic, oleic, orotic, p-nitromethanesulfonic, pamoic, pantothenic, phthalic, polygalactouronic, propionic, saccharic, salicylic, stearic, suberic, succinic, sulfanilic, tannic, tartaric, p-toluenesulfonic and any combination thereof.

pH Adjusting Agents

Suitable pH adjusting agents are well-known in the art (see *Remington's Pharmaceutical Sciences,* 18th edition, A. R Gennaro, Ed., Mack Publishing Company (1990) and *Handbook of Pharmaceutical Excipients,* 3rd edition, A. Kibbe, Ed., Pharmaceutical Press (2000). Suitable examples of pharmaceutically acceptable pH adjusting agents include, but are not limited to, citric acid, sodium citrate, sodium bicarbonate, dibasic sodium phosphate, magnesium oxide, calcium carbonate and magnesium hydroxide. Suitable pH adjusting agents for use with the invention include, but are not limited to, acetate buffers, citrate buffers, phosphate buffers, lactic acid buffers, and borate buffers.

Fat-soluble fatty acid esters of ascorbic acid (vitamin C) are employed as an adjunct ingredient in some embodiments, alone or in combination with α-hydroxy acids. The more oxidation-resistant saturated fatty acid esters of ascorbic acid can be used, including, but not limited to, ascorbyl laurate, ascorbyl myristate, ascorbyl palmitate, ascorbyl stearate, and ascorbyl behenate. Ascorbyl palmitate can be used in some embodiments. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, can commonly contain about 4% ascorbyl palmitate.

Preservatives

Suitable examples of pharmaceutically acceptable preservatives include, but are not limited to, various antibacterial and antifungal agents, solvents, for example, ethanol, propylene glycol, benzyl alcohol and chlorobutanol, quaternary ammonium salts including, but not limited to, cetylpyridinium chloride, benzalkonium chloride and parabens including, but not limited to, methyl paraben, ethyl paraben and propyl paraben.

In other embodiments, pharmaceutically acceptable preservatives of this invention can include, but are not limited to, chlorhexidine, benzoic acid and the salts thereof, parahydroxybenzoic acids and the salts thereof, alkyl esters of parahydroxybenzoic acid and the salts thereof, phenylmercuric salts such as nitrate, chloride, acetate, and borate, or antioxidants, as well as additives like EDTA, sorbitol and the like.

In still other embodiments, pharmaceutically acceptable preservatives of this invention can include, but are not limited to, phenol, boric acid and the salts thereof, sorbic acid and the salts thereof, thimerosal and nitromersol.

Chelating Agents

Non-limiting examples of chelating agents suitable for use in the present invention include lactic acid, acetic acid, oxalic acid, malonic acid, succinic acid, maleic acid, fumaric acid, aconitic acid, pimelic acid, sebacic acid, allymalonic acid, ethylmalonic acid, citric acid, malic acid, glyceric acid, tartaric acid, mevaloic acid, oxyglutaric acid, oxaloacetic acid, α-ketoglutaric acid, β-ketoglutaric acid, α-ketomalonic acid, glucuronic acid, galaceturonic acid, mannuronic acid, aspartic acid, glutamic acid, glycine, alanine, lysine, histidine, alginine, cysteine, ε-aminocaproic acid, phenylalanine, phenylglycine, p-hydroxyphenylglycine, p-aminophenylalanine, γ-carboxyglutamic acid, iminodiacetic acid, hydroxyethyliminodiacetic acid, ethylenediaminediacetic acid, ethylenediaminetetraacetic acid, trans-cyclohexane-diaminetetraacetic acid, diethylenediaminepentaacetic acid, β-alaninediacetic acid, diaminopimelic acid, phthalic acid, terephthalic acid, homophthalic acid, phenylsuccinic acid, phenylmalonic acid, oxanylic acid-o-carboxylic acid, anthralininoacetic acid, 2,4-dihydroxybenzoic acid, p-aminosalicyclic acid, phthalyglutamic acid, kynurenine, 1,2-hyroxybenzene-3,5-disulfonic acid, 4-amino-phenol-2-sulfonic acid, cysteic acid, 2-phosphoglyceric acid, glycero-3-phosphoric acid, glucose-1,6-diphosphoric acid, fructose-1,6-diphosphoric acid and phosphates (e.g., sodium phosphate, sodium aluminum phosphate, sodium acid phosphate, dipotassium phosphate, disodium phosphate, monobasic and sodium hexametaphosphate) and any combination thereof.

Chelating agents can be included in the pharmaceutical compositions of this invention either as the parent molecule or in the salt form where appropriate. For example, compounds containing an acid function may be used in the protonated form or as a pharmaceutically acceptable inorganic or organic salt which retains the chelating activity of the parent compound.

Pharmaceutically-Acceptable Salts

The pharmaceutically-acceptable salts will be any salt that is not deleterious to the subject or otherwise contraindicated. Such salts are for example, salts derived from inorganic bases which include sodium, potassium, lithium, ammonium, calcium, magnesium, ferrous, zinc, copper, manganous, aluminum, ferric, manganic salts and the like. Particular salts include the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Organic non-toxic bases can be isopropylamine, diethylamine, ethanolamine, tromethamine, dicyclohexylamine, choline and caffeine.

Where the chelating agent has more than one acid function, one or more of the acid functions may be in the salt form. For example, EDTA may be used as the mono, di, tri or tetrasodium salt or the disodium, monocalcium salt may be used as an alternative. Particular examples of a chelating agent of this invention include the alkali metal salts of EDTA. Further examples include the mono and disodium salt of EDTA.

Therapeutic Agents

In addition to the components of the formulations described above, the formulations can also include one or more therapeutic agents.

In still further embodiments, the composition is combined with one or more additional therapeutic agents. Representative therapeutic agents include, but are not limited to, monoclonal antibodies, immunomodulatory agents, including agents that cause T and B cell activation, proliferation, and/or maturation; agents that bring about innate immune system activation, proliferation, maturation (e.g., JNK, MAPK, ERK, NK kappa B pathway agonists or antagonists, and monocyte, neutrophil, or macrophage agonists or antagonists), matrix metalloproteinase inhibitors, heat shock protein agonists or antagonists, alpha synuclein inhibitors, chelating agents, diuretics, alpha 1 antitrypsin modulators, purinoceptor agonists or antagonists, cyclooxygenase 2 inhibitors, DNA gyrase inhibitors, natural killer cell and natural killer T cell agonists or antagonists, cathepsin class agonists or antagonists, antioxidant therapies, rho-associated kinase inhibitors, myosin inhibitors, phosphatidylinositol 3 kinase inhibitors and related molecules, nitric oxide synthase agonists or antagonists, nitric oxide agonists or antagonists, ion channel function or trafficking modulators, surfactant therapies, in particular, lung surfactants, cannabinoid receptor modulators, complement system inhibitors, IgE receptor antagonists, G protein-coupled receptor agonists or antagonists, chemokines, chemokine receptor agonists or antagonists, cytokines, and cytokine receptor agonists or antagonists, arachidonic acid agonists or antagonists, inflammatory mediators, STAT6 inhibitors, histamine or leukotriene agonists or antagonists, and calcineurin agonists or antagonists. Examples of these therapeutic agents and their use are described in more detail below.

Matrix Metalloproteinase Inhibitors

Matrix metalloproteinase inhibitors (MMPIs) inhibit matrix metalloproteinases, and have antiangiogenic effects. MMPIs can be endogenous or exogenous. Examples of endogenous metalloproteinases include tissue inhibitors of metalloproteinases (TIMPs) and cartilage-derived angiogenesis inhibitors. Exogenous matrix metalloproteinase inhibitors that were developed as anticancer drugs include Batimastat and Marimastat.

All cancerous tumors release angiogenic growth factor proteins that stimulate blood vessels to grow into the tumor, providing it with oxygen and nutrients. Antiangiogenic therapies starve the tumor of its blood supply. Cancer treatments that block angiogenesis are now approved and available to treat cancers of the colon, kidney, lung, breast, liver, brain, and thyroid, as well as multiple myeloma, bone gastrointestinal stromal tumors, soft tissue sarcoma, and SEGA tumors. Other angiogenesis-dependent conditions include hemangiomas, colon polyps, and precancerous skin lesions. MMP enzymes are also thought to contribute to the deterioration of cartilage in osteoarthritis patients.

MMPIs can therefore be used for their antiangiogenic properties, in the treatment of cancer, arthritis, and other disorders associated with angiogenesis.

When treating certain forms of lung cancer, it can be helpful to maintain the homeostasis of the lung tissue, so co-administration or separate administration of chemotherapeutic agents such as MMPIs and the glutathione/ascorbic acid/sodium bicarbonate formulations described herein can be used for this purpose. That is, the MMPIs can be used for their antiangiogenic properties, as well as for their anti-inflammatory properties, to treat cancer, arthritis, and other disorders. Co-administration or separate administration of chemotherapeutic agents such as MMPIs and the glutathione/ascorbic acid/sodium bicarbonate formulations described herein can be used to maintain homeostasis in the mucosal membranes of the lung tissue.

Monoclonal Antibodies

Monoclonal antibodies (mAb or moAb) are monospecific antibodies produced by identical immune cells that are all clones of a unique parent cell, in contrast to polyclonal antibodies which are made from several different immune cells. Monoclonal antibodies have monovalent affinity, in that they bind to the same epitope.

Monoclonal antibody therapy is the use of monoclonal antibodies (or mAb) to specifically bind to target cells or proteins. This may then stimulate the patient's immune system to attack those cells. It is possible to create a mAb specific to almost any extracellular/cell surface target, and thus there is a large amount of research and development currently being undertaken to create monoclonals for numerous serious diseases (e.g., rheumatoid arthritis, multiple sclerosis, Alzheimer's disease and different types of cancers). There are a number of ways that mAbs can be used for therapy. For example: mAb therapy can be used to destroy malignant tumor cells and prevent tumor growth by blocking specific cell receptors. Variations also exist within this treatment (e.g. radioimmunotherapy) where a radioactive dose localizes on target cell line, delivering lethal chemical doses to the target. Examples of monoclonal antibodies used include, but are not limited to, Adalimumab, Alemtuzumab, Basiliximab and Omalizumab.

Monoclonal antibody therapies are used for a variety of diseases, such as asthma autoimmune diseases, cancers, and general immunosuppression. When the therapeutic agents described herein are used in combination with the antibodies, one can reduce dosages of monoclonal antibody therapies, thereby limiting exposure to toxic drug levels. Additionally, the compounds can be used in conjunction with monoclonal antibodies and/or other therapies to increase efficacy and/or decrease side effects.

Monoclonal antibodies that bind only to cancer cell-specific antigens and induce an immunological response against the target cancer cell can be used to treat cancer. Such mAbs can be modified for delivery of a toxin, radioisotope, cytokine or other active conjugate. MAbs currently approved by the U.S. Food and Drug Administration (USFDA) include Bevacizumab, Cetuximab, Panitumumab and Trastuzumab.

Monoclonal antibodies used for autoimmune diseases include infliximab and adalimumab, which are effective in rheumatoid arthritis, Crohn's disease and ulcerative Colitis by their ability to bind to and inhibit TNF-α. Basiliximab and daclizumab inhibit IL-2 on activated T cells and thereby help prevent acute rejection of kidney transplants. Omalizumab inhibits human immunoglobulin E (IgE) and is useful in moderate-to-severe allergic asthma.

Immunomodulatory Agents

Immunotherapy is a medical term defined as the "treatment of disease by inducing, enhancing, or suppressing an immune response." Immunotherapies designed to elicit or amplify an immune response are classified as activation immunotherapies, while immunotherapies that reduce or suppress are classified as suppression immunotherapies.

The therapeutic agents of immunotherapy are collectively called immunomodulators. They are a diverse array of recombinant, synthetic and natural preparations, often cytokines. Some of these substances, such as granulocyte colony-stimulating factor (G-CSF), interferons, imiquimod and cellular membrane fractions from bacteria are already licensed for use in patients. Others including IL-2, IL-7, IL-12, various chemokines, synthetic cytosine phosphate-guanosine (CpG), oligodeoxynucleotides and glucans are currently being investigated extensively in clinical and pre-clinical studies. Immunomodulatory regimens offer an attractive approach as they often have fewer side effects than existing drugs, including less potential for creating resistance in microbial diseases.

Cell-based immunotherapies have proven to be effective for some cancers. Immune effector cells such as lymphocytes, macrophages, dendritic cells, natural killer cells (NK cell), cytotoxic T lymphocytes (CTL), etc., work together to defend the body against cancer by targeting abnormal antigens expressed on the surface of the tumor due to mutation.

Immune suppression dampens an abnormal immune response in autoimmune diseases or reduces a normal immune response to prevent rejection of transplanted organs or cells.

Immunosuppressive drugs are important tools in the management of organ transplantation and autoimmune disease. Immune responses depend on lymphocyte proliferation and cytostatic drugs are immunosuppressive. Glucocorticoids are somewhat more specific inhibitors of lymphocyte activation, whereas inhibitors of immunophilins more specifically target T lymphocyte activation. Immunosuppressive antibodies target an increasingly-broad array of steps in the immune response, and there are still other drugs that modulate immune responses.

Immune tolerance is the process by which the body naturally does not launch an immune system attack on its own tissues. Immune tolerance therapies seek to reset the immune system so that the body stops mistakenly attacking its own organs or cells in autoimmune disease or accepts foreign tissue in organ transplantation. A brief treatment should then reduce or eliminate the need for lifelong immunosuppression and the chances of attendant side effects, in the case of transplantation, or preserve the body's own function, at least in part, in cases of type 1 diabetes or other autoimmune disorders. Another example of this is using helminthic therapies to modulate the immune system (e.g., Crohn's disease).

A potential use of immunotherapy is to restore the immune system of patients with immune deficiencies as result of infection or chemotherapy. For example, cytokines have been tested in clinical trials; interleukin-7 has been in clinical trials for HIV and cancer patients. In addition, interleukin-2 has also been tested in HIV patients.

Anti-microbial immunotherapy, which includes vaccination, involves activating the immune system to respond to an infectious agent.

Examples of immunomodulatory agents include, but are not limited to, tacrolimus, mycophenolate sodium, corticosteroids, innate immune system activation, proliferation, maturation (e.g., JNK (Jun amino-terminal kinases), MAPK (Mitogen-activated protein kinase), ERK (extracellular signal-regulated kinases), NK kappa B (nuclear factor kappa-light-chain-enhancer of activated B cells) pathway agonists or antagonists, and monocyte, neutrophil, or macrophage agonists or antagonists), STAT6 inhibitors, natural killer cell and natural killer T cell agonists or antagonists, calcineurin agonists or antagonists (partial agonists, inverse agonists, and allosteric modulators), chemokines, chemokine receptor agonists or antagonists, cytokines, and cytokine receptor agonists or antagonists.

Immunomodulators weaken or modulate the activity of the immune system, which, in turn, decreases the inflammatory response. Immunomodulators are most often used in organ transplantation to prevent rejection of the new organ, in autoimmune diseases such as rheumatoid arthritis, and to patients with irritable bowel disorder (IBD), which appears to be caused by an overactive immune system. Immunomodulators are often combined with corticosteroids to speed up response during active flares of disease.

Representative immunomodulatory agents also include agents that cause T and B cell activation, proliferation, and/or maturation; agents that bring about innate immune system activation, proliferation, maturation Representative agents which modulate NK kappa B include denosumab, Disulfiram, olmesartan, dithiocarbamates, and Anatabine.

Heat Shock Protein Agonists/Antagonists/Partial Agonists/Inverse Agonists

Heat shock proteins (HSP) are a group of proteins induced by heat shock. The most prominent members of this group are a class of functionally related proteins involved in the folding and unfolding of other proteins. Their expression is increased when cells are exposed to elevated temperatures or other stress.

Heat Shock Factor 1 (HSF1) is a transcription factor that is involved in the upregulation of Hsp70 protein expression. Recently it was discovered that HSF1 is a powerful multi-faceted modifier of carcinogenesis.

Given their role in antigen presentation, HSPs are useful as immunologic adjuvants in boosting the response to a vaccine. Furthermore, some researchers speculate that HSPs may be involved in binding protein fragments from dead malignant cells and presenting them to the immune system. Therefore HSPs may be useful for increasing the effectiveness of cancer vaccines.

Intracellular heat shock proteins are highly expressed in cancerous cells and are essential to the survival of these cell types. Hence small molecule inhibitors of HSPs, especially Hsp90 show promise as anticancer agents. The potent Hsp90 inhibitor 17-AAG is currently in clinical trials for the treatment of several types of cancer. HSPgp96 also shows promise as an anticancer treatment and is currently in clinical trials against non-small cell lung cancer.

Alpha Synuclein Inhibitors

Alpha-synuclein is a protein that, in humans, is encoded by the SNCA gene. An alpha-synuclein fragment, known as the non-Abeta component (NAC) of Alzheimer's disease amyloid, originally found in an amyloid-enriched fraction, was shown to be a fragment of its precursor protein, NACP. NACP is referred to as human alpha-synuclein.

Alpha synuclein defects and/or deficiencies are implicated in CNS disorders, such as Alzheimer's and Parkinson's diseases. Congenital defect or otherwise depletion of this protein is associated with increased oxidative stress and inflammation in the brain, which has been shown to directly contribute to the onset and progression of Alzheimer's and Parkinson's diseases, and other degenerative CNS disorders. The oxidative stress and inflammation lead to a depletion of glutathione and ascorbate in neurons and supporting cells. Therefore this therapy has the potential to reduce dosages of therapies associated with manipulating alpha-synuclein function or expression, thereby limiting exposure to toxic drug levels. Additionally, it can be used in conjunction with alpha-synuclein and other therapies to increase efficacy and/or decrease side effects.

Representative inhibitors include Posiphen and certain flavonoids.

Chelating Agents

Chelation describes a particular way that ions and molecules bind metal ions, namely, the formation or presence of two or more separate coordinate bonds between a polydentate (multiple bonded) ligand and a single central atom. Usually these ligands are organic compounds.

Chelating agents are used in chelation therapy to detoxify poisonous metal agents such as mercury, arsenic, and lead by converting them to a chemically inert form that can be excreted without further interaction with the body. In alternative medicine, chelation is used as a treatment for autism.

EDTA is also used in root canal treatment as an intracanal irrigant. EDTA softens the dentin which may improve access to the entire canal length and is used as an irrigant to assist in the removal of the smear layer.

Chelate complexes of gadolinium are often used as contrast agents in MRI scans.

Diuretics

Diuretics promote urine production, increasing water excretion. Antidiuretics such as vasopressin reduce water excretion in urine. Diuretics are used to treat heart failure, liver cirrhosis, hypertension and certain kidney diseases. Some diuretics, such as acetazolamide, help to make the urine more alkaline and are helpful in increasing excretion of substances such as aspirin in cases of overdose or poisoning.

Diuretics include high ceiling loop diuretics, such as furosemide, ethacrynic acid, torsemide, and furosemide; thiazides, carbonic anhydrase inhibitors such as acetazolamide and methazolamide, potassium-sparing diuretics, aldosterone antagonists, such as spironolactone, eplerenone, and potassium canreonate; epithelial sodium channel blockers such as amiloride and triamterene, calcium-sparing diuretics (thiazides are an example of such diuretics); osmotic diuretics, including glucose and mannitol, and low ceiling diuretics.

Alpha 1 Antitrypsin Modulators

Alpha-1 Antitrypsin or al-antitrypsin (A1AT) is a protease inhibitor which belongs to the serpin superfamily and is generally known as serum trypsin inhibitor. Alpha 1-antitrypsin is also referred to as alpha-1 proteinase inhibitor (A1PI) because it inhibits a wide variety of proteases. It protects tissues from enzymes of inflammatory cells, especially neutrophil elastase Recombinant A1PI include Prolastin, Zemaira, and Aralast.

Trypsin inhibitors include oxidoreductases, including Aldose reductase HMG-CoA reductase, 5-alpha-reductase, Monoamine oxidase, Dihydrofolate reductase, Lipoxygenase, Aromatase, COX-2, Xanthine oxidase, and Ribonucleotide reductase; Transferases, such as COMT, Thymidylate synthase, PARP, Dihydropteroate synthetase, Farnesyltransferase, GABA transaminase, Nucleotidyltransferase (Integrase Reverse transcriptase), Protein kinase (Tyrosine-kinase (Janus kinase)); Hydrolases, such as Phosphodiesterase, Acetylcholinesterase, Ribonuclease, Polygalacturonase, Neuraminidase, Alpha-glucosidase, Protease, Exopeptidase (Dipeptidyl peptidase-4, ACE), Endopeptidase (Trypsin, Renin, Matrix metalloproteinase), Histone deacetylase, and Beta-lactamase; and lyases, such as Dopa decarboxylase and Carbonic anhydrase.

Purinoceptor Agonists or Antagonists

Purinergic receptors, also known as purinoceptors, are a family of plasma membrane molecules that are found in almost all mammalian tissues. Purinergic receptors and signaling have been implicated in learning and memory, locomotor and feeding behavior, and sleep. More specifically, these receptors are involved in several cellular functions, including proliferation and migration of neural stem cells, vascular reactivity, apoptosis and cytokine secretion.

P2Y receptors are a family of purinergic G protein-coupled receptors, stimulated by nucleotides such as ATP, ADP, UTP, UDP and UDP-glucose. P2Y receptors are present in almost all human tissues where they exert various biological functions based on their G-protein coupling. P2Y2 is a potential drug target for treating cystic fibrosis. Studies have shown that activating purinoceptors in cystic fibrosis is a possible mechanism to alleviating inflammation and reducing infection. Accordingly, compounds that activate these receptors can be used in combination with the formulations described herein, which restore and/or maintain homeostasis in the mucosal membranes of the lungs of cystic fibrosis patients.

P2Y11 is a regulator of immune response, and a common polymorphism carried by almost 20% of North European Caucasians give increased risk of myocardial infarction, making P2Y11 an interesting drug target candidate for treatment of myocardial infarction.

P2Y12 is the target of the anti-platelet drug clopidogrel and other thienopyridines.

Modulators of these receptors can be used to treat cytotoxic edema, chronic pain, and diabetes. Representative modulators include clopidogrel, prasugrel and ticlopidine, as well as ticagrelor, all of which are antiplatelet agents that block P2Y12 receptors.

The compounds described herein can be used in combination with purinoceptor modulators to reduce dosages of these modulators, thereby limiting exposure to toxic drug levels. Additionally, they can be used in conjunction with other therapies to increase efficacy and/or decrease side effects.

Cyclooxygenase-2 (COX-2) Inhibitors

COX-2 selective inhibitors are a form of non-steroidal anti-inflammatory drug (NSAID) that directly target COX-2, an enzyme responsible for inflammation and pain. Targeting selectivity for COX-2 reduces the risk of peptic ulceration, and is the main feature of celecoxib, rofecoxib and other members of this drug class.

By combining the compounds described herein with COX-2 inhibitors, one can lower the dosage and/or reduce the side effects of these inhibitors.

Bactericidal and Bacteriostatic Agents ("Antibiotics")

Bactericidals kill bacteria directly, whereas bacteriostatics prevent them from dividing. However, these classifications are based on laboratory behavior. In practice, both can prevent a bacterial infection. They work through a variety of mechanisms (e.g., DNA gyrase inhibition, inhibiting bacterial cell wall synthesis, binding to the bacterial ribosomal subunits, and inhibiting protein synthesis). Some examples of the classes of antibiotics are multiple generations of cephalosporins, fluroquinolones, and aminoglycosides.

When the compounds described herein are used in conjunction with antibiotics, they can reduce dosages of the antibiotics, limiting exposure to toxic drug levels and/or the side effects associated with antibiotics (i.e., drug resistance and diarrhea), in some embodiments by helping wounded mucosal tissues to heal and/or resist further infection.

DNA Gyrase Inhibitors

DNA gyrase, often referred to simply as gyrase, is an enzyme that relieves strain while double-stranded DNA is being unwound by helicase. This causes negative supercoiling of the DNA. Bacterial DNA gyrase is the target of many antibiotics, including nalidixic acid, novobiocin, and ciprofloxacin. Two classes of antibiotics that inhibit gyrase are aminocoumarins (including novobiocin) and the quinolones (including nalidixic acid and ciprofloxacin).

Natural Killer Cell and Natural Killer T Cell Agonists or Antagonists

Natural killer cells (or NK cells) are a type of cytotoxic lymphocyte critical to the innate immune system. The role NK cells play is analogous to that of cytotoxic T cells in the vertebrate adaptive immune response. NK cells provide rapid responses to virally infected cells and respond to tumor formation, acting at around 3 days after infection. Typically immune cells detect MHC presented on infected cell surfaces, triggering cytokine release, causing lysis or apoptosis. NK cells can recognize stressed cells in the absence of antibodies and MHC, allowing for a much faster immune reaction. They were named "natural killers" because of the initial notion that they do not require activation in order to kill cells that are missing "self" markers of major histocompatibility complex (MHC) class 1.

Representative NK modulators include cortisol and histone deacetylase inhibitors (HDACs).

Cathepsin Class Agonists or Antagonists

Cathepsins are proteases which have a vital role in mammalian cellular turnover, including bone resorption. Cathepsins have been implicated in cancer, stroke, Alzheimer's disease, arthritis, Ebola, COPD, chronic periodontitis, pancreatitis, several ocular disorders: keratoconus, retinal detachment, age-related macular degeneration, and glaucoma.

Deficiencies in cathepsin A are linked to multiple forms of galactosialidosis. The cathepsin A activity in lysates of metastatic lesions of malignant melanoma is significantly higher than in primary focus lysates. Cathepsin A increased in muscles moderately affected by muscular dystrophy and denervating diseases.

Cathepsin B seems to actually break down the proteins that cause amyloid plaque, the root of Alzheimer's symptoms, and may even be a pivotal part of the natural defense against this disease used by people who do not get it. Overexpression of the encoded protein, which is a member of the peptidase C1 family, has been associated with esophageal adenocarcinoma and other tumors. Cathepsin B has also been implicated in the progression of various human tumors including ovarian cancer. Cathepsin B is also involved in apoptosis as well as degradation of myofibrillar proteins in myocardial infarction.

Cathepsin D (an aspartyl protease) appears to cleave a variety of substrates such as fibronectin and laminin. Unlike some of the other cathepsins, cathepsin D has some protease activity at neutral pH. High levels of this enzyme in tumor cells seems to be associated with greater invasiveness.

Cathepsin K is the most potent mammalian collagenase. Cathepsin K is involved in osteoporosis, a disease in which a decrease in bone density causes an increased risk for fracture. Osteoclasts are the bone resorbing cells of the body, and they secrete cathepsin K in order to break down collagen, the major component of the non-mineral protein matrix of the bone. Cathepsin K, among other cathepsins, plays a role in cancer metastasis through the degradation of the extracellular matrix. The genetic knockout for cathepsin S and K in mice with atherosclerosis was shown to reduce the size of atherosclerotic lesions. The expression of cathepsin K in cultured endothelial cells is regulated by shear stress. Cathepsin K has also been shown to play a role in arthritis.

Cathepsin activity has been shown to be modulated or enhanced by the concentrations of the components of this therapy. This therapy has the potential to reduce dosages of other therapies, thereby limiting exposure to toxic drug levels. Additionally, it can be used in conjunction with other therapies to increase efficacy and/or decrease side effects.

Cathepsin inhibitors, particularly cathepsin K inhibitors, have been used as anti-resorptives for treating osteoporosis, and also for use in treating arthritis, atherosclerosis, high blood pressure, obesity and cancer. One representative inhibitor is Ibandronic acid (INN) or ibandronate sodium (USAN), marketed under the trade name Boniva®.

Antioxidant Therapies

An antioxidant is a molecule that inhibits the oxidation of other molecules. Antioxidants terminate oxidation reactions by removing free radical intermediates, and inhibit other oxidation reactions. They do this by being oxidized themselves, so antioxidants are often reducing agents such as thiols, ascorbic acid, or polyphenols. Glutathione, cysteine, and N-acetyl cysteine are representative antioxidants, and additional antioxidants can be used.

Oxidative stress is thought to contribute to the development of a wide range of diseases, including Alzheimer's disease, Parkinson's disease, the pathologies caused by diabetes, rheumatoid arthritis, neurodegeneration in motor neuron diseases, and certain cancers (including those associated with reactive oxygen species, or "ROS."

Accordingly, antioxidant therapy can be used to treat, prevent, or reduce the severity of many diseases and conditions (e.g., cancers, cystic fibrosis, autoimmune disorders, organ transplants).

Rho-Associated Kinase Inhibitors

Rho-associated protein kinase (ROCK) is a kinase belonging to the AGC (PKA/PKG/PKC) family of serine-threonine kinases. It is mainly involved in regulating the shape and movement of cells by acting on the cytoskeleton.

ROCK signaling plays an important role in many diseases, including diabetes, neurodegenerative diseases, pulmonary hypertension, and cancer. ROCK inhibitors, such as arachadonic acid, can be used to treat these diseases, for example, potentially prevent cancer from spreading by blocking cell migration, stopping cancer cells from spreading into neighboring tissue.

Myosin Inhibitors

Myosins comprise a family of ATP-dependent motor proteins and are best known for their role in muscle contraction and their involvement in a wide range of other eukaryotic motility processes. Myosins function in a wide variety of cellular processes, from intracellular trafficking to cell motility, and are implicated in several human diseases (e.g., cancer, hypertrophic cardiomyopathy, deafness and many neurological disorders). Myosin inhibitors can therefore be used to treat these types of diseases. Representative myosin inhibitors include N-benzyl-p-toluene sulphonamide (BTS); 2,3-Butanedione monoxime (BDM); Pentachloropseudilin (PCIP); Pentabromopseudilin (PBP); MyoVin-1; and 2,4,6-Triiodophenol.

Phosphatidylinositol 3 Kinase Inhibitors and Related Molecules

Phosphatidylinositide 3-kinases (PI 3-kinases, PI3Ks, PI(3)Ks, or PI-3Ks) are a family of enzymes involved in cellular functions such as cell growth, proliferation, differentiation, motility, survival and intracellular trafficking, which in turn are involved in cancer.

Wortmannin and LY294002 are broad inhibitors against PI 3-kinases. Other representative PI 3 Kinase inhibitors include the class I PI 3-kinase, p110δ isoform specific inhibitors, IC486068 and IC87114 (ICOS Corporation), as well as GDC-0941 (Genentech), a highly selective inhibitor of p110α with little activity against mTOR.

Nitric Oxide Synthase Agonists or Antagonists, Nitric Oxide Agonists or Antagonists Nitric oxide synthases (NOSs) are a family of enzymes catalyzing the production of nitric oxide (NO) from L-arginine. NO is an important cellular signaling molecule. It helps modulate vascular tone, insulin secretion, airway tone, and peristalsis, and is involved in angiogenesis and neural development. Inhibitors of these enzymes can help treat stroke.

Representative NOS inhibitors include guanidino amino-acids, aminoguanidine, NG-iminoethyl-L-lysine (L-NIL), NG-iminoethyl-Lornithine (L-NIO), the bis-isothioureas (PBITU), 1400W (N-[3-(aminomethyl)benzyl]acetamidine), GW273629 and GW274150, 7-nitroindinazole (7-NI), tri(fluoromethylphenyl)imidazole (TRIM), ARL 17477, AR-R18512, BN 80933, S-ethyl and S-methyl thiocitrulline and vinyl L-NIO.

Ion Channel Function or Trafficking Modulators

Ion channels are pore-forming membrane proteins whose functions include establishing a resting membrane potential, shaping action potentials and other electrical signals by gating the flow of ions across the cell membrane, controlling the flow of ions across secretory and epithelial cells, and regulating cell volume.

Ion channels are present in the membranes of all cells. Ion channels are considered to be one of the two traditional classes of ionophoric proteins, with the other class known as ion transporters (including the sodium-potassium pump, sodium-calcium exchanger, and sodium-glucose transport proteins, amongst others).

Channels differ with respect to the ion they let pass (for example, Na+, K+, Cl−), the ways in which they may be regulated, the number of subunits of which they are composed and other aspects of structure.

Representative channel blockers include:

Tetrodotoxin (TTX), used by puffer fish and some types of newts for defense. It blocks sodium channels.

Saxitoxin, is produced by a dinoflagellate also known as "red tide." It blocks voltage dependent sodium channels.

Conotoxin, is used by cone snails to hunt prey.

Lidocaine and Novocaine belong to a class of local anesthetics which block sodium ion channels.

Dendrotoxin is produced by mamba snakes, and blocks potassium channels.

Iberiotoxin is produced by *Buthus tamulus* (Eastern Indian scorpion) and blocks potassium channels.

Heteropodatoxin is produced by *Heteropoda venatoria* (brown huntsman spider or laya) and blocks potassium channels.

CFTR is an ABC transporter-class ion channel that transports chloride and thiocyanate ions across epithelial cell membranes. Mutations of the CFTR gene affect functioning of the chloride ion channels in these cell membranes, leading to cystic fibrosis and congenital absence of the vas deferens. This therapy has the potential to reduce dosages of other therapies that facilitate the expression, transport, or function of CFTR, thereby limiting exposure to toxic drug levels. Additionally, it can be used in conjunction with these and other therapies to increase efficacy and/or decrease side effects.

Surfactant Therapies, in Particular, Lung (Pulmonary) Surfactants

Surfactants are compounds that lower the surface tension or interfacial tension between two liquids or between a liquid and a solid. Surfactants may act as detergents, wetting agents, emulsifiers, foaming agents, or dispersants.

Pulmonary surfactant are surface-active lipoprotein complexes (phospholipoprotein) formed by type II alveolar cells. The proteins and lipids that comprise the surfactant have both a hydrophilic region and a hydrophobic region. By adsorbing to the air-water interface of alveoli with the hydrophilic head groups in the water and the hydrophobic tails facing towards the air, the main lipid component of surfactant, dipalmitoylphosphatidylcholine (DPPC), reduces surface tension.

In the lungs, surfactant reduces the surface tension and helps to maximize the surface area available for gas exchange. Without adequate surfactant, a baby works much harder to breathe, becomes exhausted, and does not get enough oxygen. There are various pulmonary disorders associated with not having sufficient amounts of pulmonary surfactants, including infant respiratory distress syndrome (IRDS), hyaline membrane disease, congenital surfactant deficiency, and pulmonary alveolar proteinosis. Synthetic lung surfactants can be administered to overcome the deficiency. Perhaps the most widely-administered pulmonary surfactant is Curosurf® (Cornerstone Therapeutics).

When a lung surfactant is combined with the therapeutic agents described herein, the resulting therapy can reduce dosages of other therapies, thereby limiting exposure to toxic drug levels. Additionally, it can be used in conjunction with other therapies to increase efficacy and/or decrease side effects.

Cannabinoid Receptor Modulators

The cannabinoid receptors are a class of cell membrane receptors under the G protein-coupled receptor superfamily. Cannabinoid receptors are activated by three major groups of ligands, endocannabinoids (produced by the mammalian body), plant cannabinoids (such as THC, produced by the cannabis plant) and synthetic cannabinoids (such as HU-210).

Synthetic THC is prescribed today, under the INN dronabinol or the brand name Marinol, to treat vomiting and for enhancement of appetite, mainly in AIDS patients. Several synthetic cannabinoids have been shown to bind to the CB2 receptor with a higher affinity than to the CB1 receptor. Most of these compounds exhibit only modest selectivity. One of the described compounds, a classical THC-type cannabinoid, L-759,656, in which the phenolic group is blocked as a methyl ether, has a CB1/CB2 binding ratio >1000.

Certain tumors, especially gliomas, express CB2 receptors. Δ9-tetrahydrocannabinol and WIN-55,212-2, two nonselective cannabinoid agonists, induce the regression or eradication of malignant brain tumors in rats and mice. CB2 selective agonists are effective in the treatment of pain, various inflammatory diseases in different animal models, osteoporosis and atherosclerosis. CB1 selective antagonists have previously been used for weight reduction and smoking cessation. Activation of CB1 provides neuroprotection after brain injury.

Representative cannabinoid receptor modulators include Anandamide, N-Arachidonoyl dopamine, 2-Arachidonoylglycerol, 2-Arachidonyl glyceryl ether, Tetrahydrocannabinol, Epigallocatechin gallate (EGCG) 33, AM-1221 (1-[(N-methylpiperidin-2-yl)methyl]-2-methyl-3-(naphthalen-1-oyl)-6-nitroindole), AM-1235 (-[(5-fluoropentyl)-6-nitro-1H-indol-3-yl]-(naphthalen-1-yl)methanone), AM-2232 (5-(3-(1-naphthoyl)-1H-indol-1-yl)pentanenitrile), UR-144 ((1-pentylindol-3-yl)-(2,2,3,3-tetramethylcyclopropyl)methanone), JWH-007 (1-pentyl-2-methyl-3-(1-naphthoyl)indole), JWH-015 ((2-Methyl-1-propyl-1H-indol-3-yl)-1-naphthalenylmethanone) and JWH-018 (1-pentyl-3-(1-naphthoyl)indole) (Clemson University).

Complement System Inhibitors

The complement system is a biochemical cascade that attacks the surfaces of foreign cells. It contains over 20 different proteins and is named for its ability to "complement" the killing of pathogens by antibodies. Complement is the major humoral component of the innate immune response.

The complement system helps or "complements" the ability of antibodies and phagocytic cells to clear pathogens from an organism. It is part of the immune system (called the innate immune system) that is not adaptable and does not change over the course of an individual's lifetime. However, it can be recruited and brought into action by the adaptive immune system. It is thought that the complement system might play a role in many diseases with an immune component, such as Barraquer-Simons Syndrome, asthma, lupus erythematosus, glomerulonephritis, various forms of arthritis, autoimmune heart disease, multiple sclerosis, inflammatory bowel disease, paroxysmal nocturnal hemoglobinuria, atypical hemolytic uremic syndrome and ischemia-reperfusion injuries and rejection of transplanted organs. The complement system is also becoming increasingly implicated in diseases of the central nervous system such as Alzheimer's disease and other neurodegenerative conditions such as spinal cord injuries.

Deficiencies of the terminal pathway predispose to both autoimmune disease and infections (particularly *Neisseria meningitidis*, due to the role that the membrane attack complex plays in attacking Gram-negative bacteria). Recent research has suggested that the complement system is manipulated during HIV/AIDS to further damage the body.

Representative complement inhibitors include Soliris® (eculizumab, Alexion) which works by inhibiting the complement protein C5, which in turn acts at a relatively late stage in the complement cascade.

When complement inhibitors are combined with the therapeutic agents described herein, the combined therapy can reduce dosages of other therapies, thereby limiting exposure to toxic drug levels. Additionally, it can be used in conjunction with other therapies to increase efficacy and/or decrease side effects.

G Protein-Coupled Receptor Agonists or Antagonists

G protein coupled receptors (GPCRs), also known as seven-transmembrane domain receptors, 7TM receptors, heptahelical receptors, serpentine receptor, and G protein-linked receptors (GPLR), constitute a large protein family of receptors that sense molecules outside the cell and activate inside signal transduction pathways and, ultimately, cellular responses. An example of a GPCR is the cannabinoid receptors CBT and CB2.

The ligands that bind and activate these receptors include light-sensitive compounds, odors, pheromones, hormones, and neurotransmitters, and vary in size from small molecules to peptides to large proteins. G protein-coupled receptors are involved in many diseases, and are also the target of approximately 40% of all modern medicinal drugs. There are two principal signal transduction pathways involving the G protein-coupled receptors: the cAMP signal pathway and the phosphatidylinositol signal pathway. When a ligand binds to the GPCR it causes a conformational change in the GPCR, which allows it to act as a guanine nucleotide exchange factor (GEF). The GPCR can then activate an associated G-protein by exchanging its bound GDP for a GTP. The G-protein's α subunit, together with the bound GTP, can then dissociate from the β and γ subunits to further affect intracellular signaling proteins or target functional proteins directly depending on the α subunit type.

This therapy has the potential to reduce dosages of other therapies, thereby limiting exposure to toxic drug levels. Additionally, it can be used in conjunction with other therapies that modulate any or all components of GPCRs to increase efficacy and/or decrease side effects.

IgE Receptor Antagonists, G Protein-Coupled Receptor Agonists or Antagonists

Immunoglobulin E (IgE) is a class of antibody (or immunoglobulin (Ig) "isotype"). IgE exists as monomers consisting of two heavy chains (E chain) and two light chains, with the E chain containing 4 Ig-like constant domains (Cε1-Cε4). IgE's main function is immunity to parasites such as parasitic worms. IgE also plays an essential role in type I hypersensitivity, which manifests various allergic diseases, such as allergic asthma, allergic rhinitis, food allergy, and some types of chronic urticaria and atopic dermatitis. IgE also plays a pivotal role in allergic conditions, such as anaphylactic reactions to certain drugs, bee stings, and antigen preparations used in specific desensitization immunotherapy.

Currently, allergic diseases and asthma are usually treated with one or more of the following drugs: (1) antihistamines and antileukotrienes, which antagonize the inflammatory mediators histamine and leukotrienes, (2) local or systemic (oral or injectable) corticosteroids, which suppress a broad spectrum of inflammatory mechanisms, and (3) short or long-acting bronchodilators, which relax smooth muscle of constricted airway in asthma.

Chemokines, Chemokine Receptor Agonists or Antagonists

Chemokines are a family of small cytokines, or signaling proteins secreted by cells. Their name is derived from their ability to induce directed chemotaxis in nearby responsive cells; they are chemotactic cytokines. Some chemokines are considered pro-inflammatory and can be induced during an immune response to recruit cells of the immune system to a site of infection, while others are considered homeostatic and are involved in controlling the migration of cells during normal processes of tissue maintenance or development.

Chemokines have been classified into four main subfamilies: CXC, CC, CX3C and XC. All of these proteins exert their biological effects by interacting with G protein-linked transmembrane receptors called chemokine receptors, which are selectively found on the surfaces of their target cells. It has been suggested that blockage of chemokine function using chemokine inhibitors should not have a detrimental toxicological effect.

The cyclic peptide NR58-3.14.3 is a powerful anti-inflammatory agent, inhibiting inflammation in a number of disease models such as atherosclerosis, ischemia, lung disease, surgical adhesions, endometriosis, and pulmonary graft-versus-host disease. Cyclic peptide NR58-3.14.3 has also been shown to inhibit HIV replication.

Cytokines, and Cytokine Receptor Agonists or Antagonists

Cytokines such as tumor necrosis factor-a (TNF-a) and interleukin 1 (IL-1) are important mediators of inflammation and tissue damage in animal models of inflammatory arthritis and in patients with active rheumatoid arthritis (RA).

Inhibitors of these cytokines can be used to treat RA. Several widely used drugs, including corticosteroids, methotrexate, and cyclosporin A, are known to block cytokine production from macrophages and T cells. Representative inhibitors include Etanercept, is a recombinant fusion protein of the soluble type II TNF receptor on a human IgG1 backbone, infliximab, a chimeric anti-TNF-a monoclonal antibody containing a murine TNF-a binding region and human IgG1 backbone. Anakinra is a recombinant human IL-1 receptor antagonist (IL-1Ra) that binds avidly to type 1 IL-1 receptors but does not stimulate any intracellular responses.

Arachidonic Acid Agonists or Antagonists

Arachidonic acid (AA, sometimes ARA) is a polyunsaturated omega-6 fatty acid 20:4(ω-6). Flavonoids have been shown to have anti-inflammatory activity and to inhibitor arachidonic acid metabolism.

Inflammatory Mediators

Inflammation is part of the complex biological response of vascular tissues to harmful stimuli, such as pathogens, damaged cells or irritants. Inflammation is a protective attempt by the organism to remove the injurious stimuli and to initiate the healing process. However, inflammatory responses are often accompanied by unwanted side effects (e.g., histamine release during an allergic response causing sneezing).

Inflammatory mediators are soluble, diffusible molecules that act locally at the site of tissue damage and infection, and at more distant sites. They can be divided into exogenous and endogenous mediators.

Endogenous inflammatory mediators produced from within the (innate and adaptive) immune system itself, as well as other systems. Examples of endogenous inflammatory mediators are nitric oxide synthase agonists or antagonists, nitric oxide agonists or antagonists, arachidonic acid agonists or antagonists, histamine or leukotriene agonists or antagonists.

Bacterial products and toxins can act as exogenous inflammatory mediators, an example of which is endotoxin, or LPS of Gram-negative bacteria. Endotoxin can trigger complement activation, resulting in the formation of anaphylatoxins C3a and C5a which cause vasodilation and increase vascular permeability. Endotoxin also activates the Hageman factor, leading to activation of both the coagulation and fibrinolytic pathways as well as the kinin system. In addition, endotoxin elicit T cell proliferation, and have been described as superantigen for T cells.

Mononuclear phagocytes (monocytes and macrophages) are central to inflammation, as they produce many components which participate in or regulate the different plasma enzyme systems, and hence the mediators of the inflammatory response. They are also actively phagocytic and are involved in microbial killing, as are neutrophils. While the latter can be thought of as short-lived kamikaze cells that need to be continually replaced from the bone marrow, mononuclear phagocytes are long-lived and some can proliferate in situ. Other cells such as mast cells and basophils are much less phagocytic, but together with platelets, these cells are particularly important for secretion of vasoactive mediators. The function of these cell types is at least partially under the control of cytokines. All inflammatory cells have receptors for Fc domains of immunoglobulins and for complement components, and they possess specialized granules containing an immerse variety of products that are released perhaps by common mechanisms. Cytotoxic T lymphocytes and NK cells, in general, also possess granules which are important for their cytotoxic function. In general, lymphocytes are involved in the adaptive response to inflammation, and the early events of inflammation are mediated in part by molecules produced by cells of the innate arm of the immune system.

Early phase mediators are produced by mast cells and platelets. They are especially important in acute inflammation and include mainly histamine, serotonin and other vasoactive substances. Platelets may contribute to inflammatory responses resulting as a consequence of tissue injury, through a variety of mechanisms including the release of vasoactive amines and other permeability factors, the release of lysosomal enzymes, the release of coagulation factors which lead to localized and generalized fibrin deposition, and the formation of platelet aggregates or trombi which result in the blocking of vessels and capillaries. To the early phase mediators also belong chemoattractants (e.g. C5a) and cytokines such as IL-1, IL-6, and TNF-α.

Late phase mediators are responsible for the regulation of vascular events later—from about 6-12 hours after initiation of inflammation. The later vascular events are mediated, at least in part, by products of arachidonic acid.

When inflammatory mediators are combined with the therapeutic agents described herein, the combined therapy can reduce dosages of other therapies, thereby limiting exposure to toxic drug levels. Additionally, it can be used in conjunction with other therapies that modulate any or all components of GPCRs to increase efficacy and/or decrease side effects.

STAT6 Inhibitors

Interleukin-4 (IL-4) and IL-13 have a central role in the development of asthma through activation of the signal transducer and activator of transcription-6 (STAT6). STAT6 inhibitors can be used to treat asthma. Representative inhibitors include Vorinostat and other HDAC inhibitors.

Histamine or Leukotriene Agonists or Antagonists

Histamine is an organic nitrogen compound involved in local immune responses as well as regulating physiological function in the gut and acting as a neurotransmitter. Histamine triggers the inflammatory response.

Histamine affects mucous membranes in three main ways, including sneezing due to histamine-associated sensory neural stimulation, hyper-secretion from glandular tissue, and nasal congestion due to vascular engorgement associated with vasodilation and increased capillary permeability.

Histamine antagonists (or blockers) can be used to inhibit the inflammatory response associated with histamine, for treating allergy symptoms and preventing anaphylaxis.

H1-receptor antagonists (anti-histamines) are actually inverse agonists at the histamine H1-receptor. Clinically, H1 antagonists are used to treat allergic reactions. Examples include Acrivastine, Azelastine, Bilastine, Brompheniramine, Buclizine, bromodiphenhydramine, Carbinoxamine, Cetirizine (Metabolite of Hydroxyzine), Chlorpromazine (antipsychotic), Cyclizine, Chlorpheniramine, Chlorodiphenhydramine, Clemastine, Cyproheptadine, Desloratadine, Dexbrompheniramine, Dexchlorpheniramine, Dimenhydrinate (most commonly used as an antiemetic), Dimetindene, Diphenhydramine (Benadryl), Doxylamine (most commonly used as an OTC sedative), Ebastine, Embramine, Fexofenadine (Allegra), Hydroxyzine (Vistaril), Levocetirizine, Loratadine (Claritin), Meclozine (most commonly used as an antiemetic), Mirtazapine (primarily used to treat depression, also has antiemetic and appetite-stimulating effects), Olopatadine (used locally), Orphenadrine (a close relative of diphenhydramine used mainly as a skeletal muscle relaxant and anti-Parkinsons agent), Phenindamine, Pheniramine, Phenyltoloxamine, Promethazine, Pyrilamine, Quetiapine (antipsychotic; trade name Seroquel), Rupatadine, Tripelennamine, and Triprolidine.

H2-receptor antagonists are also inverse agonists and not true antagonists. They act on H2 histamine receptors found principally in the parietal cells of the gastric mucosa, which are part of the endogenous signaling pathway for gastric acid secretion. Normally, histamine acts on H2 to stimulate acid secretion; drugs that block H2 signaling thus reduce the secretion of gastric acid. H2 antagonists are among first-line therapy to treat gastrointestinal conditions including peptic ulcers and gastroesophageal reflux disease. Representative H2-receptor antagonists include Cimetidine, Famotidine, Lafutidine, Nizatidine, Ranitidine, and Roxatidine.

Calcineurin Agonists or Antagonists

Calcineurin (CN) is a protein phosphatase also known as protein phosphatase 3, and calcium-dependent serine-threonine phosphatase. It activates the T cells of the immune system, and can be blocked by drugs called calcineurin inhibitors. Representative compounds include cyclosporine, pimecrolimus and tacrolimus.

Calcineurin activates nuclear factor of activated T cell, cytoplasmic (NFATc), a transcription factor, by dephosphorylating it. The activated NFATc is then translocated into the nucleus, where it upregulates the expression of interleukin 2 (IL-2), which, in turn, stimulates the growth and differentiation of T cell response.

When an antigen-presenting cell interacts with a T cell receptor on T cells, there is an increase in the cytoplasmic level of calcium, which[3] activates calcineurin, by binding a regulatory subunit and activating calmodulin binding. Calcineurin induces different transcription factors (NFATs) that are important in the transcription of IL-2 genes. IL-2 activates T-helper lymphocytes and induces the production of other cytokines. In this way, it governs the action of cytotoxic lymphocytes. The amount of IL-2 being produced by the T-helper cells is believed to influence the extent of the immune response significantly.

Calcineurin antagonists can be used to treat rheumatic diseases, such as RA, alone or in combination with methotrexate, psoriatic arthritis, psoriasis, acute ocular Behçet's disease, juvenile idiopathic arthritis, adult and juvenile polymyositis and dermatomyositis, adult and juvenile systemic lupus erythematosus, adult lupus membranous nephritis, systemic sclerosis, aplastic anemia, steroid-resistant nephrotic syndrome, atopic dermatitis, severe ulcerative colitis, pemphigus vulgaris, myasthenia gravis, and dry eye disease, with or without Sjögren's syndrome.

Calcineurin is also linked to receptors for several brain chemicals including NMDA, dopamine and GABA, and inhibitors can be used to treat schizophrenia, impairment in working memory, attention deficits, aberrant social behavior, and several other abnormalities characteristic of schizophrenia.

Calcineurin along with NFAT, can improve the function of diabetics' pancreatic beta cells. Calcineurin/Nfat signaling is required for perinatal lung maturation and function.

Anti-HIV Agents

In some embodiments, the method comprises co-administration of an antiretroviral agent, and particularly an agent used for the treatment of HIV infection such as Zidovudine (AZT), Abacavir, Emtricitabine (FTC), Lamivudine (3TC), Didanosine (ddI), Stavudine (d4T), Zalcitabine (ddC), Nevirapine, Efavirenz, Delavirdine, Tenofovir, Enfuvirtide (T20), Maraviroc (CCR5), Lopinavir, Atazanavir, Fosamprenvir, Amprenavir, Saquinavir, Indinavir, Nelfinavir, Raltegravir, and Elvitegravir.

One or more, preferably one to four, antiviral agents useful in anti-HIV-1 therapy may be used. The antiviral agents contemplated for use comprise nucleoside and nucleotide reverse transcriptase inhibitors, non-nucleoside reverse transcriptase inhibitors, protease inhibitors and other antiviral drugs listed below not falling within these classifications. In particular, the combinations known as HAART are contemplated for use.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo-Wellcome Inc., Research Triangle, N.C. 27709; didanosine (ddI) available under the VIDEX tradename from Bristol-Myers Squibb Co., Princeton, N.J. 08543; zalcitabine (ddC) available under the HMD tradename from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR tradename from Glaxo-Smith Kline Triangle, N.C. 27709; abacavir (1592U89) disclosed in WO96/30025 and available under the ZIAGEN trademark from Glaxo-Wellcome Research Triangle, N.C. 27709; adefovir dipivoxil [bis(POM)-PMEA] available under the PREVON tradename from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(−)-FTC] available from Gilead under the trade name Emtriva™; beta-L-FD4 (also called beta-L-D4C and named beta-L-2',3'-dicleoxy-5-fluoro-cytidene) (Vion Pharmaceuticals, New Haven Conn. 0651 1); DAPD, the purine nucleoside, (−)-beta-D-2,6,-diamino-purine dioxolane disclosed in EP 0656778 (Triangle Pharmaceuticals, Durham, NC); and lodenosine (FddA), 9-(2,3-dideoxy-2-fluoro-b-D-threo-pentofuranosyl) adenine, an acid stable purine-based reverse transcriptase inhibitor under development by U.S. Bioscience Inc., West Conshohoken, Pa. 19428. The term "non-nucleoside reverse transcriptase inhibitors" ("NNRTI1S) as used herein means non-nucleosides that inhibit the activity of HIV-1 reverse transcriptase.

Typical suitable NNRTIs include nevirapine (BI-RG-587) available under the VIRAMUNE tradename from Boehringer Ingelheim, the manufacturer for Roxane Laboratories, Columbus, Ohio 43216; delaviradine (BHAP, U-90152) available under the RESCRIPTOR tradename from Pharmacia & Upjohn Co., Bridgewater N.J. 08807; efavirenz (DMP-266) a benzoxazin-2-one disclosed in WO94/03440 and available under the SUSTIVA tradename from Bristol Myers Squibb in the US and Merck in Europe; PNU-142721, a furopyridine-thio-pyrimide under development by Pharmacia and Upjohn, Bridgewater N.J. 08807; AG-1549 (formerly Shionogi #S-1153); 5-(3,5-dichlorophenyl)-thio-4-isopropyl-1-(4-pyridyl)methyl-1H-imidazol-2-ylmethyl carbonate disclosed in WO 96/10019 and under clinical development by Agouron Pharmaceuticals, Inc., LaJolla Calif. 92037-1020; MKC-442 (1-(ethoxy-methyl)-5-(1-methylethyl)-6-(phenylmethyl)-(2,4(1H,3H)-pyrimidinedione) discovered by Mitsubishi Chemical Co. and under development by Triangle Pharmaceuticals, Durham, N.C. 27707; (+)-calanolide A (NSC-675451) and B, coumarin derivatives disclosed in NIH U.S. Pat. No. 5,489,697, licensed to Med Chem Research, which is co-developing (+) calanolide A with Vita-Invest as an orally administrable product; and etravirine (TMC-125, Intelence) marketed by Tibotec.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN (available from Merck) as well as nonpeptide protease inhibitors e.g., VIRACEPT (available from Agouron).

Typical suitable PIs include saquinavir (Ro 31-8959) available in hard gel capsules under the INVIRASE tradename and as soft gel capsules under the FORTOVASE tradename from Roche Pharmaceuticals, Nutley, N.J. 07110-1199; ritonavir (ABT-538) available under the NORVIR tradename from Abbott Laboratories, Abbott Park, Ill. 60064; indinavir (MK-639) available under the CRIXIVAN tradename from Merck & Co., Inc., West Point, Pa. 19486-0004; nelfnavir (AG-1343) available under the VIRACEPT tradename from Agouron Pharmaceuticals, Inc., LaJolla Calif. 92037-1020; amprenavir (141W94), tradename AGENERASE, a non-peptide protease inhibitor under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; AG-1549 an orally active imidazole carbamate discovered by Shionogi (Shionogi #S-1153) and under development by Agouron Pharmaceuticals, Inc., LaJolla Calif. 92037-1020; atazanavir; tipranavir; and darunavir.

Other antiviral agents include CXCR4 antagonists, enfuvirtide, hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename from Chiron Corp., Emeryville, Calif. 94608-2997 as a lyophilized powder for IV infusion or sc administration upon reconstitution and dilution with water; a dose of about 1 to about 20 million ILJ/day, sc is preferred;

a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Enfuvirtide (DP-178, T-20) a 36-amino acid synthetic peptide, is disclosed in U.S. Pat. No. 5,464,933; enfuvirtide acts by inhibiting fusion of HIV-1 to target membranes. Enfuvirtide (3-100 mg/day) is given as a continuous sc infusion or injection together with efavirenz and 2 Pi's to HIV-1 positive subjects refractory to a triple combination therapy; use of 100 mg/day is preferred. Yissum Project No. 11607, a synthetic protein based on the HIV-1 Vif protein, is under development by Yissum Research Development Co., Jerusalem 91042, Israel. Ribavirin, 1-.beta.-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771; the integrase inhibitor raltegravir available from Merck under the tradename Isentress™; elvitegravir an intergrase inhibitor under development by Gilead Sciences; the HIV-1Gag maturation inhibitor berivimat under development (Phase lib) by Panacos Pharmaceuticals.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include: (a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one NNRTI or two NRTIs and one PI is preferred if there is intolerance to NNRTI. Drug compliance is essential. The CD4+ and HIV-1-RNA plasma levels should be monitored every 3-6 months. Should viral load plateau, a fourth drug, e.g., one PI, one NNRTI or integrase inhibitor could be added.

Particularly where the compositions include these additional therapeutic agents, the compositions can be used to treat mucosal diseases, pulmonary diseases, autoimmune diseases (including multiple sclerosis, Crohn's disease, ulcerative colitis, lupus, inflammatory bowel syndrome, irritable bowel syndrome, etc.), infectious diseases (e.g., HIV), Alzheimer's disease, and the like.

The compositions and formulations of this invention can be administered to an immunocompromised subject, a transplant recipient, a subject undergoing chemotherapy, a subject at increased risk of an opportunistic infection, a subject infected by HIV, a subject that has acquired immunodeficiency syndrome (AIDS), etc., in order to treat and/or prevent diseases and disorders associated with such an immunocompromised or vulnerable status (e.g., *Pneumocystis jirovecii* pneumonia (PCP), cytomegalovirus (CMV) infection, *Mycobacterium avium-intracellulare* (MAI or MAC) infection, infection by *Mycobacterium* other than tuberculosis (MOTT), etc.). The compositions and formulations of this invention can be administered in an amount that restores and/or maintains a homeostatic environment in the mucosal membranes of such a subject to treat, prevent or reduce the severity of PCP, CMV infection, MAI infection, MOTT infection and the like.

In some aspects of these embodiments, a single formulation includes the therepautic agent(s) and the glutathione, organic acid and buffer, and in other aspects of these embodiments, the therapeutic agents are present in a first formulation and the glutathione, organic acid and buffer are present in a second formulation. As such, the compositions can be used in combination or 'kit' therapies. The formulation with the therapeutic agent can be present in oral, injectable, or inhaled forms, and the glutathione, organic acid and buffer present in an inhaled (e.g., pulmonary or intranasal) formulation.

Where the therapeutic agent is present, the resulting new formulations can provide new applications for the therapeutic agent, enhance the efficacy of the therapeutic agent, reduce unwanted side effects associated with the therapeutic agent, and/or reduce the dose of the therapeutic agent.

While not wishing to be bound by a particular theory, it is believed that the formulations disclosed herein are effective in achieving and maintaining either a normal lung mucosa, or at least a more normal lung mucosa, which is an important factor in maintaining lung health. Drugs administered to the lungs are often associated with certain side effects, in some cases because of dosage, and in other cases because they damage the lung tissue. In some embodiments, therapeutic agents combined with the formulations disclosed herein are effective at lower doses, and at such lower doses, the incidence of side effects can be reduced. In other embodiments, where the therapeutic agent interacts unfavorably with lung tissue, the formulations described herein can help to restore homeostasis to the lung tissue, and thus help minimize or eliminate damage caused by the therapeutic agents.

Representative therapeutic agents that can be combined with the compositions and formulations of this invention include, but are not limited to, Fluticasone (for example, sold as Flovent diskus 50 or as Flonase, GlaxoSmithKline), Budesonide (for example, sold as Pulmicort respules or Rhinocort by Astra Zeneca ("AZ"), Mometasone (sold as Nasonex as a spray, or as Asmanex Twisthaler by Merck/S-P), Ciclesonide (sold as Alvesco or Omnaris by Takeda Pharmaceuticals), Flunisolide (sold as Aerobid by Roche Palo or by Aerospan HFA by GSK), Beclomethasone (sold as Qvar or Onasl by Teva Pharmaceuticals), Albuterol (sold as ProAir HFA by Teva and as Ventolin HFA by GSK), Levalbuterol (sold as Xopenex by Sunovion), Ipratropium (sold as Atrovent by BI), Tiotropium (sold as Spiriva by BI), Salmeterol (sold as Serevent by GSK), Formoterol (sold as Foradil by Novartis and as Perforomist by Dey Pharma), Arformoterol (sold as Brovana by Sunovion), Indacaterol (sold as Arcapta by Novartis), Aclidinium (sold as Tudorza by Forest Labs), Pirbuterol (sold as Maxair by Medicis).

To treat pulmonary infections, the formulations described herein can be combined with antibiotics, whether in the same inhaled formulation (i.e., via pulmonary delivery or intranasal delivery), or where the antibiotics are administered by another route, such as the oral or injectable routes. Representative antibiotics useful in treating pulmonary infections include, but are not limited to, penicillins such as Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, and Ticarcillin, and combinations of penicillins with other therapeutic agents, such as Amoxicillin/clavulanate, Ampicillin/sulbactam, Piperacillin/tazobactam, and Ticarcillin/clavulanate.

For treating infections such as tuberculosis, combination therapy may include one or more of the following agents: rifampicin, rifabutin, isoniazid, streptomycin, pyrazinamide, and ethambutol. Pyridoxine (vitamin B6) (25-50 mg daily or 50-100 mg twice weekly) can be administered to patients undergoing TB treatment with isoniazid, to reduce the occurrence of isoniazid-induced side effects in the central and peripheral nervous system.

For individuals traveling to areas with a high incidence of tuberculosis, health care providers likely to come into contact with tuberculosis patients, or HIV-infected patients at increased risk for catching tuberculosis, preventative therapy may be desired. Patients undergoing preventive treatment for TB can optionally receive a periodic, for example, a monthly clinical evaluation of their adherence to treatment and medication side effects.

In one embodiment, the preventive therapy regimens include the use of a combination of at least two antituberculosis drugs to which the infecting strain is believed to be susceptible (e.g., rifabutin or rifampicin, in combination with ethambutol pyrazinamide, levofloxacin or ethambutol). The clinician can review the drug-susceptibility pattern of the *M. tuberculosis* strain isolated from the infecting source-patient before choosing a preventive therapy regimen. When combined with the formulations described herein, the patient's lungs will be at optimal levels of homeostasis, and thus less likely to become infected, particularly when a preventative antibiotic formulation is co-administered.

Drug Delivery Systems

The compositions described herein can be administered in any of a variety of drug delivery systems, depending on the intended area in which the compounds are to be administered. Representative drug delivery systems include, but are not limited to, the following: eye drops, nebulizers, topical gels and ointments, dry powders, particles, sprays, liquids, anesthetic machines or vaporizers, autoinjectors, intrauterine devices, respimats, liniments, liposomes, lotions, formulations for intramuscular, intrathecal, or subcutaneous injection, douches, infusions, and face masks. Exemplary formulations are described in more detail below.

Formulations for Pulmonary Delivery

In some embodiments, the pharmaceutical compositions of this invention are adapted to be administered to the lower respiratory tract (e.g., the lungs) directly through the airways by inhalation. Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition of the invention may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360 and 5,590,645 (all illustrating the "Diskus" device), or GB2i78965, GB2129691, GB2169265, U.S. Pat. Nos. 4,778,054, 4,811,731 and 5,035,237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurized packs, such as a metered dose inhaler (MDI), with the use of a suitable liquefied propellant. The medication in pressurized MDI is most commonly stored in solution in a pressurized canister that contains a propellant, although it may also be a suspension.

Aerosol compositions suitable for inhalation can be presented either as suspensions or as solutions and typically contain the active compound and a suitable propellant such as a fluorocarbon or hydrogen-containing chlorofluorocarbon or mixtures thereof, particularly hydrofluoroalkanes such as dichiorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof.

The aerosol composition may optionally contain additional excipients typically associated with such compositions, for example, surfactants such as oleic acid or lecithin and co-solvents such as ethanol. Pressurized formulations will generally be contained within a canister (for example an aluminum canister) closed with a metering valve and fitted into an actuator provided with a mouthpiece.

Medicaments for administration by inhalation typically have a controlled particle size. The optimum particle size for inhalation into the bronchial system is usually about 1 to about 10 μm, and in some embodiments, from about 2 to about 5 μm. Particles having a size above about 20 μm are generally too large when inhaled to reach the small airways. To achieve these particle sizes the particles of the active ingredient may be subjected to a size reducing process such as micronization. The desired size fraction may be separated out by air classification or sieving. Preferably, the particles will be crystalline. When an excipient such as lactose is employed, typically the particle size of the excipient will be much greater than the particle size of the active ingredient.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical compositions of this invention can be formulated with supplementary active ingredients. In some embodiments, the supplementary active ingredients are anti-inflammatory agents or inhaled steroids, corticosteroids cysteinyl-leukotriene receptor antagonist and cromolyn and or bronchodilators such as $\beta_2$ agonists and/or anticholinergics. Some inhaled steroids may include Dexamethasone, Budesonide (PULMICORT®), Fluticasone (FLOVENT®), Ciclesonide (ALVESCO®), Beclomethasone Dipropionate (QVAR®) or others known in the art. $\beta_2$ agonists may include salbutamol, albuterol, terbutaline, salmeterol, or formoterol. An anticholinergic may include Ipratropium.

In some embodiments, the pharmaceutical composition of this invention is administered from a dry powder inhaler.

In other embodiments, the pharmaceutical composition of this invention is administered by an aerosol dispensing device, optionally in conjunction with an inhalation chamber such as the "Volumatic"® inhalation chamber.

The carrier can be a solvent or dispersion medium containing, for example, water, ethanol, polyol (for example, glycerol, propylene glycol and liquid polyethylene glycol, and the like), suitable mixtures thereof, and/or vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a pharmaceutical composition of this invention can be within a matrix which controls the release of the composition. In some embodiments, the matrix can comprise lipid, polyvinyl alcohol, polyvinyl acetate, polycaprolactone, poly(glycolic)acid, poly(lactic) acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly (ortho esters), sucrose acetate isobutyrate (SAIB), and combinations thereof and other polymers such as those disclosed, for example, in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. In these embodiments, the matrix sustainedly releases the drug.

Pharmaceutically acceptable carriers and/or diluents may also include any and all solvents, dispersion media, coatings, antibacterials and/or antifungals, isotonic and absorption delaying agents and the like. The use of such media and agents for pharmaceutically active substances is well known in the art. Except insofar as any conventional medium or agent is incompatible with the active ingredient, use thereof in the pharmaceutical compositions is contemplated.

The pharmaceutical compositions of this invention can optionally comprise one or more additional components, such as, but not limited to, carriers, excipients, viscosity-increasing agents, preservers, stabilizers, anti-oxidants, binders, disintegrants, humectants, lubricants, colorants, flavoring agents, corrigents, suspend molding agents, emulsifying agents, solubilizers, buffering agents, tonicity agents, detergents, soothing agents, sulfur-containing reducing agents, etc.

The pharmaceutical compositions of the present invention can be formulated for administration in accordance with conventional techniques. See, e.g., Remington, The Science and Practice of Pharmacy (20$^{th}$ Ed. 2000). For example, the intranasal pharmaceutical compositions of the present invention can be formulated as an aerosol (this term includes both liquid and dry powder aerosols). Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles (e.g., lyophilized, freeze dried, etc.) can likewise be produced with any solid particulate medicament aerosol generator, by techniques known in the pharmaceutical art. As another example, the pharmaceutical compositions of the present invention can be formulated as an on-demand dissolvable form, which provides a lyophilized portion of the pharmaceutical composition and a dissolving solution portion of the pharmaceutical composition.

In some embodiments of the present invention, the pharmaceutical composition is in the form of an aqueous suspension, which can be prepared from solutions or suspensions. With respect to solutions or suspensions, dosage forms can be comprised of micelles of lipophilic substances, liposomes (phospholipid vesicles/membranes) and/or a fatty acid (e.g., palmitic acid). In particular embodiments, the pharmaceutical composition is a solution or suspension that is capable of dissolving in the fluid secreted by mucous membranes of the epithelium of the tissue to which it is administered, applied and/or delivered, which can advantageously enhance absorption.

The pharmaceutical composition can be an aqueous solution, a nonaqueous solution or a combination of an aqueous and nonaqueous solution.

Suitable aqueous solutions include, but are not limited to, aqueous gels, aqueous suspensions, aqueous microsphere suspensions, aqueous microsphere dispersions, aqueous liposomal dispersions, aqueous micelles of liposomes, aqueous microemulsions, and any combination of the foregoing, or any other aqueous solution that can dissolve in the fluid secreted by the mucosal membranes of the nasal cavity. Exemplary nonaqueous solutions include, but are not limited to, nonaqueous gels, nonaqueous suspensions, nonaqueous microsphere suspensions, nonaqueous microsphere dispersions, nonaqueous liposomal dispersions, nonaqueous emulsions, nonaqueous microemulsions, and any combination of the foregoing, or any other nonaqueous solution that can dissolve or mix in the fluid secreted by mucosal membranes.

Examples of powder formulations include, without limitation, simple powder mixtures, micronized powders, freeze dried powder, lyophilized powder, powder microspheres, coated powder microspheres, liposomal dispersions, and any combination of the foregoing. Powder microspheres can be formed from various polysaccharides and celluloses, which include without limitation starch, methylcellulose, xanthan gum, carboxymethylcellulose, hydroxypropyl cellulose, carbomer, alginate polyvinyl alcohol, acacia, chitosans, and any combination thereof.

In particular embodiments, the composition is one that is at least partially, or even substantially (e.g., at least 80%, 90%, 95% or more) soluble in the fluids that are secreted by mucosa so as to facilitate absorption. Alternatively or additionally, the composition can be formulated with a carrier and/or other substances that foster dissolution of the agent within secretions, including without limitation fatty acids (e.g., palmitic acid), gangliosides (e.g., GM-1), phospholipids (e.g., phosphatidylserine), and emulsifiers (e.g., polysorbate 80).

Those skilled in the art will appreciate that for intranasal administration or delivery, because the volume of the pharmaceutical composition administered is generally small, nasal secretions may alter the pH of the administered dose since the range of pH in the nasal cavity can be as wide as 5 to 8. Such alterations can affect the concentration of un-ionized drug available for absorption. Accordingly, in representative embodiments, the pharmaceutical composition further comprises a buffer to maintain or regulate pH in situ. Typical buffers include, but are not limited to, ascorbate, acetate, citrate, prolamine, carbonate, and phosphate buffers.

In embodiments of the invention, the pH of the pharmaceutical composition is selected so that the internal environment of the mucosal tissue after administration is on the acidic to neutral side, which (1) can provide the active compound in an un-ionized form for absorption, (2) prevents growth of pathogenic bacteria, which is more likely to occur in an alkaline environment, and (3) reduces the likelihood of irritation of the mucosa.

For liquid and powder sprays or aerosols, the pharmaceutical composition can be formulated to have any suitable and desired particle or droplet size. In illustrative embodiments, the majority and/or the mean size of the particles or droplets range from equal to or greater than about 1, 2.5, 5, 10, 15 or 20 microns and/or equal to or less than about 25, 30, 40, 45, 50, 60, 75, 100, 125, 150, 175, 200, 225, 250, 275, 300, 325, 350, 375, 400, or 425 microns (including all combinations of the foregoing). Representative examples of suitable ranges for the majority and/or mean particle or droplet size include, without limitation, from about 5 to 100 microns, from about 10 to 60 microns, from about 175 to 325 microns, and from about 220 to 300 microns which facilitate the deposition of an effective amount of the active compound, for example, in the nasal cavity (e.g., in the upper third of the nasal cavity, the superior meatus, the olfactory region and/or the sinus region to target the olfactory neural pathway). In general, particles or droplets smaller than about 5 microns will be deposited in the trachea or even the lung, whereas particles or droplets that are about 50 microns or larger generally do not reach the nasal cavity and are deposited in the anterior nose.

International patent publication WO 2005/023335 (Kurve Technology, Inc.) describes particles and droplets having a diameter size suitable for the practice of representative embodiments of the present invention. For example, the particles or droplets can have a mean diameter of about 2 to 50 microns, about 5 to 50 microns, about 5 to 40 microns, about 5 to 35 microns, about 5 to 30 microns, about 5 to 20 microns, about 5 to 17 microns, about 5 to 30 microns, about 10 to 25 microns, about 10 to 15 microns, about 11 to 50 microns, about 11 to 30 microns, about 11 to 20 microns, about 11 to 15 microns, about 12 to 17 microns, about 15 to 25 microns, about 15 to 27 microns or about 17 to 23 microns.

In particular embodiments, the particles or droplets have a mean diameter of about 5 to 30 microns, about 10 to 20 microns, about 10 to 17 microns, about 10 to 15 microns, about 12 to 17 microns, about 10 to 15 microns or about 10 to 12 microns.

Further, the particles or droplets can have a mean diameter of about 10 to 20 microns, about 10 to 25 microns, about 10 to 30 microns, or about 15 to 30 microns.

The particles can "substantially" have a mean diameter or size as described herein, i.e., at least about 50%, 60%, 70%, 80%, 90% or 95 or more of the particles are of the indicated diameter or size range.

The pharmaceutical composition of this invention can be delivered as a nebulized or atomized liquid having a droplet size as described above.

In some embodiments, the pharmaceutical composition is isotonic to slightly hypertonic, e.g., having an osmolarity ranging from about 150 to 550 mOsM. In other embodiments, the pharmaceutical composition is isotonic, having, e.g., an osmolarity ranging from approximately 150 to 350 mOsM.

According to particular embodiments of this invention that comprise methods of intranasal delivery, it can be desirable to prolong the residence time of the pharmaceutical composition in the nasal cavity (e.g., in the upper third of the nasal cavity, the superior meatus, the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl), which are agents that enhance residence time in the nasal cavity. As a further approach, increasing the viscosity of the formulation can also provide a means of prolonging contact of the agent with the nasal epithelium. The pharmaceutical composition can be formulated as a nasal emulsion, ointment or gel, which offers advantages for local application because of their viscosity.

Moist and highly vascularized membranes can facilitate rapid absorption; consequently, the pharmaceutical composition can optionally comprise a humectant, particularly in the case of a gel-based composition so as to assure adequate intranasal moisture content. Examples of suitable humectants include but are not limited to glycerin or glycerol, mineral oil, vegetable oil, membrane conditioners, soothing agents, and/or sugar alcohols (e.g., xylitol, sorbitol; and/or mannitol). The concentration of the humectant in the pharmaceutical composition will vary depending upon the agent selected and the formulation.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In representative embodiments, the preservative is present in an amount of about 2% by weight or less.

The pharmaceutical compositions described herein can optionally contain an odorant, e.g., as described in EP 0 504 263 B1, to provide a sensation of odor, to aid in inhalation of the composition so as to promote delivery to the olfactory region and/or to trigger transport by the olfactory neurons.

As another option, the composition can comprise a flavoring agent, e.g., to enhance the taste and/or acceptability of the composition to the subject.

Porous Particles for Pulmonary Administration

In one embodiment, the particles are porous, so that they have an appropriate density to avoid deposition in the back of the throat when administered via an inhaler. The combination of relatively large particle size and relatively low density avoids phagocytosis in the lungs, provides appropriately targeted delivery, avoids systemic delivery of the components, and provides a high concentration of the components in the lung.

Representative methods for preparing such particles, and for delivering such particles, are described, for example, in U.S. Pat. No. 7,384,649, entitled, "Particulate compositions for pulmonary delivery," U.S. Pat. No. 7,182,961, entitled "Particulate compositions for pulmonary delivery," U.S. Pat. No. 7,146,978, entitled, "Inhalation device and method," U.S. Pat. No. 7,048,908, entitled "Particles for inhalation having sustained release properties," U.S. Pat. No. 6,956,021, entitled "Stable spray-dried protein formulations," U.S. Pat. No. 6,766,799, entitled "Inhalation device," and U.S. Pat. No. 6,732,732, entitled "Inhalation device and method."

Additional patents disclosing such particles include U.S. Pat. No. 7,279,182, entitled "Formulation for spray-drying large porous particles," U.S. Pat. No. 7,252,840, entitled "Use of simple amino acids to form porous particles," U.S. Pat. No. 7,032,593, entitled "Inhalation device and method," U.S. Pat. No. 7,008,644, entitled "Method and apparatus for producing dry particles," U.S. Pat. No. 6,848,197, entitled "Control of process humidity to produce large, porous particles," and U.S. Pat. No. 6,749,835, entitled "Formulation for spray-drying large porous particles."

U.S. Pat. No. 7,678,364, entitled "Particles for inhalation having sustained release properties," discloses methods for delivering particles to the pulmonary system comprising: administering to the respiratory tract of a patient in need of treatment, prophylaxis or diagnosis an effective amount of a dry powder comprising: a) a multivalent metal cation which is complexed with a therapeutic, prophylactic or diagnostic agent; b) a pharmaceutically acceptable carrier; and c) a multivalent metal cation-containing component wherein the dry powder is spray-dried and has a total amount of multivalent metal cation which is about 10% w/w or more of the total weight of the agent, a tap density of about 0.4 g/cm$^3$ or less, a median geometric diameter of from about 5 micrometers to about 30 micrometers and an aerodynamic diameter of from about 1 to about 5 microns.

Delivery of bioactive agents to the pulmonary system typically results in rapid release of the agent following administration. For example, Further, Heinemann, Traut and Heise teach in *Diabetic Medicine* 14:63-72 (1997) that the onset of action, assessed by glucose infusion rate, in healthy volunteers after inhalation was rapid with the half-maximal action reached in about 30 minutes. That said, the formulation can be prepared so that the components are released into the lungs in a sustained fashion.

Particles suitable for inhalation can be designed to possess a sustained release profile. This sustained released profile provides for prolonged residence of the administered components in the lung and thereby, increases the amount of time in which therapeutic levels of the components are present in the local environment. Consequently, patient compliance and comfort can be increased by not only reducing frequency of dosing, but by providing a therapy which is more amenable and efficacious to patients.

The particles comprise a pharmaceutically acceptable carrier. Suitable pharmaceutically acceptable carriers can be chosen, for example, based on achieving particles having the proper characteristics for inhalation to the area of the respiratory tract where delivery is desired and therapeutic action is achieved.

In a preferred embodiment of the invention, the pharmaceutically acceptable carrier is a phospholipid. The phospholipid can be present in the particles in an amount ranging from about 0 to about 90 weight %. More commonly it can be present in the particles in an amount ranging from about 10 to about 60 weight %. Examples of suitable phospholipids include, among others, phosphatidic acids, phosphatidylcholines, phosphatidylalkanolamines such as a phosphatidylethanolamines, phosphatidylglycerols, phosphatidylserines, phosphatidylinositols and combinations thereof. Other phospholipids are known to those skilled in the art and are described in U.S. patent application Ser. No. 09/752,109 entitled "Particles for Inhalation Having Sustained Release Properties" filed on Dec. 29, 2000 and U.S. patent application Ser. No. 09/752,106 entitled "Particles for Inhalation Having Sustained release Properties" filed on Dec. 29, 2000 the contents of all of which are incorporated herein in their entirety. In a preferred embodiment, the phospholipids are endogenous to the lung.

The phospholipids can be selected to impart controlled release properties to the highly dispersible particles. The phase transition temperature of a specific phospholipid can be below, around or above the physiological body temperature of a patient. Preferred phase transition temperatures range from 30 to 50° C., (e.g., within +/−10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of active agent can be slowed down. On the other hand, rapid release can be obtained by including in the particles phospholipids having lower transition temperatures. Particles having controlled release properties and methods of modulating release of a biologically active agent are described in U.S. patent application Ser. No. 09/644,736 entitled Modulation of Release From Dry Powder Formulations by Controlling Matrix Transition, filed on Aug. 23, 2000, the entire contents of which are incorporated herein by reference.

The amount of the glutathione, ascorbic acid or salt thereof, and sodium bicarbonate present in the particles can range from about 0.1 weight % to about 95 weight %, though in some cases, can even be as high as 100%. For example, from about 1 to about 50%, such as from about 5 to about 30%. Particles in which the drug is distributed throughout a particle can be preferred.

In a further embodiment, the particles can also include other excipients such as, for example, buffer salts, dextran, polysaccharides, lactose, trehalose, cyclodextrins, proteins, polycationic complexing agents, peptides, polypeptides, fatty acids, fatty acid esters, inorganic compounds, phosphates.

In one embodiment, the particles can further comprise polymers. Biocompatible or biodegradable polymers are preferred. Such polymers are described, for example, in U.S. Pat. No. 5,874,064, issued on Feb. 23, 1999 to Edwards et al., the teachings of which are incorporated herein by reference in their entirety.

In yet another embodiment, the particles include a surfactant other than the phospholipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles of the invention include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85); Tween 80 and tyloxapol.

The surfactant can be present in the particles in an amount ranging from about 0 to about 5 weight %. Preferably, it can be present in the particles in an amount ranging from about 0.1 to about 1.0 weight %.

The particles, also referred to herein as powder, can be in the form of a dry powder suitable for inhalation. In a particular embodiment, the particles can have a tap density of less than about 0.4 g/cm$^3$. Particles which have a tap density of less than about 0.4 g/cm$^3$ are referred to herein as "aerodynamically light particles." More preferred are particles having a tap density less than about 0.1 g/cm$^3$.

Aerodynamically light particles have a preferred size, e.g., a volume median geometric diameter (VMGD) of at least about 5 microns (μm). In one embodiment, the VMGD is from about 5 μm to about 30 μm. In another embodiment of the invention, the particles have a VMGD ranging from about 9 μm to about 30 μm. In other embodiments, the particles have a median diameter, mass median diameter (MMD), a mass median envelope diameter (MMED) or a mass median geometric diameter (MMGD) of at least 5 μm, for example from about 5 μm to about 30 μm.

Aerodynamically light particles preferably have "mass median aerodynamic diameter" (MMAD), also referred to herein as "aerodynamic diameter," from about 1 μm to about 5 μm. In one embodiment of the invention, the MMAD is from about 1 μm to about 3 μm. In another embodiment, the MMAD is from about 3 μm to about 5 μm.

In another embodiment of the invention, the particles have an envelope mass density, also referred to herein as "mass density" of less than about 0.4 g/cm$^3$. The envelope mass density of an isotropic particle is defined as the mass of the particle divided by the minimum sphere envelope volume within which it can be enclosed.

Tap density can be measured by using instruments known to those skilled in the art such as the Dual Platform Microprocessor Controlled Tap Density Tester (Vankel, N.C.) or a GeoPyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopia convention, Rockville, Md., 10$^{th}$ Supplement, 4950-4951, 1999. Features which can contribute to low tap density include irregular surface texture and porous structure.

The diameter of the particles, for example, their VMGD, can be measured using an electrical zone sensing instrument such as a Multisizer Ile, (Coulter Electronic, Luton, Beds, England), or a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition within targeted sites within the respiratory tract.

Particles that have a tap density less than about 0.4 g/cm$^3$, median diameters of at least about 5 μm, and an aerodynamic diameter of from about 1 μm to about 5 μm, or from about 1 μm to about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

In comparison to smaller particles, the larger aerodynamically light particles, preferably having a VMGD of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al, *Biomaterials* 7:61-66 (1986); Krenis, L. J. and Strauss, B., Proc. Soc. Exp. Med., 107:748-750 (1961); and Rudt, S. and Muller, R. H., *J Contr. Rel.*, 22:263-272 (1992). For particles of statistically isotropic shape, such as spheres with rough surfaces, the particle envelope volume is approximately equivalent to the volume of cytosolic space required within a macrophage for complete particle phagocytosis.

The particles can be prepared, for example, by spray drying. For example, a spray drying mixture, also referred to herein as "feed solution" or "feed mixture," which includes the therapeutic agents described herein, a pharmaceutically acceptable carrier, and optionally a multivalent metal cation component are fed to a spray dryer.

The total amount of solvent or solvents being employed in the mixture being spray dried generally is greater than 99 weight percent. The amount of solids (drug, charged lipid and other ingredients) present in the mixture being spray dried generally is less than about 1.0 weight percent. Preferably, the amount of solids in the mixture being spray dried ranges from about 0.05% to about 0.5% by weight.

Using a mixture which includes an organic and an aqueous solvent in the spray drying process allows for the combination of hydrophilic and hydrophobic components, while not requiring the formation of liposomes or other structures or complexes to facilitate solubilization of the combination of such components within the particles.

Suitable spray-drying techniques are described, for example, by K. Masters in "Spray Drying Handbook," John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. An example of a suitable spray dryer using rotary atomization includes the Mobile Minor spray dryer, manufactured by Niro, Inc., Denmark. The hot gas can be, for example, air, nitrogen or argon.

Preferably, the particles are obtained by spray drying using an inlet temperature from about 100 to about 400° C. and an outlet temperature from about 50 to about 130° C.

The spray dried particles can be fabricated with a rough surface texture to reduce particle agglomeration and improve flowability of the powder. The spray-dried particle can be fabricated with features which enhance aerosolization via dry powder inhaler devices, and lead to lower deposition in the mouth, throat and inhaler device.

Aerosol dosage, formulations and delivery systems also may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6:273-313, 1990; and in Moren, "Aerosol dosage forms and formulations," in: *Aerosols in Medicine. Principles, Diagnosis and Therapy*, Moren, et al., Eds, Esevier, Amsterdam, 1985.

The compounds in the formulation may be contained in any appropriate amount in any suitable carrier substance, and are generally present in an amount of 1-95% by weight of the total weight of the particles that are administered. The pharmaceutical compositions used to deliver the individual components (glutathione, ascorbic acid or salts thereof, and sodium bicarbonate) can be formulated to release the components at a predetermined time period by using biodegradable polymers, or other polymeric drug delivery systems.

When controlled release formulations are used, they are preferably a) formulations that after a predetermined lag time create a substantially constant concentration of the drug within the lungs over an extended period of time, or b) formulations that localize drug action by, e.g., spatial placement of a controlled release composition adjacent to or in the lungs, for example, using mucoadhesive polymers.

Examples of suitable polymeric materials include acrylic polymers, methacrylic acid copolymers with an acrylic or methacrylic ester (e.g., methacrylic acid ethylacrylate copolymer (1:1) and methacrylic acid methylmethacrylate copolymer (1:2), polyvinyl acetate phthalate, hydroxypropyl cellulose acetate phthalate and cellulose acetate phthalate), as well as cellulose acetate phthalate, hydroxypropyl methylcellulose phthalate, polyvinyl acetate phthalate. Commercially available products include, for example, KOLLIKOAT®, EDRAGIT® (e.g., EUDRAGIT 40), AQUATERIC®, AQOAT®. The enteric polymers used can also be modified by mixing with other coating products that are not pH sensitive. Examples of such coating products include, for example, the neutral methacrylic acid esters with a small portion of trimethylammonioethyl methacrylate chloride, sold currently under the trade names EUDRAGIT® and EUDRA GIT® RL; a neutral ester dispersion without any functional groups, sold under the trade names EUDRAGIT® NE30D and EUDRAGIT® NE30, EUDRAGIT® 40; polysaccharides, like amylose, chitosan, chondroitin sulfate, dextran, guar gum, inulin and pectin; and other pH independent coating products.

The polymer in various embodiments is from about 5% to about 75% of the weight of the microgranule. In other embodiments, the polymer is from about 10% to about 60%, from about 20% to about 55%, from about 30% to about 80%, or from about 25% to about 50% of the weight of the microgranule. The weight percent of the polymer to the weight of the microgranule can depend, in part, on the polymer used, and the temperature of the polymer.

The microgranules may further comprise one or more of diluents, plasticizers, anti-agglomeratives, anti-sticking, glidants, anti-foam surfactants, or coloring substances. These, along with other polymers and coatings (e.g., protective coatings, over-coatings, and films) are more fully described below.

In order to deliver to the deep lung, it can be important to minimize particle agglomerization, and for this reason, excipients with anti-agglomerative properties can also be used. Examples include talc; plasticizing materials, like acetylated glycerides, diethylphthalate, propylene glycol and polyethylene glycol; surfactants like polysorbate and polyoxyethylenate esthers, anti-foaming agents, as well as anti-sticking agents.

Suitable ingredients can be incorporated into the coating formula such as plasticizers, which include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxydized tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. Other various layers, as recognized by one of skill in the art are also envisioned. The amount of plasticizer used in the polymeric material typically ranges from about 10% to about 50%, for example, about 10, 20, 30, 40, or 50%, based on the weight of the dry polymer. Optional modifying components of a protective layer which can be used over the enteric or other coatings include a water penetration barrier layer (semi-permeable polymer) which can be successively coated after the enteric or other coating to reduce the water penetration rate through the enteric coating layer and thus increase the lag time of the drug release. Coatings commonly known to one skilled in the art can be used for this purpose by coating techniques such as fluid bed coating using solutions of polymers in water or suitable organic solvents or by using aqueous polymer dispersions. For example, useful materials include cellulose acetate, cellulose acetate butyrate, cellulose acetate propionate, ethyl cellulose, fatty acids and their esters, waxes, zein, and aqueous polymer dispersions such as EUDRAGIT® RS and RL 3OD, EUDRAGIT® NE 3OD, EUDRAGIT® 40, AQUACOAT®, SURELEASE®, cellulose acetate latex. Combinations of the polymers and hydrophilic polymers such as hydroxy ethyl cellulose, hydroxypropyl cellulose (KLUCEL®, Hercules Corp.), hydroxypropyl methylcellulose (METHOCEL®, Dow Chemical Corp.), polyvinylpyrrolidone may also be used.

The amount of polymer to be used in the formulations is typically adjusted to achieve the desired drug delivery properties, including the amount of drug to be delivered, the rate and location of drug delivery, the time delay of drug release, and the size of the multiparticulates in the formulation. The combination of all solid components of the polymeric material, including co-polymers, fillers, plasticizers, and optional excipients and processing aids, typically provides about 1% to about 50% weight of the core.

Colon Targeted Drug Delivery Systems

Local delivery to the colon allows topical treatment of colonic disorders such as ulcerative colitis, inflammatory bowel disease, Crohn's disease, amebiosis, colonic cancer, local treatment of colonic pathologies, and systemic delivery of protein and peptide drugs Crohn's disease, and the like. There are a number of approaches for CDDS (Colon Specific Drug Delivery), including pH and time dependent systems, microbially-triggered systems, and pressure-controlled colonic delivery capsules, CODES™, and osmotic controlled drug delivery.

The colon specific drug delivery system (CDDS) should prohibit significant drug release and absorption in the stomach and the small intestine, predominantly only release the therapeutic agents once the system reaches the colon. It is preferred to administer the drug delivery systems via the oral route. Rectal administration offers the shortest route for targeting therapeutic agents to the colon, but it is difficult to reach the proximal part of colon via rectal administration. Drug preparation for intrarectal administration is typically in the form of solutions, foam, and suppositories.

Chronic colitis, namely ulcerative colitis, and Crohn's disease are currently treated with glucocorticoids, such as dexamethasone and methyl prednisolone, and other anti-inflammatory agents. Glucocorticoids can cause systemic side effects, including adenosuppression, immunosuppression, cushinoid symptoms, and bone resorption, when given systemically. Selective delivery of these drugs to the colon, for example, using the compositions described herein, which establish and/or maintain homeostasis in the colonic mucosa, can both lower the required dose and also reduce systemic side effects.

With these formulations, the compositions used to restore homeostasis to the intestinal mucosa. Therapeutic agents can be added, including probiotics, 5-amino-salicylic acid and other anti-inflammatory agents, antibiotics, antivirals, and the like.

Several of the conventional approaches for site-specific drug delivery to the colon are discussed in detail below.

pH Sensitive Polymer-Coated Drug Delivery

In the stomach, the pH ranges from 1 and 2 during fasting, but increases after eating. The pH is about 6.5 in the proximal small intestine, and about 7.5 in the distal small intestine. From the ileum to the colon, pH declines significantly. It is about 6.4 in the cecum. However, pH values as low as 5.7 have been measured in the ascending colon in healthy volunteers. The pH in the transverse colon is 6.6 and 7.0 in the descending colon. Use of pH dependent polymers is based on these differences in pH levels. The polymers described as pH dependent in colon specific drug delivery are insoluble at low pH levels but become increasingly soluble as pH rises. pH-dependent polymers can protect a formulation in the stomach and proximal small intestine, but can start to dissolve in the lower small intestine, which can result in poor site-specificity.

Delayed (Time Controlled Release System) Release Drug Delivery

Time controlled release system (TCRS), such as sustained or delayed release dosage forms, can also be used.

Appropriate integration of pH sensitive and time release functions into a single dosage form can improve the site specificity of drug delivery to the colon.

In the stomach, drug release can be suppressed using a pH-sensing function (acid resistance) in the dosage form. Typical enteric coated time-release tablets include at least three components, a drug containing core tablet (rapid release function), a swellable hydrophobic polymer coating layer, such as a hydroxy propyl cellulose layer (HPC) layer, which provides a time-release function, and an enteric coating layer (which typically functions by being resistant to stomach acid. The tablet does not release the drug in the stomach, by virtue of the acid resistance of the outer enteric coating layer. After gastric emptying, the enteric coating layer rapidly dissolves and the intestinal fluid begins to slowly erode the press coated polymer (HPC) layer. After the tablet has eroded to the point where the core tablet is reached, rapid drug release typically occurs, unless the drug itself is mixed with a degradable polymer, which can provide sustained release dependent on the degradation properties of the polymer.

Microbially-Triggered Drug Delivery

The microflora of the colon include predominantly anaerobic bacteria, e.g. bacteroides, bifidobacteria, eubacteria, clostridia, enterococci, enterobacteria and ruminococcus. This microflora meets its energy needs by fermenting various types of undigested substrates, using enzymes like pectinase, glucoronidase, xylosidase, arabinosidase, galactosidase, nitroreductase, azareducatase, deaminase, and urea dehydroxylase. Because of the presence of the biodegradable enzymes only in the colon, the use of biodegradable polymers for colon-specific drug delivery seems to be a more site-specific approach as compared to other approaches. Drug delivery can therefore be achieved by using materials that degrade in the presence of these enzymes.

Polymers can be used as drug carriers for drug delivery to the colon, and both synthetic and naturally-occurring polymers have been used for this purpose. Various azo polymers have been used as coating materials over drug cores, and these are susceptible to cleavage by the azoreducatase in the large bowel. In one embodiment, the coating includes polymers cross-linked with azoaromatic groups, which protect the drug from digestion in the stomach and small intestine. In the colon, the azo bonds are reduced, and the drug is released.

Naturally-occurring polysaccharides can be used to target the colon, since polymers of such monosaccharides are found in abundance, have wide availability, are inexpensive, and are available in a variety of structures with varied properties. They can be easily modified chemically, biochemically, and are highly stable, safe, nontoxic, hydrophilic and gel forming and in addition, are biodegradable. These include naturally occurring polysaccharides obtained from plant (guar gum, inulin), animal (chitosan, chondroitin sulphate), algal (alginates) or microbial (dextran) origin. The polysaccharides can be broken down by the colonic microflora to simple saccharides.

Pressure Controlled Drug-Delivery Systems

As a result of peristalsis, higher pressures are encountered in the colon than in the small intestine. Takaya et al. developed pressure controlled colon-delivery capsules prepared using ethylcellulose, which is insoluble in water (Takaya et al., "Importance of dissolution process on systemic availability of drugs delivered by colon delivery system," *J. Control. Rel.*, 50:(1-3):111-122 (1998)). Drug release occurs pressure in the lumen of the colon causes the water-insoluble polymer capsule to disintegrate. In pressure controlled ethylcellulose single unit capsules, the components are delivered in solution rather than in solid form, as would be the case with tablets.

Colon Targeted Delivery System (CODES™)

CODES™ was designed to address limitations associated with pH or time-dependent systems (see, for example, U.S. Pat. No. 6,368,629 to Watanabe et al. and Takemura et al., *Pro. Int. Sym. Control Rel. Bioact. Mat,* 27 (2000)). CODES™ is a combined approach of pH-dependent and microbially-triggered CDDS, using lactulose as a trigger for site specific drug release in the colon. The system includes a traditional tablet core comprising lactulose, which is over coated with an acid soluble material, such as Eudragit E, and then subsequently overcoated with an enteric material, such as Eudragit L. The enteric coating protects the tablet while it is located in the stomach, but then dissolves quickly following gastric emptying. The acid soluble material coating then protects the preparation as it passes through the alkaline pH of the small intestine, and once the tablet arrives in the colon, bacteria enzymatically degrade the polysaccharide (lactulose) into organic acid. The thus-formed acid lowers the pH surrounding the system sufficient to dissolve the acid soluble coating and release the therapeutic agents.

Osmotic Controlled Drug Delivery (ORDS-CT)

The OROS-CT (Alza Corporation) can be used to target therapeutic agents to the colon. The OROS-CT system includes from 1 to 6 osmotic (push-pull) units, each 4 mm in diameter, encapsulated within a hard gelatin capsule. Each bilayer push-pull unit contains an osmotic push layer and a drug layer, both surrounded by a semi-permeable membrane. An orifice is drilled through the membrane next to the drug layer. Immediately after the OROS-CT is swallowed, the gelatin capsule containing the push-pull units dissolves. The drug-impermeable enteric coating prevents each push-pull unit from absorbing water in the acidic aqueous environment of the stomach, but as the unit enters the small intestine, the coating dissolves. Water then enters the unit, causing the osmotic push compartment to swell, and forming a flowable gel in the drug compartment. The swelling forces the gel out of the orifice at a precisely controlled rate through the semipermeable membrane. Drug release typically begins when the unit reaches the colon. OROS-CT units can be tailored to maintain a constant release rate, in the colon, for up to 24 hours, or over a period as short as four hours. Any of these formulations can be used to administer the therapeutic agents described herein to the colon.

Delivery to the Oral Mucosa

The formulations described herein can also be used to deliver the therapeutic agents to the oral mucosa. The formulations can be used to establish and maintain homeostasis in the oral mucosa, which can occur in patients with "dry mouth." Chronic dry mouth, or xerostomia, is a common problem that can affect about 25% of all adults. Dry mouth symptoms can be triggered by medications, diabetes, Sjögren's Syndrome, and a variety of other causes. Symptoms of dry mouth include bad breath, a sticky, dry or sore mouth, cracking at the corners of the mouth, a red and parched mouth, blisters and mouth ulcers, and waking up with a dry mouth at night.

The formulations, which include glutathione, ascorbic acid and/or its salts, and sodium bicarbonate, can alleviate dry mouth. Accordingly, they can be added to mouthwashes, toothpastes, gels, and the like, as well as buccal formulations, particularly when therapeutic agents are used.

One type of user that may benefit from the formulations described herein is a consumer of nicotine gums, such as Nicorette®. Nicotine gum can cause a sore throat in some users, can cause jaw pain and/or tooth disorders, and dry mouth occurs in approximately 6 percent of users of some nicotine-containing gums.

Where patients are suffering from bacterial disorders in the mouth, such as periodontal disease, the formulations can also include, or be co-administered with, appropriate antibiotics, such as doxycycline and chlorhexidine. When patients are suffering from viral disorders such as cold sores, shingles, aphthous ulcers, and the like, the compositions can also include, or be co-administered with, antiviral agents. Particularly when the patients suffer from pain in their mouth, whether from bacterial or viral causes, physical injuries, or oral surgery, including tonsillectomies, uvulaplasties, scaling and root planning, grafting, and the like, the formulations described herein can help maintain homeostasis in the oral mucosa, which can accelerate healing, and can include anesthetics such as lidocaine, marcaine, xylocaine, and the like, to help alleviate pain. Anti-inflammatory agents can also be present.

Drugs can also be administered using buccal drug delivery vehicles, whether to treat the above-listed indications, or to administer drugs systemically. In addition to the well-known dissolvable films, which can include the therapeutic agents described herein, buccal drug delivery forms can also be used. The presence of the active agents (glutathione, ascorbic acid and its salts, and sodium bicarbonate) can help minimize irritation to the mouth which might otherwise be caused by some drugs, and which might otherwise minimize the ability to administer such drugs via the buccal route.

One form of buccal drug delivery uses fast melt technology, and is characterized by rapid drug release. A known fast melt product is Zydis, which is formulated as a wafer having a very low density and minimal quantities of excipient. Thus, for example U.S. Pat. No. 5,939,091 describes a method of making fast melt tablets comprising Sorbitol Instant. Similarly, WO 02/085119 describes a dosage form for intra-oral delivery of nicotine comprising a hydroxypropylmethylcellulose film. This delivery system is characterized by rapid dissolution providing for almost instantaneous delivery of the nicotine.

In other forms, the structure of the tablet is modified so as to provide a desired delivery profile. For example, PCT WO 03/039518 describes an oral dosage formulation for delivery of nicotine comprising two layers, the first providing for buccal drug delivery and the second providing for delivery via the stomach or intestines. This formulation provides an initial rapid release of nicotine in the mouth followed by a slow sustained release of nicotine in the gut. PCT WO 01/37814 which describes bilayered buccal tablets comprising nicotine. These tablets provide a biphasic release of nicotine from a modified lactose and magnesium stearate containing tablet.

Other buccal formulations are in the form of a gum or lozenge. For example, PCT WO 02/076211 describes an oral dosage formulation comprising nicotine, including a hard lozenge having a matrix which is in a glassy, i.e. amorphous physical state. These lozenges comprise a sodium carbonate buffer. EP 0 500 658 describes a nicotine containing stimulant unit for buccal drug delivery, which can comprise a gum component, and U.S. Pat. No. 6,183,775 describes a controlled-release lozenge comprising soluble filler, an insoluble film-forming agent, and a swellable polymer. The lozenges are produced by compressing a dry granulate.

Other known dosage forms include troches. For example, U.S. Pat. No. 3,590,111 describes troches, formed by wet and dry granulation procedures, which include guar gum, disaccharides and hexahydric saturated aliphatic alcohols. U.S. Pat. No. 4,829,056 discloses a buccal tablet containing at least one monosaccharide or disaccharide and locust bean gum. U.S. Pat. No. 5,470,566 discloses a chewing gum comprising a gum base and a "taste enhancer," which can include a sugar or sugar alcohol. Additional sweetening agents can also be used.

Accordingly, oral and buccal formulations can be used to provide an initial burst release (i.e., when dissolvable films are used), or sustained release (i.e., when lozenges or other such forms are used). The release profile of the active agent or the dissolution profile of the lozenge is governed by the matrix composition and lozenge size, and can be varied according to the nature of the active agent and the desired effect. Thus, the dissolution profile can be altered, while retaining the same amount of the active agent, by varying the lozenge size and/or the proportion of gum in the lozenge. A smaller overall lozenge size will result in faster dissolution. Similarly, a reduced gum content will result in faster lozenge dissolution.

A suitable dissolution profile for lozenges of the invention is such that after 20 minutes approximately 35-65% of the lozenge has dissolved, after 40 minutes, approximately 60-90% of the lozenge has dissolved, and after 60 minutes more than 70% of the lozenge has dissolved. Typically lozenges are not smaller than 300-400 mg, and are not larger than approximately 1.5 g, approximately 1.75 g or approximately 2 g. In general, lozenge size (in terms of dimensions and shape) should be suitable for parking the lozenge in the buccal cavity.

Any suitable gum may be used to prepare lozenges. Suitable gums include gum acacia, gum arabic, carob gum, carrageenan, ghattii gum, guar gum, karaya gum, pectin, tragacanth gum, locust bean gum and xanthan gum. A preferred gum component is gum acacia, especially supplied in spray dried form for manufacture of lozenges.

In addition to the gum, lozenges also typically include one or more non-crystallizing sugars and/or one or more non-crystallizing sugar alcohols. Non-crystallizing forms of sugars or sugar alcohols are commercially available and may conveniently be used. Alternatively, sugars or sugar alcohols can be heat treated to provide non-crystallizing properties. Suitable sugars and sugar alcohols include non-crystallizing or treated forms of dextrose, maltose, sucrose, fructose, glucose syrup, invert sugar syrup, honey, laevulose, sorbitol, xylitol, maltitol, mannitol and isomalt. Preferred non-crystallizing sugars or non-crystallizing sugar alcohols include non-crystallizing forms (or mixtures) of sorbitol, xylitol, maltitol, mannitol, and isomalt.

Lozenges will normally contain water, for example, a water content of approximately 5-20% by weight, and can also include appropriate buffers to maintain a pH suitable for buccal absorption of the active agent. The buffer can vary according to the active agent, and generally varies so as to provide a pH at which the active agent is in an non-ionized form. For example, if nicotine is present, the pH is preferably in the range 7.5-9.0, more preferably 8.0-8.4. Control of the lozenge pH, and in particular the use of phosphate buffers, can also provide an improved taste or "mouth feel."

Lozenges and other oral or buccal formulations can optionally comprise flavorings, vitamins, anti-oxidants, anti-fungals, anti-bacterials, taste masking agents, colorings, excipients, stabilizers and sweeteners. Suitable components may be selected from those known in the art.

Drugs particularly suitable for delivery via the oral or buccal route include alkaloids, for example nicotine, alkaloidal drugs, anti-emetics (for example 5-HT antagonists), agents for migraine treatment (for example 5-HT agonists), analgesics (for example cannabis, .DELTA.9-THC and alkaloids), drugs that benefit from rapid uptake, drugs used in acute therapy, drugs that need to be or are preferentially taken lying down, drugs taken by patients who cannot or do not wish to swallow or drugs to be taken where it is undesirable to use a large amount of water. Drugs are preferably readily absorbable across the buccal mucosa. Drugs particularly suitable for delivery via lozenges of the invention are drugs for which the first pass effect is not beneficial, i.e. drugs of which the potency is reduced as a result of metabolism in the liver. Mucosal delivery is ideal for such drugs as they are directly absorbed into the bloodstream without first passing through the liver.

Particularly preferred drugs for delivery using lozenges of the invention include nicotine, the analgesic A9-THC, the anti-emetic ondansetron (a 5-HT3 antagonist), and the anti-migraine drug sumatriptan (a 5-HT1 agonist). Drugs for delivery using lozenges of the invention may optionally be in the form of a pharmaceutically acceptable salt.

The oral or buccal drug delivery systems can be used to administer any suitable dose of an active agent. Typical doses may be in the range 0.5-10 mg, but doses of approximately up to 200 mg can be delivered.

The use of lozenges is particularly suitable for active agents where it is desirable to limit patient exposure to the agent. The controlled release characteristics of the lozenges allow self-titration of the drug dosage by the patient. This is useful, for example, when the lozenges are used to deliver agents for migraine treatment or analgesics. Once sufficient active agent has been absorbed to overcome the symptoms for which the agent has been administered, the remainder of the lozenge can be removed from the patient's mouth.

Vaginal and Rectal Formulations

When used to treat or prevent disorders in the rectum or vagina, the formulations include the components described herein (i.e., glutathione or a salt, prodrug, or derivative thereof, an organic acid or a salt thereof, bicarbonate, and the like), as well as conventional lubricants used in such formulations.

Composition for rectal and/or vaginal administration can be formulated for topical administration, and in certain embodiments the composition is formulated as a gel, or formulated as a topical cream, ointment, lotion or foam formulation. The composition can further comprise a pharmaceutically acceptable excipient, a lubricant, an antifungal, antibacterial, or antiviral agent, an antipruritic agent, or an anesthetic, for example.

Other therapeutic agents used to treat disorders of the rectum and/or vagina can be added, as appropriate.

The formulations suitable for vaginal or rectal administration can be present as aqueous or oily suspensions, solutions or emulsions (liquid formulations) containing in addition to the active ingredients, such carriers as are known in the art to be appropriate. For "stand-alone" lubricants (i.e., lubricants that are not pre-packaged with condoms), gels and similar aqueous formulations are generally preferred, for various reasons known to those skilled in the art.

The topical formulations can be applied to the vagina and/or the anus. The composition administered to the anus is suitably a foam or gel, etc., such as those described above with regard to vaginal application. In the case of anal application, it may be preferred to use an applicator which distributes the composition substantially evenly throughout the anus. For example, a suitable applicator is a tube 2.5 to 25 cm, preferably 5 to 10 cm, in length having holes distributed regularly along its length.

When the composition is a water-soluble vaginal cream or gel, suitably 0.1 to 4 grams, preferably about 0.5 to 2 grams, are applied. When the composition is a vaginal spray-foam, suitably 0.1 to 2 grams, preferably about 0.5 to 1 grams, of the spray-foam are applied. When the composition is an anal cream or gel, suitably 0.1 to 4 grams, preferably about 0.5 to 2 grams of the cream or gel is applied. When the composition is an anal spray-foam, suitably 0.1 to 2 grams, preferably about 0.5 to 1 grams of the spray-foam are applied.

As a vaginal formulation, the active ingredients can be used in conjunction with a spermicide, and may be employed with a condom, diaphragm, sponge or other contraceptive device. Examples of suitable spermicides include nonylphenoxypolyoxyethylene glycol (nonoxynol 9), benzethonium chloride, and chlorindanol. Suitably, the pH of the composition is 4.5 to 8.5. Vaginal compositions preferably have a pH of 4.5 to 6, most preferably about 5.

Vaginal formulations also include suppositories (for example, gel-covered creams), tablets and films. The suppositories can be administered by insertion with an applicator using methods well known in the art.

The compositions can also be in the form of a time-release composition. In this embodiment, the composition is incorporated in a composition which will release the active compound at a rate which will result in the vaginal or anal concentration described above. Time-release compositions are disclosed in Controlled Release of Pesticides and Pharmaceuticals, D. H. Lew, Ed., Plenum Press, New York, 1981; and U.S. Pat. Nos. 5,185,155; 5,248,700; 4,011,312; 3,887,699; 5,143,731; 3,640,741; 4,895,724; 4,795,642; Bodmeier et al, *Journal of Pharmaceutical Sciences*, vol. 78 (1989); Amies, *Journal of Pathology and Bacteriology*, vol. 77 (1959); and Pfister et al, *Journal of Controlled Release*, vol. 3, pp. 229-233 (1986), all of which are incorporated herein by reference.

The compositions can also be in the form which releases the composition in response to some event such as vaginal or anal intercourse. For example, the composition may contain the vesicles or liposomes which are disrupted by the mechanical action of intercourse. Compositions comprising liposomes are described in U.S. Pat. No. 5,231,112 and Deamer and Uster, "Liposome Preparation: Methods and Mechanisms" in *Liposomes*, pp. 27-51 (1983); Sessa et al, *J. Biol. Chem.*, vol. 245, pp. 3295-3300 (1970); *Journal of Pharmaceutics and Pharmacology*, vol. 34, pp. 473-474 (1982); and *Topics in Pharmaceutical Sciences*, D. D. Breimer and P. Speiser, Eds., Elsevier, New York, pp. 345-358 (1985), which are incorporated herein by reference.

The compositions can be associated with a contraceptive device or article, such as a vaginal ring device, an intrauterine device (IUD), vaginal diaphragm, vaginal sponge, pessary, condom, etc. In the case of an IUD or diaphragm, time-release and/or mechanical-release compositions may be preferred, while in the case of condoms, mechanical-release compositions are preferred.

Rings and intravaginal sponges which release the therapeutic agents in a time-controlled fashion can be used. Suitable intravaginal sponges are disclosed in U.S. Pat. Nos. 3,916,898 and 4,360,013, which are incorporated herein by reference. The present article may also be a vaginal dispenser, such as those disclosed in U.S. Pat. No. 4,961,931, which is incorporated herein by reference.

The compositions can also be in the form of an intravaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of the therapeutic agents.

In one particular embodiment, the composition contains nonoxynol, a widely-used spermicidal surfactant.

The compositions can also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

Non-limiting examples of useful lubricants include cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate, white wax, or mixtures of two or more of the above. The amount of lubricant in the topical formulation can range from about 0 to about 95 weight percent. Typical cream and ointment formulations comprise 0.1 to 95 weight percent of lubricant. The topical formulations can comprise one or more adjuvants, wherein the adjuvant is an antimicrobial agent, antioxidant, humectant or emulsifier, or mixture of two or more thereof. The gels and foams of the present invention can include one or more antimicrobial agents and optionally can include one or more of antioxidants, humectants and emulsifiers.

Non-limiting examples of useful antimicrobial agents are benzyl alcohol, propylene glycol, propyl paraben, methyl paraben, or mixtures of two or more thereof. The amount of antimicrobial agents in the topical formulation can range from about 0.01 to about 10 weight percent, and in some embodiments from about 0.2 to about 10 weight percent, on a basis of total weight of the topical formulation.

Non-limiting examples of useful antioxidants include butylated hydroxyanisole, butylated hydroxytoluene, edetate disodium or mixtures of two or more thereof. The amount of antioxidant in the topical formulation can range from about 0.01 to about 1 weight percent, and in some embodiments from about 0.01 to about 0.1 weight percent, on a basis of total weight of the topical formulation.

Non-limiting examples of useful humectants include ethylene glycol, glycerin, sorbitol or mixtures of two or more thereof. The amount of humectant in the topical formulation can range from about 1 to about 30 weight percent, and in some embodiments from about 2 to about 20 weight percent, on a basis of total weight of the topical formulation.

Non-limiting examples of useful emulsifiers include acrylic acid polymers (such as carbomer brand thickeners e.g. Carbomer 934P, manufactured by Voveon, Inc.), polyoxyethylene-10-stearyl ether, polyoxyethylene-20-stearyl ether, cetostearyl alcohol, cetyl alcohol, cholesterol, diglycol stearate, glyceryl monostearate, glyceryl stearate, polygeyceryl-3-oleate, hydroxypropyl cellulose, hydroxypropylmethyl cellulose, lanolin, polyoxyethylene lauryl ether, methyl cellulose, polyoxyethylene stearate, polysorbate, propylene glycol monostearate, sorbitan esters, stearic acid or mixtures of two or more thereof.

The amount of emulsifier in the topical formulation can range from about 1 to about 40 weight percent, and in some embodiments from about 5 to about 30 weight percent, on a basis of total weight of the topical formulation.

The gel formulations of the present invention comprise one or more gelling agents. Non-limiting examples of useful gelling agents include carboxylic acid polymers including acrylic acid polymers crosslinked with cross links such as allyl ethers of sucrose (e.g. carbomer brand thickeners), cetostearyl alcohol, hydroxymethyl cellulose, polyoxyethylene-polyoxypropylene copolymer, sodium carboxymethylcellulose, polyvinyl pyrrolidone, or mixtures of two or more thereof. The amount of gelling agent in the topical gel formulation can range from about 0.1 to about 10 weight percent, and in some embodiments from about 0.1 to about 1 weight percent, on a basis of total weight of the topical formulation.

The formulations can contain one or more additional excipients well known in the art, for example water and a thickening agent such as colloidal silicon dioxide.

Ocular Formulations

Ocular formulations are typically in the form of eye drops, which may include lubricants and thickeners, as well as pH buffered solutions. When used to treat eye disorders, the formulations can include, in addition to the glutathione, organic acid and pharmaceutically acceptable salts, prodrugs and derivatives thereof, and sodium bicarbonate, agents useful for treating ocular disorders.

For example, in treating ocular infections, such as trachoma, antimicrobials can be used. The antimicrobials can be antibacterials, antivirals, or antifungals, depending on the nature of the infection. The antimicrobials can treat the underlying disorder, and the other components can restore and maintain homeostasis in the eye as it is healing. Suitable antimicrobials are well known to those of skill in the art.

Eye infections and injuries are often associated with inflammation, so an anti-inflammatory, such as a steroid, for example, a corticosteroid, can also be used. By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory ocular diseases include trachoma, wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye.

In some embodiments of this invention, wherein the composition is intended for topical administration to ocular or periocular tissues, the composition may be formulated for application as a liquid drop, ointment, a viscous solution or gel, a ribbon, or a solid. The composition can be topically applied, for example, without limitation, to the front of the eye, under the upper eyelid, on the lower eyelid and in the cul-de-sac.

An exemplary composition for administration to the ocular and periocular tissues is an aqueous polymeric suspension. The polymeric suspending agent is suspended in an aqueous medium. The polymeric suspending agent is preferably in suspension (i.e. water insoluble and/or water swellable), although water soluble suspending agents are also suitable for use with a suspension of the active agents. The suspending agent serves to provide stability to the suspension and to increase the residence time of the dosage form on the eye. It can also enhance the sustained release of the drug in terms of both longer release times and a more uniform release curve.

Examples of polymeric suspending agents include dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. A preferred polymeric suspending agent is a water swellable, water insoluble polymer, especially a crosslinked carboxy-containing polymer.

Such polymers may be crosslinked by a polyfunctional crosslinking agent, preferably a difunctional crosslinking agent. The amount of crosslinking should be sufficient to form insoluble polymer particles, but not so great as to unduly interfere with sustained release of the active agents. Typically the polymers are only lightly crosslinked. Preferably the crosslinking agent is contained in an amount of from about 0.01% to about 5%, preferably from about 0.1% to about 5.0%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250, the entire contents of each patent being incorporated herein by reference.

The crosslinked carboxy-vinyl polymers may be made from a carboxy-vinyl monomer or monomers as the sole monoethylenically unsaturated monomer present, together with a crosslinking agent or agents. Preferably the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers.

Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol®. Most preferably, a carboxy-containing polymer system known by the tradename DuraSite®, containing polycarbophil, which is a sustained release topical ophthalmic delivery system that releases the drug at a controlled rate, is used in the aqueous polymeric suspension composition of the present invention.

The crosslinked carboxy-vinyl polymers used in practicing this invention are preferably prepared by suspension or emulsion polymerizing the monomers, using conventional free radical polymerization catalysts, to a dry particle size of not more than about 50 m in equivalent spherical diameter; e.g., to provide dry polymer particles ranging in size from about 1 to about 30 m, and preferably from about 3 to about 20 m, in equivalent spherical diameter. Using polymer particles that were obtained by mechanically milling larger polymer particles to this size is preferably avoided. In general, such polymers will have a molecular weight which has been variously reported as being from about 250,000 to about 4,000,000, and from 3,000,000,000 to 4,000,000,000.

In a more preferred embodiment of the invention for topical ophthalmic administration, the particles of crosslinked carboxy-vinyl polymer are monodisperse, meaning that they have a particle size distribution such that at least 80% of the particles fall within a 10 µm band of major particle size distribution. More preferably, at least 90% and most preferably at least 95%, of the particles fall within a 10 µm band of major particle size distribution. Also, a monodisperse particle size means that there is no more than 20%, preferably no more than 10%, and most preferably no more than 5% particles of a size below 1 µm. The use of a monodispersion of particles will give maximum viscosity and an increased eye residence time of the ophthalmic medicament delivery system for a given particle size. Monodisperse particles having a particle size of 30 µm and below are most preferred. Good particle packing is aided by a narrow particle size distribution.

The aqueous polymeric suspension normally contains the active agents in an amount from about 0.05% to about 25%, preferably about 0.10% to about 20%, more preferably about 0.5% to about 15%, more preferably about 1% to about 12%, more preferably about 2% to about 10.0%, and polymeric suspending agent in an amount from about 0.05% to about 10%, preferably about 0.1% to about 5% and more preferably from about 0.2% to about 1.0% polymeric suspending agent. In the case of the above described water insoluble, water-swellable crosslinked carboxy-vinyl polymer, another preferred amount of the polymeric suspending agent is an amount from about 0.5% to about 2.0%, preferably from about 0.5% to about 1.2%, and in certain embodiments from about 0.6% to about 0.9%, based on the weight of the composition. Although referred to in the singular, it should be understood that one or 25 more species of polymeric suspending agent, such as the crosslinked carboxy-containing polymer, can be used with the total amount falling within the stated ranges. In one preferred embodiment, the composition contains about 0.6% to about 0.8% of a polycarbophil such as NOVEON AA-1.

When water soluble polymers are used as the suspending agent, such as hydroxypropyl methylcellulose, the viscosity will typically be about 10 to about 400 centipoise, more typically about 10 to about 200 centipoises or about 10 to about 25 centipoise.

Steroids are one of the most commonly used medications for decreasing ocular inflammation. By inhibiting the breakdown of phospholipids into arachidonic acid, these agents act early on the inflammatory pathway. The most common side effects of this class of medications are cataract formation and glaucoma. Drugs such as loteprednol etabonate (Lotemax; Bausch+Lomb, Rochester, NY) carry a lower risk of increased IOP.1 Another new agent is difluprednate (Durezol; Sirion Therapeutics, Tampa, FL), which possesses even greater potency than the other available corticosteroids.

Although nonsteroidal anti-inflammatory drugs have been used to treat inflammatory conditions, physicians should exercise caution when prescribing this class of medications. In patients with severe inflammation combined with dry eye disease, treatment with non-steroidal anti-inflammatory drugs has caused corneal melting (Isawi and Dhaliwal, "Corneal melting and perforation in Stevens Johnson syndrome following topical bromfenac use," J Cataract Refract Surg. 2007; 33(9):1644-1646). In contrast, cyclosporine 0.05% (Restasis; Allergan, Inc., Irvine, CA) has been shown to effectively control many causes of ocular surface inflammation, and this ophthalmic emulsion has an excellent safety profile. Accordingly, combinations of the active agents described herein and cyclosporine, particularly in the form of ocular formulations such as eye drops, are also within the scope of the invention.

If additional therapy is required, autologous serum tears can be very effective. Because they contain several important components of natural tears such as epidermal growth factor, fibronectin, and vitamin A, autologous serum tears increase the health of the ocular surface (Kojima, et al., "Autologous serum eye drops for the treatment of dry eye diseases" Cornea, 27(suppl 1):S25-30 (2008)).

Another alternative is to use agents such as tacrolimus, Sirolimus, and the like, for example, in the form of a dermatologic ointment (Protopic; Astellas Pharma US, Inc., Deerfield, IL) (Wyrsch et al., "Safety of treatment with tacrolimus ointment for anterior segment inflammatory diseases," Klin Monatsbl Augenheilkd, 226(4):234-236 (2009)). Thus, combinations of these agents and the glutathione, organic acid or salts thereof, and sodium bicarbonate, are also within the scope of the invention.

Methods of Treatment

The compositions described herein can be used to treat disorders associated with mucosal membranes, by delivering the compositions to the appropriate mucosal membranes. In some embodiments, the mucosal membranes are the lungs, such as the deep lung (alveolar region), and in other embodiments, the mucosal membranes are one or more of the eyes, mouth, nose, rectum, and vagina.

In still further embodiments, the composition further comprises, or the composition is administered in combination or in alternation with, one or more additional therapeutic agents. That is, in some embodiments, the composition and further therapeutic agents are directed to the same locus in the same formulation, and in other embodiments, the composition can be administered via one pathway, and the further therapeutic agents can be administered via a different pathway.

In some embodiments, the further therapeutic agents treat the desired disorder for which they are administered, but cause certain side effects, such as a drying of the mucosal membranes that results in discomfort and/or injury, that can be addressed by administering the compositions described herein.

In other embodiments, the further therapeutic agents and the compositions described herein both treat the underlying disorder, though via different means, such that an additive or synergistic effect can be achieved. As a result, in some aspects of this embodiment, lower doses of the additional therapeutic agent can be effective, which lower doses can result in fewer side effects, or provide other benefits to the patient.

Representative further therapeutic agents include an antibiotic, an antifungal, a beta antagonist an immunosuppressant, an immunomodulator and/or a steroid, in any combination.

Where the additional therapeutic agent is present, the resulting new formulations can provide new applications for the therapeutic agent, enhance the efficacy of the therapeutic agent, reduce unwanted side effects associated with the therapeutic agent, and/or reduce the dose of the therapeutic agent.

Particularly where the compositions include these therapeutic agents, the compositions can be used to treat mucosal diseases, pulmonary diseases, autoimmune diseases (including multiple sclerosis, Crohn's disease, ulcerative colitis, lupus, inflammatory bowel syndrome, irritable bowel syndrome, etc.), infectious diseases (e.g., HIV), Alzheimer's disease, and the like.

In some aspects of these embodiments, a single formulation includes the therapeutic agents and the glutathione, organic acid and bicarbonate, and in other aspects of these embodiments, the therapeutic agents are present in a first formulation and the glutathione, organic acid and bicarbonate are present in a second formulation. As such, the compositions can be used in combination or 'kit' therapies. The formulation with the therapeutic agent can be present in oral, injectable, or inhaled forms, and the glutathione, organic acid and bicarbonate present in an inhaled (e.g., pulmonary or intranasal) formulation.

The present invention finds use in both veterinary and medical applications. Suitable subjects of the present invention include, but are not limited to mammals. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments of the present invention, the subject is a human. Human subjects include both males and females and subjects of all ages including neonatal, infant, juvenile, adolescent, adult, and geriatric subjects. In further embodiments of this invention, a subject can be a plant.

Yet further embodiments of this invention include the use of a pharmaceutical composition of this invention in the manufacture of a medicament for treating a mucosal tissue disorder, treating an infection in mucosal tissue and/or treating inflammation in mucosal tissue in a subject.

In particular embodiments, the pharmaceutical composition of this invention is administered one or more times daily. (e.g., 1, 2, 3, 4, 5, 6, 7, 8, 9, 10 or more times a day) In particular embodiments, the subject is a human.

In various embodiments of the methods of this invention, the pharmaceutical composition can be administered via inhalation, intranasally, via the eye, via the ear, via sinus irrigation, via bronchoscope or any combination thereof.

Treatment of Pulmonary Disorders

Thus, in one embodiment, the present invention provides a method of treating an airway disorder or disease in a subject in need thereof, comprising delivering to the subject an effective amount of the pharmaceutical composition of this invention.

In the method described above, the airway disorder or disease can be, but is not limited to, chronic inflammatory lung disease, pulmonary fibrosis, pulmonary vasculitis, pulmonary sarcoidosis, inflammation and/or infection associated with lung transplantation, acute lung rejection, pulmonary artery hypertension, bronchitis, sinusitis, asthma, cystic fibrosis, bacterial infection (e.g., by *Pseudomonas aeruginosa*, anthrax, *Mycobacterium*) fungal infection (e.g., by *Aspergillus, Pneumocystis carnii*), parasite infection, viral infection, chronic obstructive pulmonary disease (COPD), bronchiolitis obliterans syndrome (BOS), primary ciliary dyskinesia (PCD), idiopathic pulmonary fibrosis (IPF), alveolar protienosis, eosinophilic pneumonia, eosinophilic bronchitis, acute respiratory distress syndrome (ARDS), inflammation and/or infection associated with mechanical ventilation, ventilator-associated pneumonia, asbestos-related airway disorder or disease, dust-related airway disorder or disease, silicosis, chemical agent-related airway disease or disorder and any combination thereof.

As one nonlimiting example, the compositions and formulations of this invention can be administered to a subject in combination with a phosphodiesterase 3 (PDE3) inhibitor and/or a phosphodiesterase 4 (PDE4 inhibitor. It is contemplated that the combination will allow for the PED3 and/or PED4 inhibitor to have a therapeutic effect in the presence of the composition or formulation of this invention at a dose that is lower than a dose that would have a similar therapeutic effect in the absence of the composition or formulation of this invention.

Further embodiments of this invention include a method of treating an infection in the airway of a subject (e.g., a subject in need thereof), comprising delivering to the subject an effective amount of the pharmaceutical composition of this invention.

The present invention also provides a method of treating inflammation in the airway of a subject (e.g., a subject in need thereof), comprising delivering to the subject an effective amount of the pharmaceutical composition of this invention.

While not wishing to be bound by a particular theory, it is believed that the formulations disclosed herein are effective in achieving and maintaining either a normal lung mucosa, or at least a more normal lung mucosa, which is an important factor in maintaining lung health. Drugs administered to the lungs are often associated with certain side effects, in some cases because of dosage, and in other cases because they damage the lung tissue. In some embodiments, therapeutic agents combined with the formulations disclosed herein are effective at lower doses, and at such lower doses, the incidence of side effects can be reduced. For example, one can decrease inhaled corticosteroid (ICS) dosing and, accordingly, reduce the risk of pneumonia in chronic obstructive pulmonary disease (COPD) patients, and reduce the dose of β-agonists and other bronchodilators to reduce the risk of death in asthma patients.

In other embodiments, where the therapeutic agent interacts unfavorably with lung tissue, the formulations described herein can help to restore homeostasis to the lung tissue, and thus help minimize or eliminate damage caused by the therapeutic agents.

The present invention also provides a method of treating an airway disorder or disease in a subject in need thereof, comprising delivering to the subject an effective amount of the pharmaceutical compositions described herein, optionally in combination with a steroid and/or bronchodilator, such as a beta$_2$-agonist.

Furthermore, the present invention provides a method of treating an infection in the airway of a subject in need thereof, comprising delivering to the subject an effective amount of the pharmaceutical composition described herein, optionally in combination with one or more antibiotics. The antibiotics can be administered locally to the lungs and/or systemically Inflammation in the airway of a subject in need thereof can be treated by delivering to the subject an effective amount of the pharmaceutical compositions described herein.

In particular embodiments of the methods of this invention, upon administration of the pharmaceutical composition to a human subject, the concentration of thiocyanate in the airway surface liquid of the subject is from about 0.5 mM to about 3.0 mM. The concentration of thiocyanate in the saliva of a normally healthy subject is from about 0.5 mM to about 3.0 mM (Schultz et al, 1996); whereas, airway secretions of normally healthy individuals have been determined to contain 0.3 to 0.65 mM SCN– (Wijkstrom-Frei et al., 2003). The nasal airway fluid concentrations range from 0.1 to 1.2 mM. These values are more than tenfold greater than serum values (0.05 mM, Lundquist et al. 1995). The amount to be delivered to the selected mucosal surface will be designed to result in concentrations up to 3.0 mM.

In particular embodiments of the methods of this invention, upon administration of the pharmaceutical composition to a human subject, the concentration of glutathione in the airway surface liquid of the subject is from about 0.1 mM to about 1.0 mM. This is approximately 140 fold higher than found in plasma in the same individual. The concentrations delivered are designed to raise the levels to 1.0 mM.

In some embodiments of the methods of this invention, the glutathione, pharmaceutically acceptable salt thereof, derivative thereof, analogue thereof and/or prodrug thereof, the organic acid, pharmaceutically acceptable salt thereof, derivative thereof, analogue thereof and/or prodrug thereof, the buffer and/or the thiocyanate of the pharmaceutical composition can be administered or delivered as separate components but in a sequential and/or temporal manner that allows the components to work together to achieve the desired therapeutic effect. In a further embodiment the components can be delivered simultaneously from separate containers that feed into a common conduit that then delivers the components to the subject.

In some embodiments, the pharmaceutical composition is delivered to the upper third of the nasal cavity, to the superior meatus, the olfactory region and/or the sinus region of the nose. The olfactory region is a small area that is typically about 2-10 $cm^2$ in man (25 $cm^2$ in the cat) located in the upper third of the nasal cavity for deposition and absorption by the olfactory epithelium and subsequent transport by olfactory receptor neurons. Located on the roof of the nasal cavity, in the superior meatus, the olfactory region is useful for delivery in some embodiments, because it is the only known part of the body in which an extension of the CNS comes into contact with the environment (Bois et al. *Fundamentals of Otolaryngology*, p. 184, W.B. Saunders Co., Philadelphia, 1989).

The compositions of the present invention are administered in a manner compatible with the dosage formulation in such an amount as will be effective for the desired result. In particular embodiments, the pharmaceutical composition is administered to the subject in a therapeutically effective amount (as described hereinabove). The quantity to be administered depends on a number of factors, such as, e.g., the subject to be treated and the severity of the condition. Precise amounts of active ingredient required to be administered may depend on the judgment of the practitioner. In general, the dose per subject may be 5 µg, 50 µg, or 250 µg, up to 5 mg, 10 mg, 20 mg, or 100 mg, per dose.

Exemplary dosages include from about 0.001, 0.01 or 0.1 to about 1, 5, 10 or 20 mg/dose, e.g., 1, 2, 3, 4, 5, 6, 7, 8, 9, 10 or more times daily, two to four times weekly, weekly, two to three times monthly or monthly, or as needed by the subject.

The composition of this invention can be administered for a sustained period, such as for at least about one month, at least about 2 months, at least about 3 months, at least about 6 months, or at least about 12 months or longer (e.g., as a chronic life-long treatment).

Any suitable dosing schedule can be followed. For example, the dosing frequency can be a once weekly dosing. The dosing frequency can be a once daily or multiple times daily dosing. The dosing frequency can be more than once weekly dosing. The dosing frequency can be more than once daily dosing, such as any one of 2, 3, 4, 5, 6, 7, 8, 9, 10 or more than 10 daily doses. The dosing frequency can be intermittent (e.g., multiple daily dosing for 7 days followed by no doses for 7 days, repeated for any 14 day time period, such as 2 months, 4 months, 6 months or more). The dosing frequency can be continuous (e.g., one weekly dosing for continuous weeks).

In some embodiments, the pharmaceutical composition of this invention can be administered in a single "shock" dose, for example, during a bronchoscopy.

In other embodiments, the methods of the invention can be carried out on an as-needed basis by self-medication.

Any of the dosing frequencies can be used with any dosage amount. Further, any of the dosing frequencies and/or dosage amounts can be used with any of the pharmaceutical compositions described herein.

The pharmaceutical composition can be delivered in any suitable volume of administration. In representative embodiments of the invention, the administration volume for intranasal delivery ranges from about 25 microliters to 200 microliters or from about 50 to 150 microliters or from about 50, 100, 250 or 500 microliters to about 1, 2, 3, 3.5 or 4 milliliters in a human. Typically, the administration volume is selected to be large enough to allow for delivery of therapeutic quantities while accounting for dilution in ASL in maintenance conditions in relatively "normal" airways (10-30 ml ASL) and in cystic fibrosis (CF) airways (40-50 ml ASL or more plus thick, tenacious, and heavily infected mucus secretions).

"Administration by inhalation" or "delivery by inhalation" means administration to or delivery to the subject through the mouth and/or nose.

The term "intranasal administration" as used herein, refers to a systemic form of administration of a pharmaceutical composition of this invention, whereby the composition is introduced into one or both of the nasal passages of a subject such that the composition contacts the nasal mucosa and in some embodiments, is absorbed into the systemic circulation. In certain embodiments, a therapeutically effective amount is administered. Intranasal administration of the pharmaceutical compositions of the present invention can comprise a single administration or multiple administrations of the compositions.

Intranasal administration of the pharmaceutical compositions of the present invention can be achieved by any known method. In particular embodiments, intranasal administration is by inhalation (e.g., using an inhaler, atomizer or nebulizer device), alternatively, by spray, tube, catheter, syringe, dropper, packtail, pipette, pledget, and the like. As a further illustration, the pharmaceutical composition can be administered intranasally as (1) nose drops, (2) powder or liquid sprays or aerosols, (3) liquids or semisolids by syringe, (4) liquids or semisolids by swab, pledget or other similar means of application, (5) a gel, cream or ointment, (6) an infusion, or (7) by injection, or by any means now known or later developed in the art. In particular embodiments, the method of delivery is by nasal drops, spray or aerosol. As used herein, aerosols can be used to deliver powders, liquids or dispersions (solids in liquid).

In representative embodiments, the pharmaceutical formulation is directed upward during administration, so as to enhance delivery to the upper third (e.g., the olfactory epithelium in the olfactory region) and the side walls (e.g., nasal epithelium) of the nasal cavity. Further, orienting the subject's head in a tipped-back position or orienting the subject's body in Mygind's position or the praying-to-Mecca position can be used to facilitate delivery to the olfactory region.

The formulations can be provided in single or multidose form. In the latter case a means of dose metering can be provided. In the case of a dropper or pipette this may be achieved by the patient or caregiver administering an appropriate, predetermined volume of the composition. In the case of a spray this may be achieved, for example, by means of a metering atomizing spray pump.

A further aspect of the present invention is an intranasal spray device comprising a pharmaceutical composition of the present invention.

Many devices are known in the art for nasal delivery. Exemplary devices include particle dispersion devices, bidirectional devices, and devices that use chip-based ink-jet technologies. ViaNase (Kurve Technolgies, Inc., USA) uses controlled particle dispersion technology (e.g., an integrated nebulizer and particle dispersion chamber apparatus, for example, as described in International patent publication WO 2005/023335). Optinose and Optimist (OptiNose, AS, Norway) and DirectHaler (Direct-Haler A/S, Denmark) are examples of bidirectional nasal delivery devices. Ink-jet dispensers are described in U.S. Pat. No. 6,325,475 (Micro-Fab Technologies, Inc., USA) and use microdrops of drugs on a millimeter sized chip. Devices that rely on iontophoresis/phonophoresis/electrotransport are also known, as described in U.S. Pat. No. 6,410,046 (Intrabrain International NV, Curacao, AN). These devices comprise an electrode with an attached drug reservoir that is inserted into the nose. Iontophoresis, electrotransport or phonophoresis with or without chemical permeation enhancers can be used to deliver the drug to the target region (e.g., olfactory). Other commercially available nasal applicators are, for example, the Pfeiffer unit dose and bidose system, the Valois monospray, bidose and monopowder system or the Becton-Dickinson Accuspray™ system. Also suitable are glass or plastic bottles with commercially available metering pump spray heads.

Nasal delivery devices are also described in U.S. Pat. No. 6,715,485 (OptiNose AS); U.S. Pat. No. 6,325,475 (Microfab Technologies, Inc.); U.S. Pat. No. 6,948,492 (University of Kentucky Research Foundation); U.S. Pat. No. 6,244,573 (LyteSyde, LLC); U.S. Pat. No. 6,234,459 (LyteSyde, LLC); U.S. Pat. No. 6,244,573 (LyteSyde, LLC); U.S. Pat. No. 6,113,078 (LyteSyde, LLC); U.S. Pat. No. 6,669,176 (LyteSyde, LLC); U.S. Pat. No. 5,724,965 (Respironics Inc.); and U.S. Patent Publications US2004/0112378 A1; US 2004/0112379 A1; US 2004/0149289 A1; US 2004/0112380 A1; US 2004; 0182388 A1; US 2005/0028812 A1; US 2005/0235992 A1; US 2005/0072430 A1 and US 2005/0061324 A1.

Further, the pharmaceutical compositions of the present invention can optionally be administered in combination with one or more other therapeutic agents, for example, other therapeutic agents useful in the treatment and/or prevention of and/or any other treatment that may be beneficial to the subject.

As used herein, the administration of two or more compounds "in combination" means that the two compounds are administered closely enough in time that the presence of one alters the biological effects of the other. The two compounds may be administered concurrently, in the same or different formulations, or sequentially. Concurrent administration can be carried out by mixing the compounds prior to administration, or by administering the compounds in two different formulations, for example, at the same point in time but at different anatomic sites or using different routes of administration. As used herein, "concurrent" or "concurrently" means sufficiently close in time to produce a combined effect (that is, concurrently can be simultaneously, or it can be two or more events occurring within a short time period before or after each other).

The present invention also provides a method of treating a disease or disorder in mucosal tissue in a subject. Nonlimiting examples of mucosal tissue of this invention include the mouth, nose, eye, ear, upper respiratory tract, lower respiratory tract, gastrointestinal tract, vagina, rectum and urethra. Nonlimiting examples of diseases and/or disorders that can be treated according to the methods of this invention include oral apthae, Behcet's Disease, mucosal discoid lupus (e.g., Erythematosus), Bullous Diseases in mucosa (e.g., drug eruptions; Stevens-Johnsons Syndrome, Bullous lupus), herpes simplex and other viral infections, thrush and other fungal infections, lichenoid mucositis (e.g., lichen planus), inflammatory bowel disorder, and cancer.

Treatment of Ocular Disorders

Oxidative damage, UV damage, dystrophies and degenerations (e.g., macular degeneration) have been associated with decreased glutathione and ascorbate. Accordingly, the compositions described herein can provide lens, retina and corneal protection, repair and reduced inflammation, which can reduce the severity or incidence of diseases such as cataracts, dry eye and other retinopathies and ocular disorders that are either primary or secondary to other disorders or drug reactions.

Some of these disorders have an inflammatory component, such as trachoma, wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye. When treating these disorders, the compositions can optionally be administered with an anti-inflammatory agent.

The compositions described herein can be used, optionally but preferably in combination with antimicrobial therapy, to treat or prevent a variety of conditions associated with ocular infection. For example, conditions of the eyelids, including blepharitis, blepharconjunctivies, meibomianitis, acute or chronic hordeolum, chalazion, dacryocystitis, dacryoadenities; conditions of the conjunctiva, including conjunctivitis, ophthalmia neonatorum, and trachoma; conditions of the cornea, including corneal ulcers, superficial and interstitial keratitis, keratoconjunctivitis, foreign bodies, and post operative infections; and conditions of the anterior chamber and uvea, including endophthalmitis, infectious uveitis, and post operative infections, are a few of the tissues and conditions that can be treated by topical application of the therapeutic agents.

The prevention of infection includes pre-operative treatment prior to surgery as well as other suspected infectious conditions or contact. Examples of prophylaxis situations include treatment prior to surgical procedures such as blepharoplasty, removal of chalazia, tarsorrhapy, procedures for the canualiculi and lacrimal drainage system and other operative procedures involving the lids and lacrimal apparatus; conjunctival surgery including removal of ptyregia, pinqueculae and tumors, conjunctival transplantation, traumatic lesions such as cuts, burns and abrasions, and conjunctival flaps; corneal surgery including removal of foreign bodies, keratotomy, and corneal transplants; refractive surgery including photorefractive procedures; glaucoma surgery including filtering blebs; paracentesis of the anterior chamber; iridectomy; cataract surgery; retinal surgery; and procedures involving the extra-ocular muscles. The prevention of ophthalmia neonatorum is also included.

Brain

Studies have indicated oxidative stress in the central nervous system (CNS) and brain contribute to diseases such as Alzheimer's, Parkinson's, ischemia and traumatic injuries, etc., to the brain and CNS. As such, this therapy could offer neuronal, glial and astrocyte protection, repair and reduced inflammation, which could reduce the severity or incidence of these diseases. In these embodiments, other therapeutic agents useful for treating these disorders, including dopamine agonists and partial agonists, selective serotonin reuptake inhibitors (SSRI) can also be used. In some aspects of these embodiments, the compositions are administered intrathecally, and in other aspects, the compositions are administered in another manner and cross the blood-brain barrier.

Nose

As an extension of the pulmonary and oral systems, application to the nasal passages can reduce nasal inflammation and infection, sinus inflammation and infection and other disorders primary or secondary to other disorders or drug reactions. Nasal and sinus administration of this therapy can lead to decreased pulmonary disease, as inflammation in the sinuses (e.g., asthma and cystic fibrosis) is often linked to inflammation and infection in the lower airways.

Mouth

Glutathione and ascorbate play a critical role in innate immune factors in the oral mucosa. This therapy can therefore offer oral, periodontal and dental protection, repair and reduced inflammation, which could reduce the severity or incidence of oral diseases that are primary disorders or secondary to other disorders or drug reactions.

In some embodiments, periodontal diseases can be treated with antibiotics, such as doxycycline and oral rinses such as chlorhexidine, which can be combined with the compositions described herein. As such, the therapy can treat the underlying disorder, and minimize/repair damage to the oral mucosa.

When patients are suffering from viral disorders such as cold sores, shingles, aphthous ulcers, and the like, the compositions can also include, or be co-administered with, antiviral agents. Particularly when the patients suffer from pain in their mouth, whether from bacterial or viral causes, physical injuries, or oral surgery, including tonsillectomies, uvulaplasties, scaling and root planning, grafting, and the like, the formulations described herein can help maintain homeostasis in the oral mucosa, which can accelerate healing, and can include anesthetics such as lidocaine, marcaine, xylocaine, and the like, to help alleviate pain. Anti-inflammatory agents can also be present.

Ears

Glutathione and ascorbate play a critical role in innate immune factors in the auditory system. This therapy can therefore offer auditory protection, repair and reduced inflammation, which could reduce the severity or incidence of auditory diseases that are primary disorders (e.g., otitis media) or secondary to other disorders or drug reactions.

Upper GI Tract

Glutathione and ascorbate play a critical role in innate immune factors in the upper GI tract. This therapy can therefore offer esophageal, gastric, hepatic, pancreatic, small intestinal, colonic and rectal protection, repair and reduced inflammation, which could reduce the severity or incidence of GI diseases that are primary disorders (e.g., esophagitis, hepatitis C, pancreatitis, acid reflux) or secondary to other disorders (e.g., cystic fibrosis) or drug reactions.

Lower GI Tract

Glutathione and ascorbate play a critical role in innate immune factors in the lower GI tract. This therapy can therefore offer colonic and rectal protection, repair and reduced inflammation, which could reduce the severity or incidence of GI diseases that are primary disorders (e.g., Crohn's, ulcerative colitis, inflammatory bowel disease) or secondary to other disorders (e.g., cystic fibrosis) or drug reactions.

Urinary Tract

Glutathione and ascorbate play a critical role in innate immune factors in the urinary tract. This therapy can therefore offer urinary tract protection, repair and reduced inflammation, which could reduce the severity or incidence of urinary tract diseases that are primary disorders (e.g., bladder cancer, cystitis, urinary tract infections) or secondary to other disorders (e.g., smoking or infection) or drug reactions.

Renal

Glutathione and ascorbate play a critical role in innate immune factors in the renal system. This therapy can therefore offer renal protection, repair and reduced inflammation, which could reduce the severity or incidence of renal diseases that are primary disorders (e.g., kidney cancer) or secondary to other disorders (e.g., cystic fibrosis, drug toxicity) or drug reactions. This therapy has the potential to reduce dosages of other drugs thereby limiting exposure of the kidneys to toxic drug levels.

Urogenital Tract

Glutathione and ascorbate play a critical role in innate immune factors in the urogenital system. This therapy can therefore offer urogenital protection, repair and reduced inflammation, which could reduce the severity or incidence of urogenital diseases that are primary disorders (e.g., HPV) or secondary to other disorders (e.g., menopause, *Chlamydia* infection) or drug reactions (e.g., fungal infection). This therapy has the potential to reduce dosages of other drugs thereby limiting exposure of the urogenital tract to toxic drug levels.

Skin, Hands and Feet

Glutathione and ascorbate play a critical role in innate immune factors in the skin, hands, finger and toe nails, and feet. This therapy could offer protection, repair and reduced inflammation to the skin and feet, which could reduce the severity or incidence of dermatological diseases that are primary disorders (e.g., bullous diseases, connective tissue diseases, i.e., lupus, allergic reaction, acne, eczema, psoriasis) or secondary to other disorders (e.g., viral infection, UV damage) or adverse drug reactions (e.g., dry skin, mucositis, fungal infection). This therapy has the potential to reduce dosages of other drugs thereby limiting exposure of the skin and feet to noxious drug levels.

Circulatory System

Glutathione and ascorbate play a critical role in innate immune factors in the circulatory system. This therapy can therefore offer protection, repair and reduced inflammation to the circulatory system, which could reduce the severity or incidence of circulatory diseases that are primary disorders (e.g., atherosclerosis) or secondary to other disorders (e.g., pulmonary hypertension, endocarditis) or drug reactions (e.g., azithromycin). This therapy has the potential to reduce dosages of other drugs thereby limiting exposure of the circulatory system to toxic drug levels. For example, treating earlier stage chronic obstructive pulmonary disease (COPD) with inhaled corticosteroid therapy combined with a long-acting beta agonist, reduced cardiac deaths in post hoc data queries. Therefore decreasing inflammation in the discrete system (e.g., lungs) may have systemic effects (e.g., circulatory system). The compositions and formulations of the present invention can be used to establish and/or maintain homeostasis in the mucosal environment of the lungs of a smoker or former smoker to reduce the risk or incidence of lung cancer and/or smoking-related diseases or disorders. The compositions and formulations of this invention can also be used in combination with therapeutic agents to treat lung cancer and/or smoking-related diseases or disorders, with the benefit that the therapeutic agent is effective at a lower dose when used in combination with a composition or formulation of this invention.

Cancer

Cancer is caused by the dysregulation of multiple pathways and is often exacerbated by oxidative stress and the deactivation of innate immune defenses. This therapy could offer protection, repair and reduced inflammation, which could reduce the severity or incidence of primary cancers (e.g., bladder, lung, breast) or cancers that are secondary to other disorders (e.g., thyroid, cervical, tonsilar) or drug reactions (e.g., immunosuppression, post-transplant lymphoma). This therapy has the potential to reduce dosages of other non-cancer related drugs, thereby limiting exposure to toxic drug levels. Additionally, it can be used in conjunction with cancer therapies to increase efficacy and/or decrease side effects.

Anticancer therapy is known to be associated with dry mouth, so administration of the compositions described herein to patients undergoing chemotherapy can minimize damage to the oral mucosa caused by dry mouth.

Autoimmune Diseases

Autoimmune diseases are caused by dysregulation of the immune system and is often exacerbated by oxidative stress and the deactivation of innate immune defenses. This therapy could offer protection, repair and reduced inflammation, which could reduce the severity or incidence of primary autoimmune diseases (e.g., lupus, arthritis, Crohn's disease, ulcerative colitis, multiple sclerosis, Type 1 diabetes) or autoimmune diseases that are secondary to other disorders (e.g., graft vs. host disease) or drug reactions (e.g., chemotherapy, immunosuppression). This therapy has the potential to reduce dosages of other autoimmune disease-related drugs, thereby limiting exposure to toxic drug levels. Additionally, it can be used in conjunction with other therapies to increase efficacy and/or decrease side effects.

Alzheimer's Disease

Alzheimer's disease is caused by genetic predisposition, neuroinflammation, disrupted neuronal communication, oxidative stress and possibly infectious agents. This therapy could offer protection, repair and reduced inflammation, which could reduce the severity or incidence of Alzheimer's disease or dementias that are secondary to other disorders (e.g., aging) or drug reactions (e.g., anesthesia, immunosuppression, chemotherapy). This therapy has the potential to reduce dosages of other Alzheimer's disease-related drugs, thereby limiting exposure to toxic drug levels. Additionally, it can be used in conjunction with other therapies to increase efficacy and/or decrease side effects.

Fungal Infections

Fungal infections are considered opportunistic infections especially in immunocompromised, cancer patients, and in diseases associated with steroid application (e.g., inhaled corticosteroids). They can be both community- and hospital-acquired and are most commonly found to be secondary to immunosuppressive, antibiotic, or steroid therapy. This therapy supplies innate immune factors, the components needed to prevent or treat primary fungal infections (e.g., athlete's foot) and reduce the incidence of or treat fungal infections secondary to other therapies (e.g., thrush). This therapy has the potential to reduce dosages of other fungal infection-related drugs, thereby limiting exposure to toxic drug levels. Additionally, it can be used in conjunction with other therapies to increase efficacy and/or decrease side effects.

Viral Infections

Viral infections are common in the general population though immunocompromised and cancer patients are most susceptible. This therapy supplies innate immune factors, the components needed to prevent or treat primary viral infections (e.g., HIV, HPV, HSV, influenza) and reduce the incidence of or treat viral infections secondary to other therapies (e.g., immunosuppression). This therapy has the potential to reduce dosages of other viral infection-related drugs, thereby limiting exposure to toxic drug levels. Additionally, it can be used in conjunction with other therapies to increase efficacy and/or decrease side effects and prophylactically in the general population during flu season. The methods and compositions of this invention can also be administered to an immunocompromised subject and/or a subject in a community or hospital setting that renders the subject at increased risk of infection (e.g., an intubated patient, a nursing home resident, a dialysis patient, etc.).

Bacterial Infections

Bacterial infections are common in the general population though immunocompromised and cancer patients are most susceptible. They can be both community- and hospital-acquired. This therapy supplies innate immune factors, the components needed to prevent or treat primary bacterial infections (e.g., ventilator and other hospital and community associated pneumonias, otitis media, sinusitis) and reduce the incidence of or treat bacterial infections secondary to other therapies (e.g., immunosuppression). This therapy has the potential to reduce dosages of other bacterial infection-related drugs, thereby limiting exposure to toxic drug levels. Additionally, it can be used in conjunction with other therapies to increase efficacy and/or decrease side effects.

Prophylaxis

In addition to providing methods of treatment, the compositions described herein can also be used to provide prevention of various diseases and disorders.

The formulations described herein can optionally be enhanced by supplying methionine, cysteine and/or N-acetylcysteine and other precursors required for the intracellular production of glutathione. Ensuring adequate intracellular concentrations of glutathione by oral, intravascular or inhalation delivery of molecules required for its intracellular production can:

1) ameliorate the effects of oxidant stress on the epithelium in the inflamed airway and
2) provide a supply of glutathione to be delivered to the mucosal surface from the host's airway epithelium as the diseased epithelium, in the non-cystic fibrosis condition, recovers.

Since cystic fibrosis patients cannot excrete glutathione from their airway epithelium, an approach of intracellularly generating glutathione may not be as effective for such patients as it would be for other patients.

While not wishing to be bound by a particular theory, it is believed that there is a general depletion of glutathione and ascorbate, which causes inflammatory cells in chronic inflammatory conditions to generate large amounts of reactive nitrogen and oxygen species that damage host tissues. Therefore, replenishing glutathione and ascorbate and the precursors needed to generate them intracellularly would be predicted to ameliorate the intensity of this inappropriate response by reducing the generation of these reactive species. The systemic delivery of glutathione, ascorbate and their precursors can, therefore, modify the intensity of pathologic inflammation systemically. This approach can therefore be used therapeutically and prophylactically in cystic fibrosis as well as other chronic conditions.

In the pulmonary area, for example, there are a number of smoking related disorders, such as COPD, cardiac disorders, urinary tract disorders including cancer, gastrointestinal disorders such as peptic ulcer disease, and the like, which can be prevented, at least to some extent, by administering the formulations prophylactically. Prophylactic administration can establish and/or maintain homeostasis in the mucosal tissue, and help prevent damage to the tissue.

The compositions and formulations of this invention can also be administered to a subject to ameliorate unwanted effects of other therapies. For example, the compositions and formulations of this invention can be administered to a subject that is taking inhaled steroids (ICS), which are linked to increased pneumonia risk in subjects with chronic obstructive pulmonary disease (COPD), as well as an increased risk of developing thrush, and/or to a subject that is taking a long acting beta antagonist (LABA), which is linked to increased risk of death in subjects with asthma. By administering the compositions and formulations of this invention to such subjects and thus establishing or maintaining mucosal membranes in the subject in homeostasis, the effective dose of the ICS or LABA can be reduced, thereby reducing the subject's risk of these undesirable side effects.

The compositions can also be administered prophylactically during cold and flu season, so as to prevent viral infections in the lungs and other mucosal membranes. This is particularly true of medical workers, who are exposed to a variety of infectious agents, including viruses, bacteria, fungi, and the like. Where the mucosal membrane is maintained in homeostasis, it can help fight off infectious diseases, so prophylactic administration is particularly useful for such workers.

Subjects in areas with air pollution and/or contaminated air can be protected against the effects of air pollution and/or contaminated air on the lungs and other mucosal membranes by prophylactically administering the formulations to the desired mucosal membranes. For example, military personnel, fireman, factory workers, and the like that live and/or work in an air-polluted and/or contaminated environment (e.g., contaminated by gas, toxic vapors, chemical spill, smoke, dust, etc.) can benefit from prophylactic administration of the formulations.

Prophylactic administration of the formulations can also be useful when a subject is exposed to dry air and other airway-irritating and/or contaminated environments, such as those experienced when traveling (e.g., on a plane, train, bus, car, etc.).

Prophylactic oral administration of the compositions and formulations of this invention can minimize dry mouth, regardless of its causes. The compositions for prophylaxis and/or treatment of dry mouth include toothpastes, mouthwashes, gels, and creams. In addition to the active ingredients described herein, therapeutic agents, such as sodium monofluorophosphate, enzymes such as glucose oxidase, lactoferrin, lactoperoxidase and lysozyme, and, to protect against the formation of PBF (plaque biofilm), enzymes such as mutanase and dextranase can be added.

The compositions and formulations of this invention can also be administered to a subject undergoing radiation therapy to ameliorate radiation-induced mucositis, as well as to treat and/or prevent infection secondary to mucositis.

With respect to gastrointestinal ("GI") administration, the formulations can prevent certain GI disorders, including peptic ulcer disease, by maintaining homeostasis in the gastrointestinal tract.

IPF exacerbations are linked to GI reflux and GERD (Acute Exacerbations in Patients With Idiopathic Pulmonary Fibrosis, *Respiratory Research*, 2013 Aug. 21), which can effect lung transplants. The compositions described herein can be administered to protect the airway from reflux damage to the epithelium.

With respect to rectal or vaginal administration, maintaining the mucosal membranes in homeostasis can prevent tears or other tissue damage, which can lower the likelihood of contracting diseases such as HIV, herpes, syphilis, and the like.

With respect to organ transplants, one can minimize and/or prevent damage to certain tissues by contacting them with the compositions and formulations described herein. Accordingly, the components can be added to perfusion liquids or used as components of a liquid used to slow the deterioration of an organ intended for transplantation.

The present invention is explained in greater detail in the following non-limiting examples.

EXAMPLES

Example 1: Preparation of Formulation 1

Glutathione (150 grams), ascorbic acid (10 grams) and sodium bicarbonate (45.7 grams) are added to a 1 L volumetric flask and brought to a final volume using deionized distilled water.

Example 2: Preparation of Formulation 2

Glutathione (150 grams), ascorbic acid (48.4 grams) and sodium bicarbonate (84 grams) are added to a 1 L volumetric flask and brought to a final volume using deionized distilled water.

Example 3: Treatment of a Patient Diagnosed with Asthma

Patient A was a 50 year old Caucasian female with severe asthma diagnosed in childhood and who received continuous systemic steroids to manage her condition since age 13. The patient underwent hospitalization for asthmatic exacerbations several times per year and reported dyspnea on exertion (DOE), greatly limiting her exercise tolerance even between exacerbations. After initiating inhalation therapy with Formulation 2, the patient expelled copious mucus plugs, and her forced expiratory volume in one second (FEV1) increased by 30%. After taking this medication for 2 months, the patient reported that she felt better overall and is now able to run for an hour at a time without shortness of breath.

Typical treatment entailed use of a nebulizer once or twice a day. The standard dose of Formulation 2 was a 4 ml volume nebulized for a ten minute period.

Example 4: Treatment of a Patient Diagnosed with Cystic Fibrosis

Patient B was a 41 year old Caucasian male diagnosed with cystic fibrosis (CF), severe lung disease and a clotting disorder. He did not tolerate and refused to use hypertonic saline and other standard inhaled therapies because he felt they were either ineffective or, in the case of hypertonic saline, induced a harsh, unproductive cough that often resulted in massive hemoptysis. This individual was significantly short of breath with excursion prior to using the formulation. The patient inhaled Formulation 1 twice a day. Within a week of starting treatment with Formulation 1, the patient reported a significant decrease in DOE and reported being able to climb two flights of stairs without difficulty, an activity he would not have considered attempting prior to starting this therapy. This patient took Formulation 1 for approximately 2 years (2007-2009) until he rapidly deteriorated and died secondary to an acute episode of massive hemoptysis associated with his coagulopathy.

The standard dose of Formulation 1 was a 4 ml volume nebulized for a ten minute period.

Example 5: Treatment of a Patient Diagnosed with Cystic Fibrosis

Patient C was a 51 year old Caucasian female diagnosed with cystic fibrosis. She began taking Formulation 1 by inhalation in 2007 after repeated extended hospitalizations for CF exacerbations requiring intravenous antibiotics associated with deteriorating lung function. Since beginning this therapy, the patient has only occasionally required hospitalizations for 3-4 days. Once during the five year period, the patient reported that this inhaled formulation "stopped working." Investigation revealed that the patient mistakenly received 25% of the prescribed dose during this period. Reinstitution of the full dose alleviated her symptoms. Additionally, this patient reported that after about two weeks, even the correct formulation began to lose effectiveness. Formulation 2 is now freshly prepared every two weeks for Patient C. There has been no perceived clinical deterioration of Formulation 2 when it is freshly prepared every two weeks.

Example 6: Treatment of a Patient Diagnosed with Bronchiolitis Obliterans Syndrome Patient D was a 28 year old Caucasian female diagnosed with end-stage CF lung disease. The patient had undergone lung transplant evaluation at another hospital and was admitted to our hospital for severe bilateral pneumonia. The patient was taking nebulized albuterol, dornase alfa, hypertonic saline, and tobramycin (TOBI). She routinely experienced hemoptysis using these and other nebulized antibiotics. She found the inhalation of hypertonic saline especially difficult to tolerate because it often induced a violent non-productive cough and vomiting. In an attempt to address the patient's suffocating, copious, and viscous airway secretions, she began treatment with Formulation 1 in November 2010. Inhalation treatment was carried out 2-6 times a day until she underwent a bilateral lung transplant in March 2011. The patient reported that this treatment was the only "source of relief." The patient reported having administered it whenever "I felt too congested to walk around or function." She felt this formulation was very well tolerated and that it stabilized her condition.

The same patient, after her lung transplant, began taking the inhaled formulation one year post transplant in an attempt to address recurrent episodes of infection and A1 rejection characterized by T-cell infiltration on transbronchial biopsy and persistent severe airway inflammation characterized by an erythematous, friable mucosa, copious mucopurulent secretions, and airway mucus plugging. The recurrent acute episodes were treated with methylprednisolone, prednisone tapers, rabbit anti-thymocyte globulin, and multiple courses of oral and IV antibiotics. Although these episodes of rejection resolved, forced vital capacity (FVC) never exceeded 95% of expected values, FEV1 never exceeded 85% of predicted, and mid-volume flow rates (FEF25-75%) never exceeded 40% of predicted. Chest computerized tomography (CT) scans revealed persistent ground-glass opacity bilaterally in the lower lobes. Several months after receiving the rabbit anti-thymocyte globulin, the patient reported left-sided chest tightening. Bronchoscopy demonstrated A1 rejection, *Aspergillus* infection, *Pseudomonas* infection, decreased small airway function, friable airway tissue, and copious purulent secretions with mucus plugging. After treatment with methylprednisolone, prednisone taper, antifungals, and antibiotics, lung function recovered to levels reported above but a chest CT again demonstrated bilateral lower lobe ground-glass opacities. Bronchoscopy again revealed an inflamed erythematous friable mucosa with copious mucopurulent airway secretions and complete obstruction of the left lower lobe by viscous mucus. Upon first treatment with the inhaled Formulation, the patient expectorated mucus plugs. Two months after beginning this therapy bronchoscopy revealed a normal-appearing airway with resolution of all the pathology previously noted and a chest CT demonstrated resolution of the previously noted ground-glass opacities. Two months after the initial dose, the patient's pulmonary function tests had improved and were essentially normal with a FVC of 101% of predicted, FEV1 93% of predicted, and FEF25-75% of 73% of predicted. Clinically, the patient reported resolution of the previously noted chest tightness and has noted increased exercise tolerance.

Cystic fibrosis transmembrane conductance regulator (CFTR) plays critical roles in the regulation of inflammation and infection of the airway. The absence of functioning CFTR is either directly or indirectly associated with deficiencies in several specific anions in the exocrine secretions that constitute the airway surface liquid. These anions, including glutathione, ascorbate, bicarbonate and thiocyanate, are essential cofactors for several innate systems essential to the maintenance of a homeostatic balance on mucosal surfaces. It is the intent, with some embodiments of this invention, to restore the ionic composition in these airways to affect down-regulation of pathologic inflammatory responses, suppress neutrophil recruitment, redirect host destructive ROS and RNI to species with more selective antimicrobial activity, alter the growth supportive environment for airway pathogens, and provide critical cofactors for the function of innate defense factors including lactoperoxidase and lactoferrin. In some embodiments, this will be accomplished by inhaled delivery of nebulized liquid containing a combination of glutathione, bicarbonate, thiocyanate and ascorbate at concentrations and in forms designed to replenish their ratios in the airway surface liquid to that associated with health. It is also a focus of this invention that all of these systems need to work together to assure a healthy homeostasis and that the ratios of these selected ions are critical to the orchestration of the host beneficial actions of these potentially host toxic factors. It follows that replenishing only one of the anions without consideration of the others may further disrupt the imbalance between these systems and exacerbate the disease process.

The airway pathology of the cystic fibrosis patient provides evidence for the critical roles of the ionic composition of exocrine secretions (airway surface liquid) for the functional maintenance of a mucosal surface. All of these patients have mutations in both alleles of a gene for cystic fibrosis transmembrane conductance regulator (CFTR) that functions as a precisely regulated anion channel to control ion and fluid homeostasis in the secretions that bathe epithelial surfaces. In addition to the initially identified chloride and associated sodium imbalances, secretions from these subjects have variously been reported to be deficient in glutathione, bicarbonate and thiocyanate, all of which have been directly attributed to the lack of CFTR function. There are also several other deficiencies and dysfunctions that likely are the indirect consequence of the loss of anion transport. These include, among others, ascorbate deficiency, insufficiencies in pancreatic enzymes, dysfunctions in mucins, and reduction of inducible nitric oxide synthase expression by airway epithelial cells and a consequent diminution of exhaled nitric oxide. The lack of function of the single gene product of cftr results in dehydrated accumulation of macromolecules, mucus plugging of ducts and blocking of delivery of macromolecules and interference with cilia function. It also results in dysregulation of inflammation resulting in an inappropriate infiltration of massive numbers of neutrophils and consequent overproduction of reactive oxygen species (ROS) and reactive nitrogen intermediates (RNI). There is also a predisposition to infection of the airway characteristically with opportunistic *Pseudomonas aeruginosa* that ultimately leads to morbidity and mortality in the majority of CF patients. This species apparently utilizes the overproduction of RNI by the host inflammatory response to drive nitrate respiration necessitated by the reduction of oxygen in the inflammatory environment.

While the loss of CFTR function can be ascribed to the etiology of CF, there is also evidence that CFTR function may be compromised in other chronic inflammatory lung diseases. It is the target of this invention to restore the ionic composition in these airways to affect down-regulation of the inflammatory response, suppression of neutrophil recruitment, redirection of host destructive ROS and RNI to species with more selective antimicrobial activity, altering the growth supportive environment for CF pathogens, and to provide critical cofactors for the function of innate defense factors including lactoperoxidase and lactoferrin.

This will be accomplished by inhaled delivery of nebulized liquid containing glutathione, bicarbonate, thiocyanate and ascorbate at concentrations designed to ultimately replenish the levels to that found in healthy airway surface liquid.

The central premise of this proposal is that the healthy airway maintains homeostasis through the ionic composition of the exocrine secretions of the submucosal glands distributed along the conducting airways of humans. It is assumed that inhaled particulates and potential pathogens would initially encounter the airway surface liquid and not the underlying airway epithelium in a normally healthy individual. The components of these secretions make critical contributions both to the defense of the airway surfaces against infectious challenges and to the regulation of destructive inflammatory responses. Failure of this primary defense manifests as lung disease usually with systemic manifestations suggesting that regional pathologic airway inflammation will adversely affect other organs and systems outside the lung. One of the primary regulators of this ionic balance is the cystic fibrosis transmembrane regulator (CFTR) protein. When CFTR is absent, down regulated, or impaired (as demonstrated in cystic fibrosis (CF), chronic obstructive pulmonary disease (COPD), and asthma), the airway surface liquid has improper concentrations of selected ions, such as glutathione, bicarbonate, and thiocyanate, that are necessary to the function of critical soluble innate defense factors in the airway, regionally in the lung and systemically in the host. The result is a chronic inflammatory state within the airway that affects other systems important to maintaining airway homeostasis and lung function (i.e., ascorbate and inducible nitric oxide synthase on airway epithelial cells) and the general health of the afflicted individual. The hypothesis of this proposal is that restoring key components of the airway surface liquid will reestablish the function of the innate defense system within the airway, regionally in the lung and, in many disease states, systemically in the affected individual and be therapeutic in a number of chronic and acute pulmonary diseases.

In addition to the key mechanical defenses that facilitate airway clearance of potentially harmful inhaled particulates and microbes, the airway surface liquid normally also provides a complex chemical defense by bathing the airway surface with exocrine secretion of soluble molecules that provide direct antibacterial activity and help regulate the host inflammatory response to these insults. The airway surface and the glandular ductal epithelia likely play important roles in the post-production modulation of the composition of these glandular products through the function of the apical membrane protein CFTR. In the ideal defense, microorganisms would be neutralized and cleared by the intrinsic antimicrobial molecules that bathe the airway surface without need of a second line of defense and without cellular contact. Lactoferrin (LF), lactoperoxidase (LPO), lysozyme, mucins, and secretory IgA are among the principal antimicrobial proteins found in exocrine secretions that bathe mucosal surfaces, including the conducting airways. Both LF and LPO are dependent on molecules and anions that are delivered to the airway surface liquid either by glandular ductal epithelial cells or by the ciliated epithelium lining the airways. Specifically, hydrogen peroxide is synthesized by the NADPH oxidase family member dual oxidase 2 (DUOX 2) expressed by ductal epithelial cells, while nitric oxide (NO·) production is contributed by the ciliated epithelial cells that express inducible nitric oxide synthase (iNOS). Furthermore, there is evidence that CFTR is not only a channel for chloride, but is critical to the transport of several anions, including bicarbonate ($HCO_3^-$), reduced glutathione (GSH), nitrosoglutathione (GSNO), and thiocyanate ($SCN^-$), that have demonstrated critical roles in the function of LF, LPO, mucins, $H_2O_2$, $NO^-$, and superoxide anion ($O_2^-$). Several reports cite that various exocrine secretions of cystic fibrosis patients and other airway conditions with direct or indirect modifications in CFTR (e.g., COPD, asthma, IPF, ciliary dyskinesia, etc.) are deficient in GSH, $HCO_3^-$, $SCN^-$, NO, and/or ascorbate.

Cystic fibrosis transmembrane conductance regulator (CFTR) is a multidomain integral apical membrane glycoprotein member of the ATP-binding cassette (ABC) that is required to control ion and fluid homeostasis on epithelial surfaces. Dysfunctions in the CFTR epithelial anion channel are fundamental to the etiology of cystic fibrosis (CF), a disease in which all individuals clinically diagnosed have mutations in both CFTR alleles. The absence of this precisely regulated anion channel activity disrupts ionic and water homeostasis on exocrine epithelial surfaces resulting in dehydrated accumulations of macromolecules. While this occurs on most exocrine surfaces, there are two sites where the dysfunction has profound pathologic effect. In the pancreas there is a failure of bicarbonate-rich fluid and enzyme secretion that impairs intestinal digestion and nutrient absorption of fats and fat-soluble vitamins with serious consequence. The second site is in the conducting airways of the lungs, where the loss of CFTR function results in viscous mucus accumulation that impairs intrinsic clearance. Together, the thick mucus and subsequent impaired clearance allows for the colonization and accumulation of microorganisms that provoke damaging inflammatory responses, which lead to an overall loss in airway function. There are three apparently paradoxical aspects to the pathologic progression that distinguishes CF from other inflammatory airway diseases. Unlike the plethora of pathogens associated with other states of compromised immunity, such as chronic neutropenia, chronic granulomatous disease, leukocyte adhesion deficiencies, or advanced AIDS, infection with a single pathogen (most notably *Pseudomonas aeruginosa*) is responsible for the vast majority of morbidity and mortality in cystic fibrosis. Furthermore, the unique environment of the CF airway results in the genetic adaptation of *P. aeruginosa* from the environmentally acquired, initially LPS smooth, motile, and antibiotic susceptible isolates to a mucoidy phenotype characterized by the over-production of an extracellular polysaccharide (alginate) with concomitant loss of the O-side chain addition to lipopolysaccharide (LPS). Additionally, there are multiple other genetic adaptations that confer resistance to innate and acquired immune defenses and antibiotic therapy and permit these normally aerobic bacteria to grow in an environment with reduced oxygen. The transition to a mucoidy phenotype and its associated genotypic modifications generally heralds a severe decline in the health status of the CF patient.

The second feature unique to the CF airway is the chronic presence of neutrophils on the airway surface, even in the apparent absence of established infection. Normally, when neutrophils are recruited into the airway, NO produced by inducible nitric oxide synthase (iNOS) acts in a negative feedback loop to prevent neutrophil sequestration in the airway. However, in CF, the epithelial cells of the respiratory tree have been shown to be deficient in the expression of iNOS compared to non-CF airways. iNOS expression has been shown to be mediated by reduced and oxidized glutathione (GSH and GSSG, respectively). Because CFTR is the primary transporter of GSH, CF patients, who are characterized by complete deficiency or severely malfunctioning CFTR, do not have GSH or GSSG in their airway surface liquid; therefore, lacking CFTR leads to decreased levels of GSH and subsequent down-regulated iNOS expression. Thus, the airway has decreased NO concentrations leading to chronic neutrophil recruitment and sequestration within the CF lung. Studies demonstrate that when exogenous reducing equivalents are restored in the airway, epithelial iNOS expression increases.

In contrast to the deficiencies in iNOS in airway epithelial cells, CF patients are not deficient in iNOS expression by professional phagocytes, including monocytes and neutrophils. In comparison to non-CF subjects with similar respiratory inflammation, CF patients have demonstrably decreased exhaled NO. The airway surface liquid of CF patients contains significant quantities of NO products, including nitrate, nitrite, nitrosotyrosine, and peroxynitrite. These data would suggest that there is NO being produced either by alternate forms of NOS (eNOS and/or nNOS) or more likely by iNOS from inflammatory cells in the area. There is strong evidence that the neutrophils in the submucosa express significant quantities of iNOS. It is also probable that the neutrophils on the mucosal surface, as well as the monocytes/macrophages, alveolar macrophages, and mast cells, contribute to the production of NO products. In contrast to the epithelial cells, these inflammatory cells would characteristically also produce $O_2^-$, $H_2O_2$ and myeloperoxidase, all of which would serve to further oxidize NO, especially in the absence of antioxidants (ostensibly GSH) in the mucosal milieu. While the peroxynitrite would theoretically be more toxic than NO or GSNO, it would also be more readily converted to nitrate, nitrotyrosine and nitrosamines. It is clear that *P. aeruginosa* that lack nitric oxide reductase are incapable of growing by nitrate respiration due presumably to the toxicity of the nitric oxide generated during nitrate metabolism. It is also evident that there is adaptation of the bacteria that is necessary for optimum nitrate respiration and that this adaptation results in increased resistance to ROS and RNI. However, *P. aeruginosa* is sensitive to $H_2O_2$ and NO adducts, including nitrosoglutathione (GSNO) and NONOate, as well as nitrite. Furthermore, it is evident that the addition of GSH to GSNO or nitrite results in a more potent antibacterial specie, presumably from enhanced release of NO proximal to the bacterial target, suggesting that *P. aeruginosa* is vulnerable to NO toxicity. At the same time, *P. aeruginosa* is dependent on NO products for growth in the absence of oxygen. The interactions between $O_2^-$, $NO^-$, GSH, GSSG, $H_2O_2$, $HCO_3^-$, and the enzymes or molecules that depend on these for function are complex.

Inducible NOS associated with phagocytic cells has been suggested to serve antimicrobial function through the generation of NO that reacts with $\kappa_2^-$, also generated by the phagocytic cell, to yield the reactive species peroxynitrite ($ONOO^-$). Ideally this occurs within a phagosome delivered to the target surface and not to the extracellular environment where it might damage host tissues and lose effectiveness against its target. In contrast, the NO generated by the iNOS of ciliated epithelial cells apparently is released to the airway surface environment, but in the presence of CFTR transported glutathione. There is evidence that NO reacts with glutathione to form the S-nitrosothiol nitrosoglutathione (GSNO), which is likely the biologically active species at the non-CF airway surface and not the NO that is delivered to the phagosome of the professional phagocyte. It is also clear that the GSNO is in the presence of excess GSH in the normally healthy airway. Our preliminary data indicate that GSH acts to limit the ability of *P. aeruginosa* to utilize nitrate, nitrite, or nitric oxide to grow under anaerobic conditions. Furthermore, nitrite and nitric oxide in the presence of GSH inhibit the aerobic growth of *P. aeruginosa*. Our data have also demonstrated that the antipseudomonal activities of GSNO and other nitric oxide donors are potentiated in the presence of exogenous glutathione. In addition, there are reports that both LF and LPO can interact with NO to generate more potent antimicrobial species.

Clinical and experimental evidence suggest that the unique environment presented by the CF airways selectively permits the growth of *P. aeruginosa*. Evidence suggests that the airway environment of the CF lung where *P. aeruginosa* grows is anaerobic/microaerophilic. In order for *P. aeruginosa* to exhibit exponential growth as is evident on the CF airway surface, there must be an alternative to oxygen dependent metabolism. *P. aeruginosa* is capable of an eight electron reduction of nitrate to nitrogen. This nitrate respiration supports excellent growth of selected strains of *P. aeruginosa* under conditions of oxygen limitation. It is proposed that the inflammatory character that results in the airway mucosa of the CF respiratory tree generates nitrate in a form and quantity sufficient to select for and support the growth of *P. aeruginosa*. Recent studies suggest that CFTR may play an important role in the transport of the biological reductant reduced glutathione (GSH) to the airway surface liquid (ASL). Further evidence suggests that the ASL of the CF patient is deficient in GSH compared to that of non-CF airways. This deficiency would certainly result in a reduction in the antioxidant capacity operating on airway surfaces and predispose these surfaces to oxidative damage. It is further the contention of this proposal that the deficiency in secreted glutathione results in a diminished capacity of the ASL to inhibit P. aeruginosa from establishing an infection at these mucosal surfaces. It is proposed that glutathione (either GSH or GSSG) is critical to the antimicrobial function of NO and that the normally healthy airway generates an NO adduct of glutathione (S-nitrosoglutathione, GSNO) that serves both to deliver NO in an antibacterial form and to limit the conversion of NO to nitrate, thus restricting the availability of this growth-critical substrate. The antimicrobial properties of the airway surface liquid are thus facilitated by the production of NO by the airway epithelial cells that in non-CF subjects express iNOS.

LF has the ability of high affinity binding of two ferric ions in coordination with the binding of carbonate. Four of the coordinate sites of iron are associated with amino acid residues in each of the pair of iron binding clefts in the N- and C-terminal lobes of the LF protein. The remaining two coordinate sites of ferric ion are occupied by two of the coordinate sites of carbonate while the third coordinate site of carbonate is bound to its amino acid residue in the LF lobes. This synergistic binding results in an unusually high affinity resulting in stabilization of the iron in the ferric transition state. Other anions (e.g., $HCO_3^-$) are also capable of fitting in to the anion coordinate site of LF, but can only occupy one of the two free coordinate sites of iron. The remaining free coordinate site can then participate in a Haber-Weiss interaction in the presence of $H_2O_2$, generating hydroxyl radical. This reaction could be amplified if there is reducing potential, such as $O_2^-$ or ascorbate, available to cycle the iron to a ferrous state. In addition to the reducing potential of ascorbate, it is of a size and configuration that it fits in the anion coordinate sites of lactoferrin, limiting stabilized carbonate-$Fe^{3+}$ binding. If generated proximal to a susceptible bacterial surface, it would kill potential pathogens, conversely it could also damage host tissues. Therefore it would be predicted that iron binding by LF in coordination with carbonate would scavenge iron and serve an antioxidant function. In contrast, bicarbonate and ascorbate would serve to facilitate the generation of reactive oxygen species and bactericidal activity on a target pathogen surface. Therefore the ratio of carbonate to bicarbonate, especially in the presence of other species such as ascorbate, $O_2^-$, $H_2O_2$ and NO, may serve an important regulatory function in determining the antibacterial vs. antioxidant effects of LF.

Furthermore, bicarbonate is transported into the mucosa via CFTR; therefore, CF patients lack bicarbonate within their ASL, which impairs LF's activity. Additionally, our preliminary studies have shown that bicarbonate inhibits the alginate production associated with the detrimental emergence of the mucoidy phenotype of P. aeruginosa. Further hindering LF activity is the chronic inflammatory state within the CF airway that depletes already low reserves of ascorbate. Ascorbate also works with GSH to maintain a reduced environment, as well as maintain proper mucociliary clearance. Thus, restoring bicarbonate and ascorbate to the airway surface can aid in LF activity and stymie the development and/or expression of mucoidy P. aeruginosa.

LPO catalyzes the oxidation of $SCN^-$ by $H_2O_2$ to form hypothiocyanite ($OSCN^-$), a potent antimicrobial species that works by oxidizing essential sulfhydryls of target proteins on bacterial surfaces. This can effectively inhibit bacterial metabolism through neutralization of enzymes such as hexose kinases necessary for the transport of sugars. Unlike its neutrophil counterpart myeloperoxidase (MPO), LPO cannot use the halide $Cl^-$ as substrate and does not generate the potentially host noxious product hypochlorous acid (HOCl). While having potent antimicrobial activity, $OSCN^-$ has the added advantage that it is relatively innocuous to host tissues. Therefore in the presence of adequate concentrations of $SCN^-$ and functioning LPO, there would be competition for $H_2O_2$ that would limit the activity of MPO generation of HOCl. There is also evidence that MPO may use $SCN^-$ in preference to Cl. Conversely, limitations in $SCN^-$ would serve to favor the less discriminating and more reactive HOCl.

Therefore, restoring CFTR transported glutathione, $HCO_3$, and $SCN^-$ and enhancing the reducing potential in the CF airway by adding ascorbate into the airway, will reestablish the ASL to a more "normal" ionic balance that is suited to restore proper function of natural defenses, such as LF and LPO activity, and thus, will slow the progression of CF and several other lung diseases. Replacing these elements with unique inhaled formulations will enhance homeostatic mechanisms required for mucociliary clearance and other host-sparing antibacterial functions and will reduce the pathologic inflammatory elements that uncontrolled damage the host by accelerating lung function deterioration favoring P. aeruginosa growth.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method for reducing the onset and/or progression of bacterial growth in a subject's airway, comprising prophylactically administering by inhalation to the airway of the subject an effective amount of a composition comprising:
    a) a glutathione, or a pharmaceutically-acceptable salt of glutathione;
    b) an organic acid or a pharmaceutically-acceptable salt of an organic acid; and
    c) a carrier,
    wherein the subject suffers from a pulmonary or airway disorder or disease selected from the group consisting of an inflammatory lung disease and/or infection of the lung, inflammation and/or infection associated with lung transplantation, acute lung rejection, asthma, cystic fibrosis, chronic obstructive pulmonary disease (COPD), and any combination thereof.

2. The method of claim 1, wherein the organic acid is ascorbic acid.

3. The method of claim 1, wherein the composition is in the form of a particle.

4. The method of claim 3, wherein the particle is mixed with a gas or liquid propellant for use in inhalation therapy.

5. The method of claim 1, wherein the composition comprises a pH adjusting agent.

6. The method of claim 5, wherein the pH adjusting agent is an agent selected from the group consisting of citric acid, sodium citrate, sodium bicarbonate, dibasic sodium phosphate, magnesium oxide, calcium carbonate and magnesium hydroxide, an acetate buffer, a citrate buffer, a phosphate buffer, a lactic acid buffer, a borate buffer, and any combination thereof.

7. The method of claim 5, wherein the pH adjusting agent is sodium bicarbonate.

8. The method of claim 1, comprising the further step of administering to the subject an effective amount of a therapeutic agent.

9. The method of claim 8, wherein the therapeutic agent is an inhaled corticosteroid (ICS) or bronchodilator.

10. The method of claim 9, wherein the therapeutic agent is selected from the group consisting of Fluticasone, Budesonide, Mometasone, Ciclesonide, Flunisolide, Beclomethasone, Albuterol, Levalbuterol, Ipratropium, Tiotropium, Formoterol, Arformoterol, Indacaterol, Aclidinium, Pirbuterol and any combination thereof.

11. The method of claim 1, wherein the glutathione is reduced glutathione.

12. The method of claim 1, wherein the subject suffers from an inflammatory lung disease and/or infection of the lung.

13. The method of claim 1, wherein the subject suffers from an inflammation and/or infection associated with lung transplantation or acute lung rejection.

14. The method of claim 1, wherein the subject suffers from asthma.

15. The method of claim 1, wherein the subject suffers from cystic fibrosis.

16. The method of claim 1, wherein the subject suffers from chronic obstructive pulmonary disease (COPD).

17. A method for reducing the onset and/or progression of bacterial growth in a subject in need thereof, comprising prophylactically administering by inhalation to the airway of the subject prior to a surgical procedure, intubation, mechanical ventilation, or post-operatively an effective amount of a composition comprising:
   a) a glutathione, or a pharmaceutically-acceptable salt of glutathione;
   b) an organic acid or a pharmaceutically-acceptable salt of an organic acid; and
   c) a carrier.

18. The method of claim 17, wherein the organic acid is ascorbic acid.

19. The method of claim 17, wherein the composition is in the form of a particle.

20. The method of claim 19, wherein the particle is mixed with a gas or liquid propellant for use in inhalation therapy.

21. The method of claim 17, wherein the composition comprises a pH adjusting agent.

22. The method of claim 21, wherein the pH adjusting agent is an agent selected from the group consisting of citric acid, sodium citrate, sodium bicarbonate, dibasic sodium phosphate, magnesium oxide, calcium carbonate and magnesium hydroxide, an acetate buffer, a citrate buffer, a phosphate buffer, a lactic acid buffer, a borate buffer, and any combination thereof.

23. The method of claim 21, wherein the pH adjusting agent is sodium bicarbonate.

24. A method for establishing and/or maintaining homeostasis in the mucosal tissue of a subject's airway, comprising prophylactically administering by inhalation to the airway of the subject an effective amount of a composition comprising:
   a) a glutathione, or a pharmaceutically-acceptable salt of glutathione;
   b) an organic acid or a pharmaceutically-acceptable salt of an organic acid; and
   c) a carrier,
   wherein the subject suffers from a pulmonary or airway disorder or disease selected from the group consisting of an inflammatory lung disease and/or infection of the lung, inflammation and/or infection associated with lung transplantation, acute lung rejection, asthma, cystic fibrosis, chronic obstructive pulmonary disease (COPD), and any combination thereof.

25. The method of claim 24, wherein the organic acid is ascorbic acid.

26. The method of claim 24, wherein the composition is in the form of a particle.

27. The method of claim 26, wherein the particle is mixed with a gas or liquid propellant for use in inhalation therapy.

28. The method of claim 24, wherein the composition comprises a pH adjusting agent.

29. The method of claim 28, wherein the pH adjusting agent is an agent selected from the group consisting of citric acid, sodium citrate, sodium bicarbonate, dibasic sodium phosphate, magnesium oxide, calcium carbonate and magnesium hydroxide, an acetate buffer, a citrate buffer, a phosphate buffer, a lactic acid buffer, a borate buffer, and any combination thereof.

30. The method of claim 28, wherein the pH adjusting agent is sodium bicarbonate.

31. The method of claim 24, wherein the glutathione is reduced glutathione.

32. The method of claim 24, wherein the subject suffers from an inflammatory lung disease and/or infection of the lung.

33. The method of claim 24, wherein the subject suffers from an inflammation and/or infection associated with lung transplantation or acute lung rejection.

34. The method of claim 24, wherein the subject suffers from asthma.

35. The method of claim 24, wherein the subject suffers from cystic fibrosis.

36. The method of claim 24, wherein the subject suffers from chronic obstructive pulmonary disease (COPD).

* * * * *

UNITED STATES PATENT AND TRADEMARK OFFICE
CERTIFICATE OF CORRECTION

PATENT NO. : 11,938,166 B2
APPLICATION NO. : 17/348096
DATED : March 26, 2024
INVENTOR(S) : Arnold et al.

Page 1 of 2

It is certified that error appears in the above-identified patent and that said Letters Patent is hereby corrected as shown below:

On the Title Page

(56) References Cited, OTHER PUBLICATIONS, Page 3, Column 2, Line 46, 2$^{nd}$ Gao et al. cite: Please correct "124-L30" to read --L24-L30--

In the Specification

Column 4, Line 51: Please insert a paragraph break between "water." and "In addition"

Column 30, Line 67; Please correct "CBT" to read --CB1--

Column 31, Line 14: Please correct "a subunit" to read --α subunit--

Column 31, Line 27: Please correct "(E chain)" to read --(ε chain)--

Column 31, Line 28: Please correct "E chain" to read --ε chain--

Column 55, Line 67: Please correct "A9-THC" to read --Δ9-THC--

Column 60, Line 59: Please correct "50 m" to read --50 μm--

Column 60, Line 61: Please correct "30 m" to read --30 μm--

Column 60, Line 62: Please correct "20 m" to read --20 μm--

Column 62, Line 10: Please correct "525-30" to read --S25-30--

Column 63, Lines 33-34: Please insert a paragraph break between "day)" and "In particular"

Column 64, Line 50: Please insert a paragraph break between "systemically" and "Inflammation"

Signed and Sealed this
Twenty-sixth Day of November, 2024

Katherine Kelly Vidal
*Director of the United States Patent and Trademark Office*

CERTIFICATE OF CORRECTION (continued)
U.S. Pat. No. 11,938,166 B2

Column 78, Line 46; Please correct "NO⁻" to read --NO--

Column 80, Line 22: Please correct "NO⁻" to read --NO--

Column 80, Line 27: Please correct "$\kappa_2^-$" to read --$O_2^-$--

Column 82, Line 8: Please correct "(HOCl)" to read --(HOCl)--